United States Patent
Reshetnyak et al.

(10) Patent No.: US 12,397,060 B2
(45) Date of Patent: Aug. 26, 2025

(54) pHLIP®-MEDIATED INTRACELLULAR DELIVERY OF IMMUNO-STIMULATORY COMPOUNDS

(71) Applicants: University of Rhode Island Board of Trustees, Kingston, RI (US); Yale University, New Haven, CT (US)

(72) Inventors: Yana K. Reshetnyak, Saunderstown, RI (US); Oleg A. Andreev, Saunderstown, RI (US); Donald M. Engelman, New Haven, CT (US); Anna Moshnikova, Warwick, RI (US); John Deacon, Tolland, CT (US)

(73) Assignees: University of Rhode Island Board of Trustees, Kingston, RI (US); Yale University, New Haven, CT (US)

( * ) Notice: Subject to any disclaimer, the term of this patent is extended or adjusted under 35 U.S.C. 154(b) by 977 days.

(21) Appl. No.: 17/423,849

(22) PCT Filed: Jan. 28, 2020

(86) PCT No.: PCT/US2020/015402
§ 371 (c)(1),
(2) Date: Jul. 16, 2021

(87) PCT Pub. No.: WO2020/159983
PCT Pub. Date: Aug. 6, 2020

(65) Prior Publication Data
US 2022/0088208 A1   Mar. 24, 2022

Related U.S. Application Data

(60) Provisional application No. 62/797,893, filed on Jan. 28, 2019.

(51) Int. Cl.
| | | |
|---|---|---|
| A61K 47/64 | (2017.01) | |
| A61K 9/00 | (2006.01) | |
| A61K 39/39 | (2006.01) | |
| A61K 47/42 | (2017.01) | |

(52) U.S. Cl.
CPC ........... *A61K 47/64* (2017.08); *A61K 9/0019* (2013.01); *A61K 39/39* (2013.01); *A61K 47/42* (2013.01)

(58) Field of Classification Search
CPC ......... A61K 47/64; A61K 39/39; A61P 35/00; A61P 37/04
See application file for complete search history.

(56) References Cited

U.S. PATENT DOCUMENTS

| | | |
|---|---|---|
| 8,076,451 B2 | 12/2011 | Reshetnyak et al. |
| 8,703,909 B2 | 4/2014 | Reshetnyak et al. |
| 8,846,081 B2 | 9/2014 | Reshetnyak et al. |
| 9,289,508 B2 | 3/2016 | Reshetnyak et al. |
| 9,415,045 B2 | 8/2016 | Blumberg et al. |
| 9,642,830 B2 | 5/2017 | Chang et al. |
| 9,676,823 B2 | 6/2017 | Reshetnyak et al. |
| 9,750,693 B2 | 9/2017 | Reshetnyak et al. |
| 9,814,781 B2 | 11/2017 | Reshetnyak et al. |
| 9,834,545 B2 | 12/2017 | Chen et al. |
| 10,011,630 B2 | 7/2018 | Vernejoul et al. |
| 10,045,961 B2 | 8/2018 | Chang et al. |
| 10,512,606 B2 | 12/2019 | Reshetnyak et al. |
| 11,267,853 B2 * | 3/2022 | Reshetnyak ............ A61P 35/00 |
| 2005/0256030 A1 | 11/2005 | Feng |
| 2008/0233107 A1 | 9/2008 | Reshetnyak et al. |
| 2012/0039990 A1 | 2/2012 | Reshetnyak et al. |
| 2012/0142042 A1 | 6/2012 | Reshetnyak et al. |
| 2015/0051153 A1 | 2/2015 | Reshetnyak et al. |
| 2015/0086617 A1 | 3/2015 | Reshetnyak et al. |
| 2015/0191508 A1 | 7/2015 | Reshetnyak et al. |
| 2016/0256560 A1 | 9/2016 | Reshetnyak et al. |
| 2017/0044206 A1 | 2/2017 | Altman et al. |
| 2018/0064648 A1 | 3/2018 | Reshetnyak et al. |
| 2018/0117183 A1 | 5/2018 | Reshetnyak et al. |
| 2018/0221500 A1 | 8/2018 | Reshetnyak et al. |
| 2018/0369425 A1 | 12/2018 | Reshetnyak et al. |
| 2019/0231904 A1 | 8/2019 | Reshetnyak et al. |
| 2019/0382448 A1 | 12/2019 | Reshetnyak et al. |
| 2020/0237926 A1 | 7/2020 | Reshetnyak et al. |
| 2020/0246420 A1 | 8/2020 | Reshetnyak et al. |
| 2020/0253872 A1 | 8/2020 | Reshetnyak et al. |
| 2020/0262881 A1 | 8/2020 | Reshetnyak et al. |
| 2020/0323882 A1 | 10/2020 | Reshetnyak et al. |
| 2024/0075170 A1 | 3/2024 | Reshetnyak et al. |

(Continued)

FOREIGN PATENT DOCUMENTS

| | | |
|---|---|---|
| CA | 3032186 A1 | 4/2012 |
| WO | WO-2006078816 A2 | 7/2006 |

(Continued)

OTHER PUBLICATIONS

Kushchayev et al. Cancer Management and Research, 2012, vol. 4, pp. 309-323.*
Qui et al. Small , 2018, 14 (15), 1703539, pp. 1-11.*
International Search Report and Written Opinion corresponding to International Patent Application No. PCT/US2020/015402, mailed Jun. 11, 2020.

(Continued)

*Primary Examiner* — Bao Q Li
(74) *Attorney, Agent, or Firm* — Sterne, Kessler, Goldstein & Fox P.L.L.C.

(57) ABSTRACT

The invention features a composition comprising an immuno-stimulatory compound and a pHLIP® peptide, e.g., an immunostimulatory compound that comprises a cyclic purine dinucleotide, which binds to a stimulator of interferon genes (STING) such as a cGAMP cyclic compound inside a cell.

22 Claims, 11 Drawing Sheets
Specification includes a Sequence Listing.

(56) References Cited

U.S. PATENT DOCUMENTS

| 2024/0173258 A1 | 5/2024 | Reshetnyak et al. |
| 2024/0342296 A1 | 10/2024 | Reshetnyak et al. |

FOREIGN PATENT DOCUMENTS

| WO | WO-2012021790 A1 | 2/2012 |
| WO | WO-2012047354 A2 | 4/2012 |
| WO | WO-2017165452 A1 | 9/2017 |
| WO | 2018/057912 A1 | 3/2018 |
| WO | WO-2018227132 A1 | 12/2018 |
| WO | WO-2020159983 A1 | 8/2020 |
| WO | WO-2020160009 A1 | 8/2020 |
| WO | WO-2020160031 A1 | 8/2020 |
| WO | WO-2020160047 A2 | 8/2020 |
| WO | WO-2020190733 A1 | 9/2020 |

OTHER PUBLICATIONS

Altschul, S.F., et al., "Basic Local Alignment Search Tool," Journal of Molecular Biology 215(3):403-410, Elsevier, United Kingdom (Oct. 1990).

Altschul, S.F., et al., "Gapped BLAST and PSI-BLAST: A New Generation of Protein Database Search Programs," Nucleic Acids Research 25(17):3389-3402, Oxford University Press, United Kingdom (Sep. 1997).

Ausubel, F., "Short Protocols in Molecular Biology," in Current Protocols in Molecular Biology, Third edition, pp. 1-79, John Wiley & Sons, Inc., United States (1995).

Corrales, L., et al., "Direct Activation of STING in the Tumor Microenvironment Leads to Potent and Systemic Tumor Regression and Immunity," Cell Rep. 11(7):1018-1030, Cell Press, United States (May 2015).

Henikoff, S., et al., "Amino acid substitution matrices from protein blocks," Proc Natl Acad Sci U S A 89(22):10915-10919, National Academy of Sciences, United States (Nov. 1992).

Ishikawa, H., et al., "STING is an endoplasmic reticulum adaptor that facilitates innate immuno signaling," Nature 455:674-678, Springer, Germany (Oct. 2008).

Needleman, S.B., et al., "A general method applicable to the search for similarities in the amino acid sequence of two proteins," J Mol Biol 48(3):443-453, Elsevier, Netherlands (Mar. 1970).

Pearson, W.R., et al., "Improved tools for biological sequence comparison," Proc Natl Acad Sci U S A 85(8):2444-2448, National Academy of Sciences, United States (Apr. 1988).

Smith, T., et al., "Comparison of biosequences," Adv. Appl. Math. 2(4):482-489, Elsevier, Netherlands (Dec. 1981).

Takeuchi, O., et al., "Pattern recognition receptors and inflammation," Cell 140:805-820, Cell Press, United States (Mar. 2010).

Woo, S.R., et al., "STING-dependent cytosolic DNA sensing mediates innate immune recognition of immunogenic tumors," Immunity 41:830-842, Cell Press, United States (Nov. 2014).

Yum, S., et al., "Roles of the cGAS-STING Pathway in Cancer Immunosurveillance and Immunotherapy," Annual Review of Cancer Biology, 3:323-344, Annual Reviews, United States (2019).

Moshnikova, A., et al., "Eradication of tumors and development of anti-cancer immunity using STINGa targeted by pHLIP," Front Oncol. 12:1023959, Frontiers Media, Switzerland (Oct. 2022).

\* cited by examiner

# pHLIP®-MEDIATED INTRACELLULAR DELIVERY OF IMMUNO-STIMULATORY COMPOUNDS

RELATED APPLICATIONS

This application is a national stage application filed under 35 U.S.C. § 371 of International Patent Application No. PCT/US2020/015402, filed Jan. 28, 2020, which claims the benefit of and priority under 35 U.S.C. § 119(e) to U.S. Provisional Application No. 62/797,893, filed Jan. 28, 2019, the entire contents of which are incorporated herein by reference in its entirety.

STATEMENT AS TO FEDERALLY SPONSORED RESEARCH

This invention was made with government support under R01 GM073857 awarded by the National Institute of General Medical Sciences of the National Institutes of Health. The government has certain rights in the invention.

INCORPORATION BY REFERENCE OF SEQUENCE LISTING

The contents of the sequence listing text file named "040984-511001WO_SL.txt." which was created on Jan. 28, 2020 and is 94,882 bytes in size, is hereby incorporated by reference in its entirety.

FIELD OF THE INVENTION

The present invention relates to immunotherapy.

BACKGROUND

Conventional methods of cancer treatment employ toxic agents that do not distinguish between normal and tumor tissues very well, and are therefore limited in their use because of their harmful side effects. Recent studies in cancer immunotherapy have shown that boosting the innate immune system of patients with cancer can have a critical effect in the outcome of cancer treatment, alone or in combination with conventional treatments Immuno-stimulating drugs exist, such as stimulator of interferon genes (STING) agonists, Toll-Like Receptor 7 (TLR-7) agonists, or retinoic acid-inducible gene I (RIG-I) agonists for instance, which have targets localized in the cytosol of a tumor cell. Although these drugs stimulate an immune response, it is necessary to not only specifically and efficiently target tumor cells to avoid adverse side effects but also to overcome the difficulty of introducing these drugs into the cytosol of tumor cells. Another limitation is that these drugs tend to be polar molecules that do not efficiently cross cell membranes. STING agonists, such as Cyclic guanosine monophosphate-adenosine monophosphate (cGAMP) for instance, are hydrophilic and negatively charged molecules. Such molecules are associated with poor membrane permeability, since cell membranes are non-polar, hydrophobic environments.

Thus, a current challenge in the field of immunotherapy is to find methods to deliver these immune-stimulating drugs across cell membranes specifically into the cytosol of tumor cells, while avoiding delivery into healthy cells. Systemic delivery of STING agonists can be associated with off-target inflammation and/or a global autoimmune response which could be deleterious for the patient.

SUMMARY OF THE INVENTION

The invention provides a solution to the problem of delivering STING and other immuno-stimulatory drugs to cancer cells and activated macrophages within the tumor microenvironment (TME). The compositions and methods described herein facilitate delivery of STING and other immuno-stimulatory drugs to cancer cells and macrophages, e.g., macrophages associated with tumors such as those within the TME.

Tumors are characterized by a TME of a lower pH than the surrounding tissues, because of the metabolism accompanying their rapid and uncontrolled cell proliferation, which results in a flux of acidity emerging from tumor cells and/or macrophages associated with or infiltrating a tumor. Moreover, due to the flux and the membrane potential, the extracellular pH is lowest at the surfaces of cancer cells (meaning the pH is in close vicinity of the cellular membrane or the pH is measured just near the cell membrane) and is significantly lower than the bulk extracellular pH (the pH at the distance from cell membrane) in tumors compared to normal tissues of the same tissue type. The low pH region persists at the cancer cell surfaces even in well-perfused tumor areas.

A pH Low Insertion Peptide (pHLIP®) is a water-soluble membrane peptide that interacts weakly with a cell membrane at neutral pH, without insertion into the lipid bilayer; however, at slightly acidic pH (<7.0), pHLIP® inserts into the cell membrane and forms a stable transmembrane alpha-helix. In addition to tumor cells characterized by low pH (<7.0), immune cells within a tumor mass are also characterized by low pH (<7.0). For example, the cells within the environment of a tumor mass, e.g., macrophages, are also characterized by low pH. By binding a pHLIP®, or pHLIP® equivalent, to an immune-stimulating drug, the compositions and methods specifically deliver the drug directly to the cancerous and immune (macrophages) cells and into their cytosols due to their acidic cell surfaces. Delivering immune-stimulatory compounds or drugs using pHLIP® peptides boosts the immune system, e.g., by stimulating the production of interferon-gamma, to mount and/or establish a tumor specific immune response and fight the cancer.

A significant advantage of this approach is that the augmented immune response stimulated by the pHLIP® constructs described herein are associated with few to no side effects for the patient.

Accordingly, the invention features a composition comprising an immuno-stimulatory compound and a pHLIP® peptide, e.g., an immunostimulatory compound that comprises a cyclic purine dinucleotide or its derivatives, which bind in a cell to STING. For example, the immunostimulatory compound binds to a STING inside a cell. Examples of STING compounds include Cyclic guanosine monophosphate-adenosine monophosphate (cyclic GMP-AMP (cGAMP)) or derivatives thereof, e.g., a —NH₂ or —SH derivative of the STING compound, 3',5'-cyclic diadenylic acid (c-di-AMP), or a cyclic diguanylate (c-di-GMP) cyclic compound, or a derivative thereof. In some examples, the immuno-stimulatory compound is a polar compound or a moderately hydrophobic compound. Such compounds are characterized by limited intracellular penetration by passive diffusion across a plasma membrane. In other examples, the immuno-stimulatory compound is delivered into a cell. A tumor cell or immune cell comprising a composition comprising an immuno-stimulatory compound and a pHLIP® peptide is also within the invention.

A compound is characterized as polar if it has a log P of less than −0.4. The immunostimulatory compound may be moderately hydrophobic. Exemplary cargo compounds, e.g., immune-stimulatory compounds or drugs, are polar, moderately hydrophobic or hydrophobic as defined by the following characteristics. Polar: Log P <−0.4; Moderately hydrophobic: 2.5<Log P <−0.4; and Hydrophobic: Log P >2.5. The polarity and/or hydrophobicity of an immunostimulatory compound is measured using methods known in the art, e.g., by determining Log P, in which P is the octanol-water partition coefficient. A substance is dissolved into an octanol-water mixture, mixed, and allowed to come to equilibration. The amount of substance in each (or one) phases is then measured. The measurements itself could be in a number of ways known in the art, e.g., by measuring absorbance, or determining the amount using NMR, HPLC, or other known methods. As described herein, moderately hydrophobic, for example, is defined as molecule with Log P value in the range of 2.5 to −0.4, there are a lot of examples. In some examples, the immunostimulatory compound induces its biological effect only when it is inside a cell. For example, the immunostimulatory compound by itself has limited intracellular penetration by passive diffusion across the plasma membrane. The invention provides a solution to the problem of limited intracellular penetration to target cells (such as tumor cells and tumor-associated immune cells), because pHLIP® peptide sequences mediate targeting of the immune-stimulatory compound to tumor cells and/or immune cells such as macrophages in the TME, and subsequent delivery of the compound into the targeted cells. To be active, the immunostimulatory compound needs to be delivered into cells by pHLIP®, i.e., the immunestimulatory compound cannot efficiently gain access to the cytosol without pHLIP®, which mediates its intracellular delivery.

In some embodiments, the composition further comprises a linker between the immuno-stimulatory compound and the pHLIP® peptide. Exemplary linkers include a disulfide bond or an acid-labile bond. In some examples, the linker is cleavable. In other examples, the linker is not cleavable. Exemplary cleavable linkers include those that are self-immolating. The purpose of self-immolating linker is to restore a drug, e.g., an immune-stimulatory compound such as a STING agonist, to its original structure following cleavage of the linker that linked it to the pHLIP® peptide. Self-immolative elimination is a spontaneous and irreversible disassembly of a multicomponent compound into its constituent fragments through a cascade of electronic elimination processes. Self-immolative elimination is driven by an increase in entropy coupled with the irreversible formation of thermodynamically stable products (e.g. $CO_2$). Such linkers have an advantage in that the cargo/therapeutic agent (drug) can be released in an unmodified form if it has an appropriate —$NH_2$ or —OH group, such as In general self-immolative linkers are well known linkers and widely used.

A modulator of polarity is optionally included in the composition. Such a modulator changes the overall polarity of the construct to optimize delivery to cancer and immune cells or a tumor mass. If the cargo is polar (Log P<−0.4), the hydrophobic modulator will increase the Log P of [the cargo-modulator] (Log P>−0.4). If the cargo is hydrophobic Log P>2.5, the polar modulator will decrease the Log P of [the cargo-modulator] (Log P<2.5). Non-limiting examples of modulators are fatty acids, PEG polymers, hydrophobic fluorescent dyes, or cyclic peptides. For example, if the cargo renders the composition too polar, a modulator agent is added to make the overall composition less polar, or if the cargo is not polar enough, a modulator is added to make the composition more polar. For example, linkers comprising such modulators have an advantage in enhancing the efficiency of drug delivery into the cytosol or improving the targeting of tumors relative to normal tissues. In some examples, the construct may include a polar modulator; in other examples (such as in the case of a polar drug), the construct may include a more hydrophobic modulatory to promote delivery into the cell. As used herein, modulators are used for intracellular delivery of cytotoxic molecules.

In some examples, the composition comprises 2 or more pHLIP® peptides. Exemplary constructs comprise the following structure: Peptide-L-B, in wherein "Peptide" is a first pHLIP® peptide comprising the sequence ADDQNPWRAYLDLLFPTDTLLLDLLWXA (SEQ ID NO: 1) or ADQDNPWRAYLDLLFPTDTLLLDLLWXA (SEQ ID NO: 214), "B" is a second pHLIP® peptide comprising the sequence ADDQNPWRAYLDLLFPTDTLLLDLLWXA (SEQ ID NO: 1) or ADQDNPWRAYLDLLFPTDTLLLD-LLWXA (SEQ ID NO: 214), wherein upper case "X" indicates any amino acid residue and can include lysine (Lys), cysteine (Cys), or an Azido-containing amino acid; and "L" is a polyethylene glycol linker, and each "—" is a covalent bond.

Thus in some compositions and methods, pHLIP® peptide comprises the amino acid sequence of Var3 pHLIP® sequence ADDQNPWRAYLDLLFPTDTLLLDLLWCA (SEQ ID NO: 10, ADQDNPWRAYLDLLFPTDTLLLDLL-WCA (SEQ ID NO: 212), or variations thereof. In some examples, the pHLIP® peptide comprises Var3 sequence with the amino acid sequence of ADDQNPWRAYLDLL-FPTDTLLLDLLWXA (SEQ ID NO: 215) or ADQDNP-WRAYLDLLFPTDTLLLDLLWXA (SEQ ID NO: 216), where X is a functional group for conjugation purposes. For example, the functional group is an amino acid, e.g., an amino acid selected from lysine (Lys), cysteine (Cys), Azido-containing amino acid or others (e.g., any modified amino acid for conjugation purposes).

Also within the invention is a method of augmenting an anti-tumor immune response, comprising administering to a subject a composition comprising a immuno-stimulatory

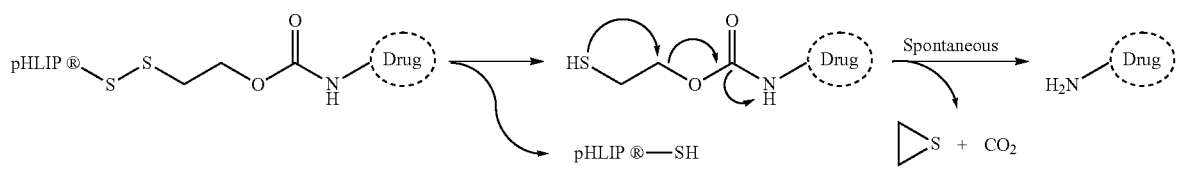

compound and a pHLIP® peptide as described above. In some examples, the immune-stimulatory compound is a polar compound such as a STING compound. For example, the subject comprises a solid tumor. The composition is administered using methods known in the art; e.g., the composition is injected directly into a tumor mass. Alternatively, the composition is systemically administered. The immuno-stimulatory compound is delivered into the cytosols of cancer cells and/or the immuno-stimulatory compound is delivered into the cytosols of macrophages within the tumor microenvironment. Because of the unique targeting aspect of the pHLIP® construct to tumors, systemic administration is possible—an important advantage of this therapy as such delivery is less invasive and traumatic to the subject to be treated.

Certain implementations comprise a formulation for a parenteral, a local, or a systemic administration comprising a pHLIP®-linker-Cargo (e.g., an immune-stimulatory compound).

Formulations comprising a pHLIP®-linker-Cargo for intravenous, subcutaneous, intraarterial, intraperitoneal, intracerebral, intracerebroventricular, intrathecal, intracardiac, intracavernous, intraosseous, intraocular, or intravitreal administration are also provided.

In an aspect, provided herein is a formulation comprising a pHLIP®-linker-Cargo for intramuscular, intradermal, transdermal, transmucosal, intralesional, subcutaneous, topical, epicutaneous, extra-amniotic, intravaginal, intravesical, nasal, or oral administration.

The present subject matter also includes a formulation for intravesical instillation comprising a pHLIP®-linker-Cargo as disclosed herein. In some embodiments, the formulation is used for the treatment of cancer (e.g., solid tumors) or autoimmune diseases.

Also provided herein is a formulation comprising a pHLIP®-linker-Cargo that comprises multiple pHLIP® peptides for systemic administration. In certain embodiments, the formulation is used for the treatment of cancer or autoimmune diseases or inflammation.

Provided herein is a method of treating cancer or autoimmune diseases or inflammation in a subject, comprising administering to the subject an effective amount of a pH-triggered compound, wherein the compound comprises an immune-stimulating cargo compound. Non-limiting examples of cancer include colon cancer, prostate cancer, breast cancer, bladder cancer, lung cancer, skin cancer, liver cancer, bone cancer, ovarian cancer, stomach cancer, pancreatic cancer, testicular cancer, and brain cancer. In some embodiments, the cancer is bladder cancer. Also included herein are methods for detecting and/or imaging diseased tissue (such as cancer tissue) in a subject comprising administering to the subject with a pHLIP®-Linker-Cargo conjugated with imaging agent (I.A.), such as I.A.-pHLIP®-Linker-Cargo. Non-limiting examples of imaging agents include fluorescent dyes or nuclear imaging agents.

The invention encompasses a method of augmenting an anti-tumor immune response, comprising administering to a subject a composition comprising an immuno-stimulatory compound and a pHLIP® peptide. For example, the subject comprises a solid tumor, e.g., cancer types described above. The composition is injected directly into a tumor mass or is systemically administered. The immuno-stimulatory compound is delivered into the cytosols of cancer cells and tumor-activated macrophages by virtue of its presence in a composition that includes both the immune-stimulatory compound and pHLIP®. For example, the composition is delivered into the cytosol of a macrophage within the diseased tissue.

Because of the presence of pHLIP® in the composition, the immuno-stimulatory compound is delivered intracellularly to induce a biological effect. For example, the biological effect of the immuno-stimulatory compound delivered in the presence of pHLIP®, e.g., in a composition that comprises both components, is at least 20%, 50%, 2-fold, 5-fold, or greater than the biological effect of the immune-stimulatory compound delivered in the absence of pHLIP® in the composition. In the absence of pHLIP®, the immuno-stimulatory compound comprises limited intracellular penetration by passive diffusion across a plasma membrane.

The composition targets the immune-stimulatory compound preferentially to a diseased tissue compared to a healthy tissue, thereby minimizing damage to the healthy tissue. For example, the composition selectively promotes intracellular delivery of the immuno-stimulatory compound to cells in diseased tissue, e.g., the composition selectively promotes intracellular delivery of the immuno-stimulatory compound into a cancer cell.

Macrophages within a tumor environment or the environment of a diseased tissue (e.g., inflamed tissue) are also acidic. Thus by virtue of the presence of pHLIP® in the composition, the composition selectively promotes intracellular delivery of the immuno-stimulatory compound into macrophages in a tumor microenvironment or into a macrophage in another diseased tissue environment. Delivery of an immune-stimulatory compound immuno-stimulatory compound delivered in the presence of pHLIP®, e.g., in a composition that comprises both components—immunostimulatory compound and pHLIP®, is at least 20%, 50%, 2-fold, 5-fold, or greater than the amount of the immuno-stimulatory compound delivered to tumor-associated macrophages in the absence of pHLIP® in the composition.

Included herein are pharmaceutical compositions comprising a pH-triggered compound and a pharmaceutically acceptable carrier.

As used herein, "effective" when referring to an amount of a compound refers to the quantity of the compound that is sufficient to yield a desired response. For example, the amount of cargo, e.g., immune-stimulatory compound yields a desired response, e.g., augmentation of an anti-tumor effect, without undue adverse side effects (such as toxicity, irritation, or allergic response) commensurate with a reasonable benefit/risk ratio when used in the manner of this disclosure.

In some embodiments, a subject is a mammal. In certain embodiments, the mammal is a rodent (e.g., a mouse or a rat), a primate (e.g., a chimpanzee, a gorilla, a monkey, a gibbon, a baboon), a cow, a camel, a dog, a cat, a horse, a llama, a sheep, a goat, or a pig. In preferred embodiments, the subject is a human.

Also within the invention is a cell, e.g., a tumor cell or a tumor-associated immune cell such as a macrophage comprising an immuno-stimulatory compound and a pHLIP® peptide as described above.

Each embodiment disclosed herein is contemplated as being applicable to each of the other disclosed embodiments. Thus, all combinations of the various elements described herein are within the scope of the invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

DETAILED DESCRIPTION

Figure 1:
FIG. 1 is a diagram of a pHLIP® construct with an immune-stimulatory compound (ISC).

The invention provides compounds, peptides with increased affinity to membrane lipid bilayers at low pH, as well as peptide insertion into and passage across membrane lipid bilayers to facilitate delivery of immuno-stimulatory compounds that promote innate immune responses. Current drugs are not cell permeable, but may enter by transporters or endocytosis.

The invention is used to target tumors with pHLIP® to specifically deliver STING agonists into cancer and immune cells and promote an immune response specifically to the targeted tissue. There are 3 major aspects: i) STING agonists (cyclic di-nucleotides or "CDNs") are mostly polar molecules, which must be delivered intracellularly to induce the immune reaction; ii) significant activation may be achieved when CDNs are delivered to macrophages within the TME; and ii) CDNs should be targeted to tumors to induce an immune response specifically within tumors only (or predominantly), otherwise the side effects will be devastating. pHLIP® guides or targets CDNs to diseased tissue for intracellular delivery of the CDNs into cancer and immune cells within tumors.

Cyclic dinucleotides are exemplary STING agonists, but other small molecules regulate innate immunity [e.g., DMXAA (also referred to as Vadimezan, ASA-404, CAS Number: 117570-53-3 (in mice) as well as Toll Like Receptor (TLR) agonists, RIG-I]. Each of these classes of immuno-stimulatory compounds train the immune system to attack tumor cells. However, each of these compounds needs to be targeted to a tumor and delivered into cells—a task that is achieved by using pHLIP® technology.

Immuno-Oncology

Immuno-oncology is an emerging field of cancer therapy that aims to activate the immune system specifically in the tumor microenvironment to induce and promote anti-tumor immune responses. Innate immunity is a critical component of host defense, and its function is based on the recognition of pathogen-associated molecular patterns (PAMPs) or danger-associated molecular patterns (DAMPs) through a set of pattern recognition receptors that stimulate the downstream signaling cascades leading to production of pro-inflammatory mediators and type I interferons (IFNs) (Takeuchi O, Akira S, 2010, Pattern recognition receptors and inflammation. Cell 140:805-820). Among intracellular immuno-stimulatory compounds are cytosolic DNA and cyclic dinucleotides recognized by Interferon Regulatory Factor (IRF) or STimulator of INterferon Genes protein (STING). STING (also known as MITA, MPYS, ERIS and TMEM173) is a protein localized predominantly on the endoplasmic reticulum membrane (Ishikawa H, Barber GN, 2008, STING is an endoplasmic reticulum adaptor that facilitates innate immuno signaling. Nature 455:674-678). The ability of STING to induce the production of type I IFNs is used to promote an immune response (Woo SR, Fuertes MB, Corrales L et al, 2014, STING-dependent cytosolic DNA sensing mediates innate immuno recognition of immunogenic tumors. Immunity 41:830-842). STING agonists are cyclic dinucleotides (CDNs) such as cyclic di-GMP (guanosine 5'-monophosphate) (CDG), cyclic di-AMP (adenosine 5'-monophosphate) (CDA), and cyclic GMP-AMP (cGAMP).

To activate the STING pathway and to promote and to induce the immune system for treatment of tumors, STING agonists are delivered to tumors and translocated across membrane into cancer and immune cells using the compositions and methods described herein.

STING in a Tumor Microenvironment

Direct activation of STING in the tumor microenvironment leads to potent and systemic tumor regression and immunity (Corrales et al., Cell Rep. 2015 May 19; 11(7): 1018-1030). Tumor-initiated T cell priming is dependent on IFN-β production by tumor-resident dendritic cells. IFN-β expression is dependent upon activation of the host STING pathway. The highest expression of IFN within tumors upon stimulation with STING agonist was observed in tumor-associated macrophages (TAMs). Four different cell populations from pre-established B16 tumors were sorted: DCs (CD45+ CD11c+ MHCII+), macrophages (CD45+ CD11b+ F4/80+ MHC-II+), T cells (CD45+ CD3+), and endothelial cells (CD45– CD31+). Sorted cells were then stimulated ex vivo with ML RR-S2 CDA (also referred to asDithio-(Rp, Rp)-2',3'-CDA sodium salt; CAS Number: 1638241-89-0) or DMXAA. All subsets expressed IFN-β upon stimulation with the STING agonists. Expression in macrophages was highest, followed by DCs, which were both higher as compared with lymphocytes and endothelial cells.

Synthetic cyclic dinucleotide (CDN) derivatives activate STING alleles, and intratumoral injections of STING agonists such as CDNs are useful as cancer therapeutics; however, their use is hampered by their poor intracellular penetration by passive diffusion across a cell's plasma membranes. Delivery of STING agonists such as CDNs to cells by pHLIP®, e.g., in the form of a composition comprising both a STING agonist and a pHLIP®, significantly increases the introduction/delivery of the STING agonist across the plasma membrane and into the cytosol of a TAM.

pHLIP® Delivery of STING Agonists

The invention provides compositions and methods to target tumors with pHLIP® to specifically deliver STING agonists into cancer and immune cells and promote an immune response specifically to the target tissue. As described above, STING agonists (e.g., cyclic di-nucleotides, "CDNs") are mostly polar molecules, which must be delivered intracellularly to induce the immune reaction. CDNs should be targeted to tumors to induce immune response specifically within tumors only (or predominantly) to avoid or minimize adverse side effects. Intra-tumoral direct injections of CDN can be used. However with pHLIP®, systemic administration is possible—a significant advantage over previous methods.

The methods described herein using pHLIP®-CDN constructs lead to targeted intracellular delivery of CDN into cancer and immune cells within tumors. Systemic or intra-tumoral injection of pHLIP®-CDN can be used.

pHLIP® Constructs

General representations of pHLIP® compounds comprising pHLIP® peptide and an immuno stimulator cargo molecule are shown in FIGS. 1-16 and described below.

FIG. 1 shows an immuno stimulator cargo (ISC) molecule linked to a pHLIP® peptide:

The combinations shown in FIGS. 2-12 are variations of the scheme shown in FIG. 1. Exemplary constructs include cGAMP cyclic compounds conjugated to pHLIP®.

Figure 2A:
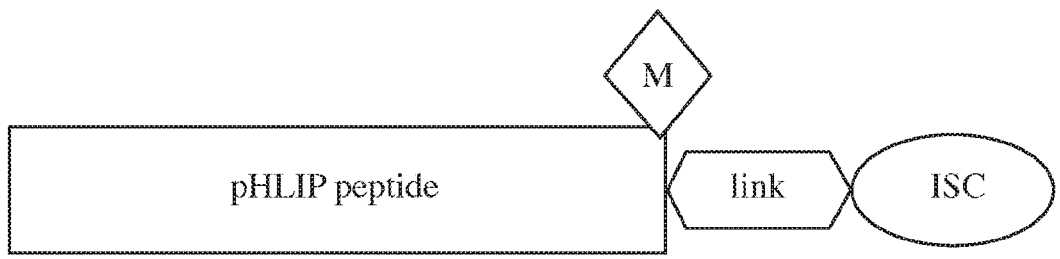
FIGS. 2A-2C are diagrams of pHLIP® constructs with an ISC and a modulator (M) molecule. The modulator could be attached to the pHLIP® peptide (FIG. 2A), linker (FIG. 2B) or ISC (FIG. 2C).
Figure 2B:
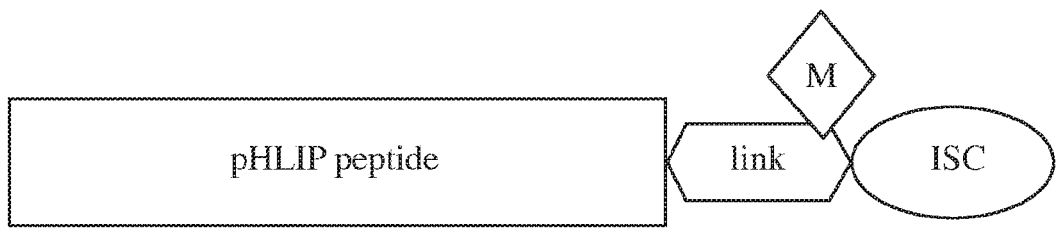
Figure 2C:
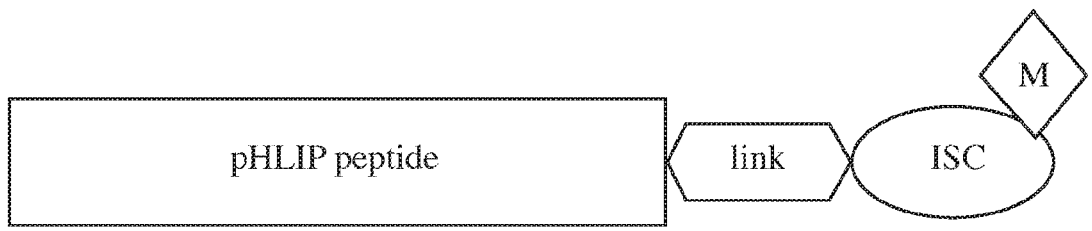

One or more modulator molecules (M) are optionally attached to the pHLIP® peptide membrane-inserting end to promote better translocation of an immuno stimulator cargo molecule (FIG. 2). A modulator molecule(s) can be a polar molecule to enhance intracellular delivery of hydrophobic and moderately hydrophobic immuno stimulator cargo molecules. If the cargo is polar (Log P<–0.4), the hydrophobic modulator will increase the Log P of [cargo-modulator] (Log P>–0.4). Alternatively, a modulator molecule(s) can be a non-polar molecule to enhance intracellular delivery of polar immuno stimulator cargo molecules. If the cargo is hydrophobic Log P>2.5, the polar modulator will decrease Log P of [cargo-modulator] (Log P<2.5). Non-limiting examples of modulators are fatty acids, PEG polymers, hydrophobic fluorescent dyes, cyclic peptides. Modulators can alter (increase or decrease) the polarity of the construct/composition by 1%, 5%, 10%, 25%, 50% 75%, 2-fold, 3-fold, 5-fold, 10 fold or more compared to the construct/composition that lacks a modifier.

Figure 3:
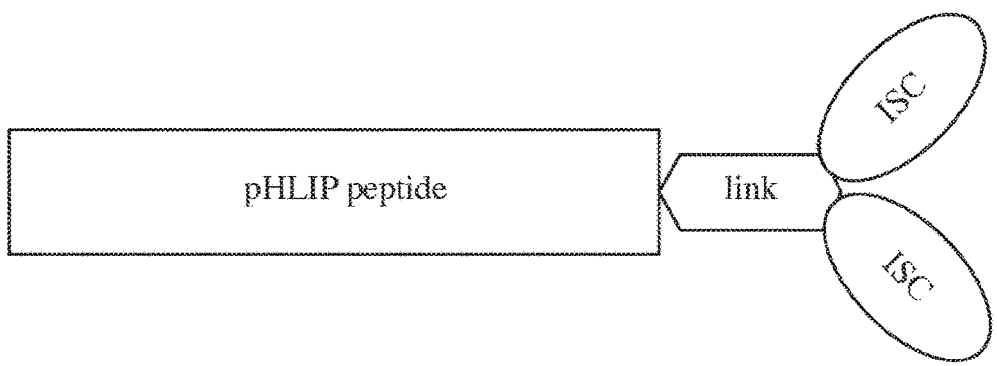
FIG. 3 is a diagram of a pHLIP® construct with 2 (or more) ISCs.

FIG. 3 shows multiple immuno stimulator cargo molecules linked to a single pHLIP® peptide.

Figure 4A:
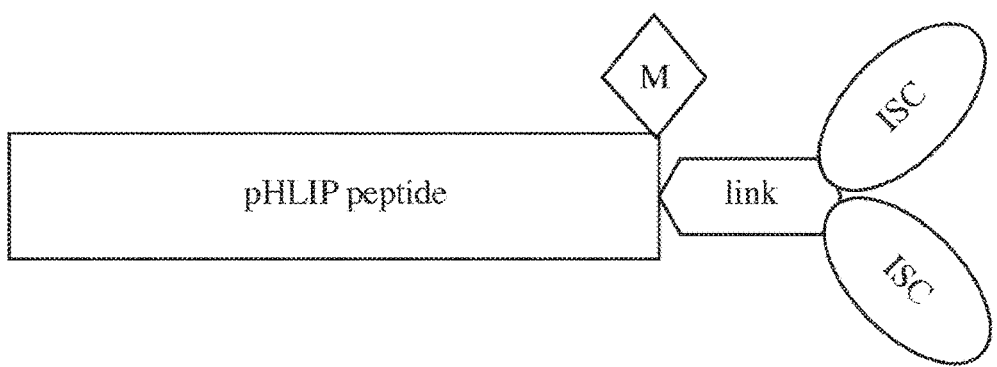
FIGS. 4A-4C are diagrams of pHLIP® constructs with 2 (or more) ISCs and a M molecule. The modulator could be attached to pHLIP® peptide (FIG. 4A), linker (FIG. 4B) or ISC (FIG. 4C).
Figure 4B:
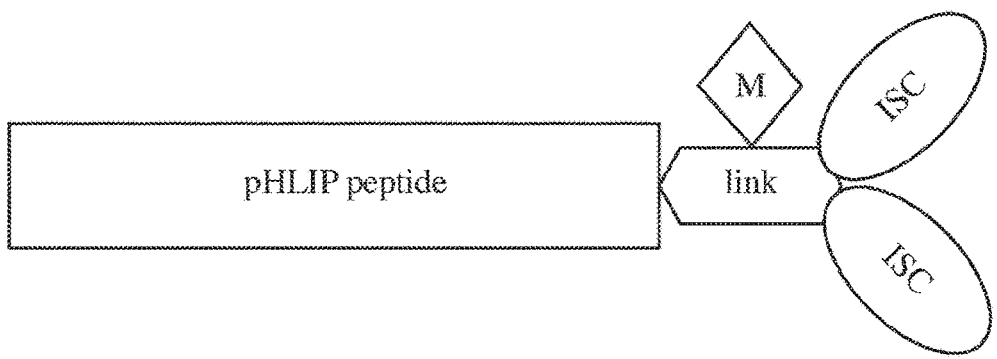
Figure 4C:
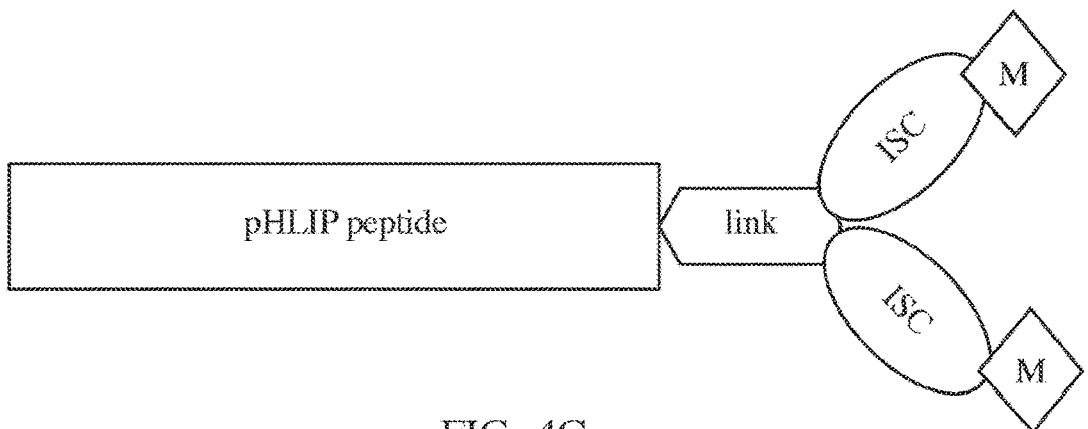
Figure 5:
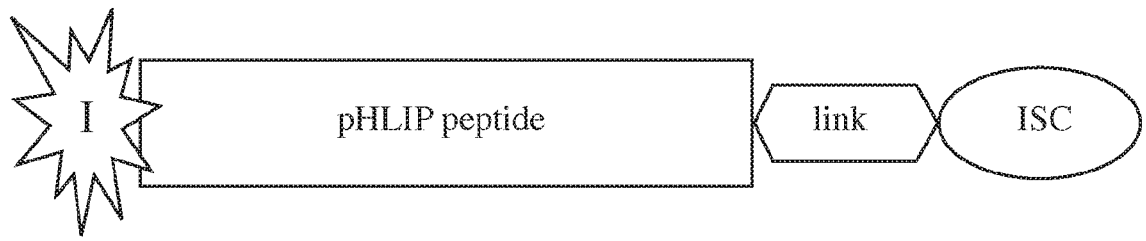
FIG. 5 is a diagram of a pHLIP® construct with an ISC and an imaging agent at the membrane non-inserting end.
Figure 6A:
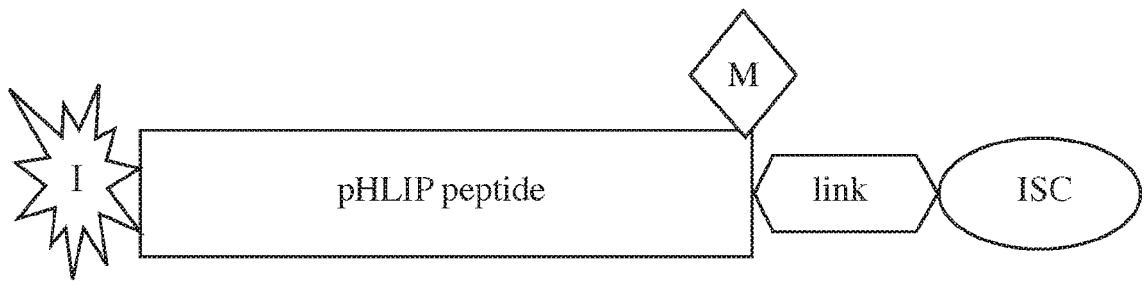
FIGS. 6A-C are diagrams of pHLIP® constructs with an ISC and M molecule and an imaging agent at the membrane non-inserting end. The modulator could be attached to pHLIP® peptide (FIG. 6A), linker (FIG. 6B) or ISC (FIG. 6C).
Figure 6B:
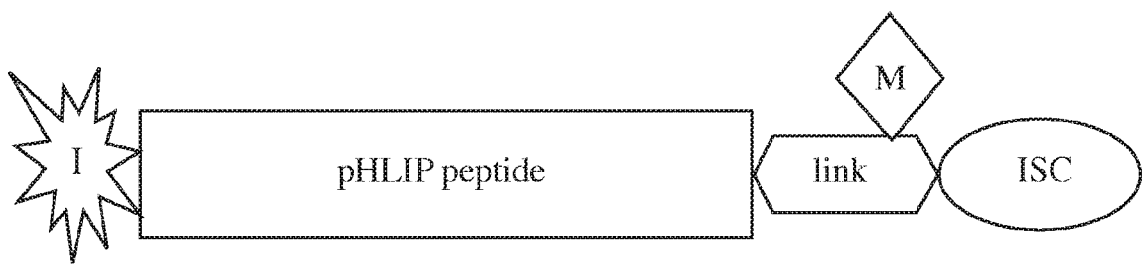
Figure 6C:
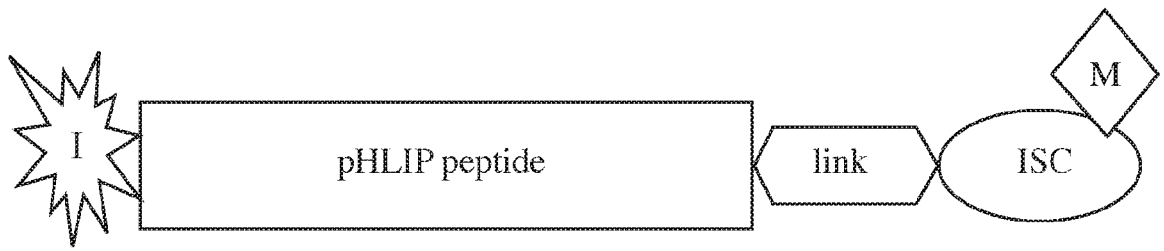
Figure 7:
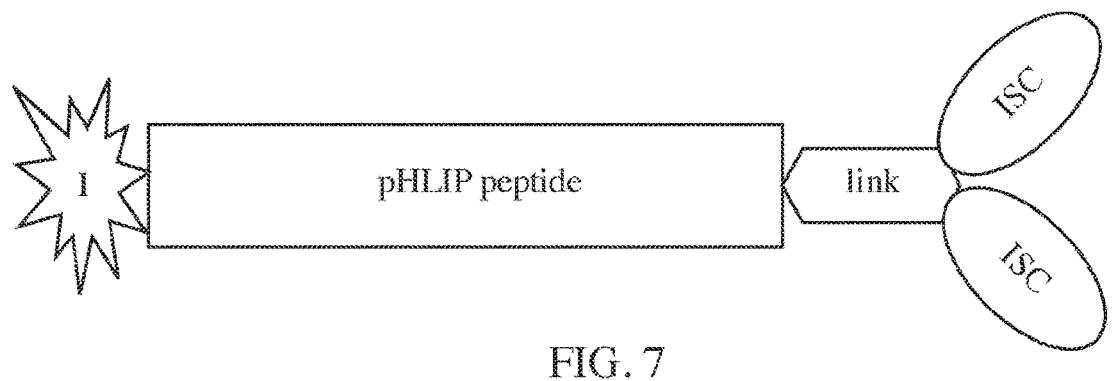
FIG. 7 is a diagram of a pHLIP® construct with multiple ISCs and an imaging agent at the membrane non-inserting end.
Figure 8A:
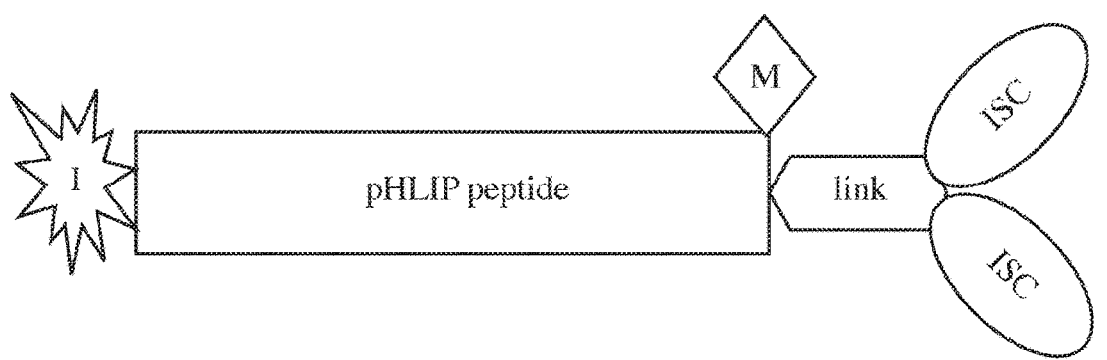
FIGS. 8A-C are diagrams of pHLIP® constructs with multiple ISCs and M molecule and an imaging agent at the membrane non-inserting end. The ISCs can be the same or different. The modulator could be attached to pHLIP® peptide (FIG. 8A), linker (FIG. 8B) or ISC (FIG. 8C).
Figure 8B:
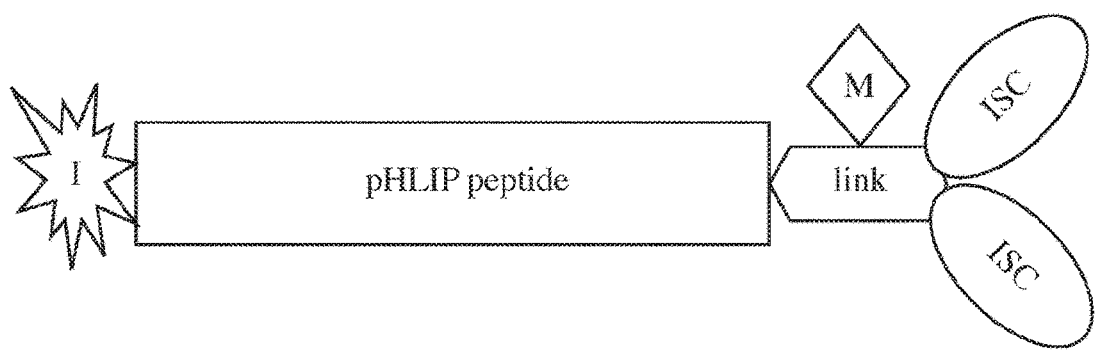
Figure 8C:
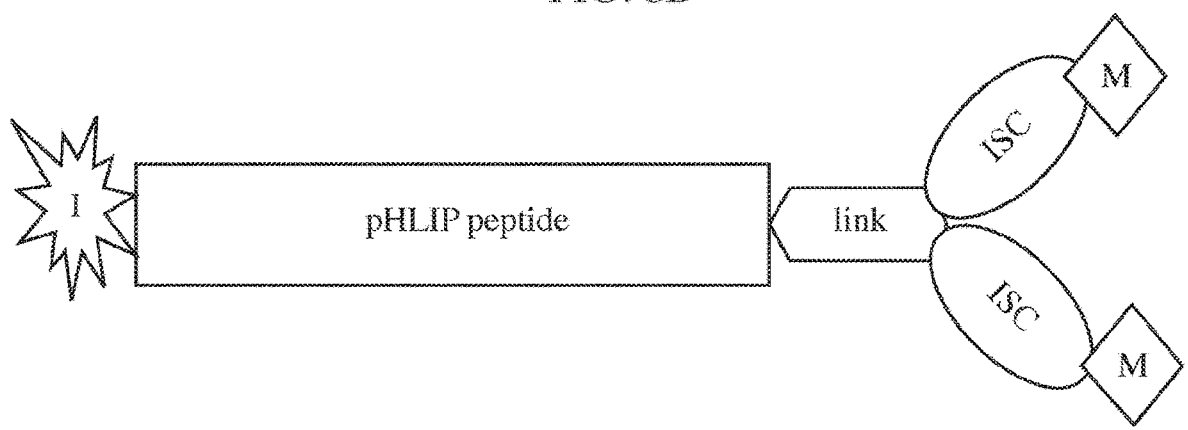

FIG. 4 shows multiple immuno stimulator cargo molecules linked to a single pHLIP® peptide with one or more modulator molecules.

FIGS. 5-8 depict pHLIP® compounds that can carry one or more imaging agents (I) (or other molecules) at pHLIP® peptide membrane-non-inserting end.

Figure 9:
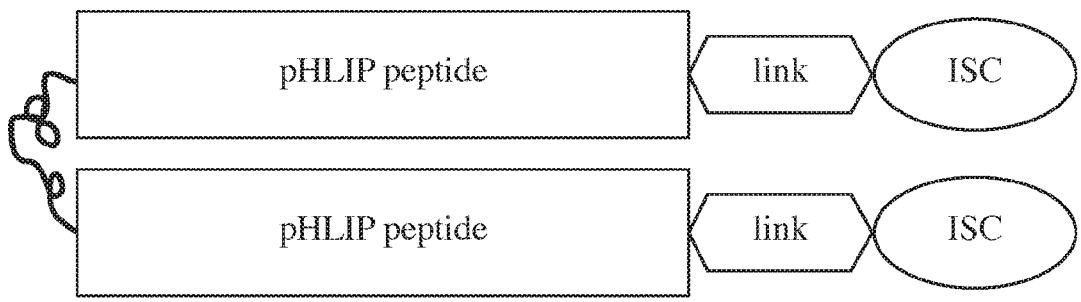
FIG. 9 is a diagram of two or more pHLIP® peptides connect to each other by a PEG polymer (or any other polymer—shown by purple color) with an ISC linked together via a linker molecule.
Figure 10A:
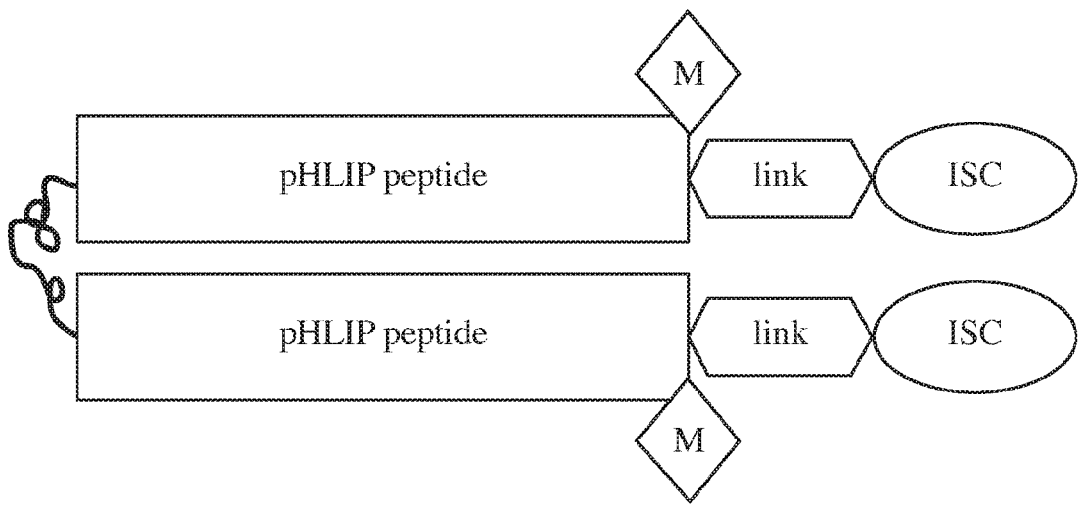
FIGS. 10A-C are diagrams of exemplary pHLIP® constructs with two or more pHLIP® peptides connect to each other by PEG polymer (or any other polymer—shown by purple color) with an ISC linked together via a linker molecule. The modulator could be attached to pHLIP® peptide (FIG. 10A), linker (FIG. 10B) or ISC (FIG. 10C).
Figure 10B:
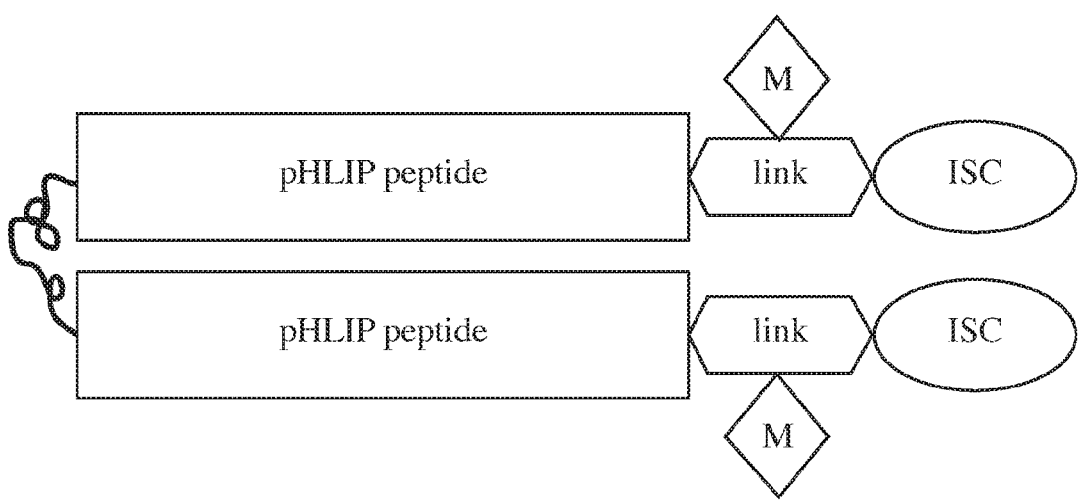
Figure 10C:
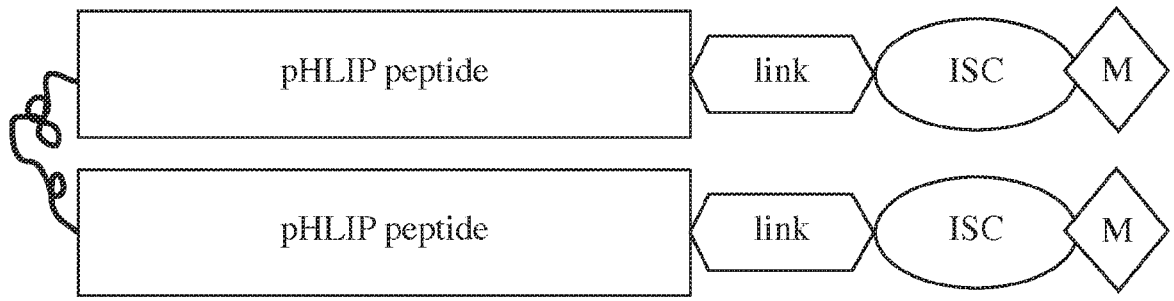
Figure 11:
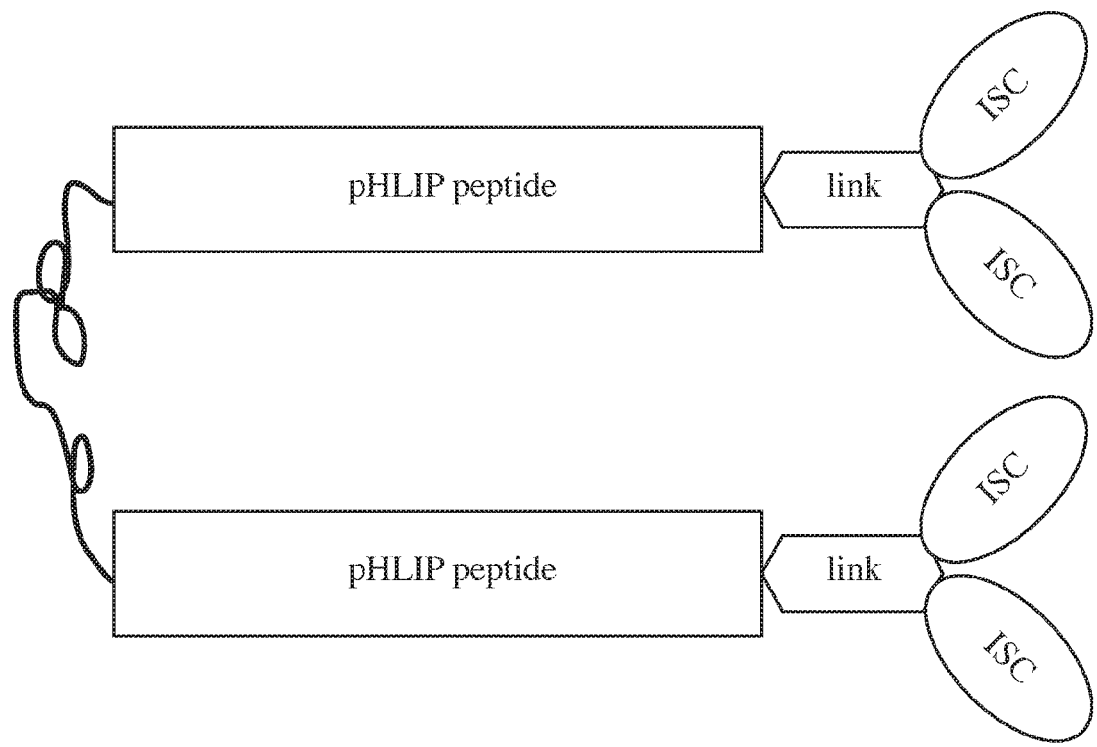
FIG. 11 is a diagram of an exemplary pHLIP® construct with two or more pHLIP® peptides connect to each other by PEG polymer (or any other polymer—shown by purple color) with an ISC linked together via a linker molecule.
Figure 12A:
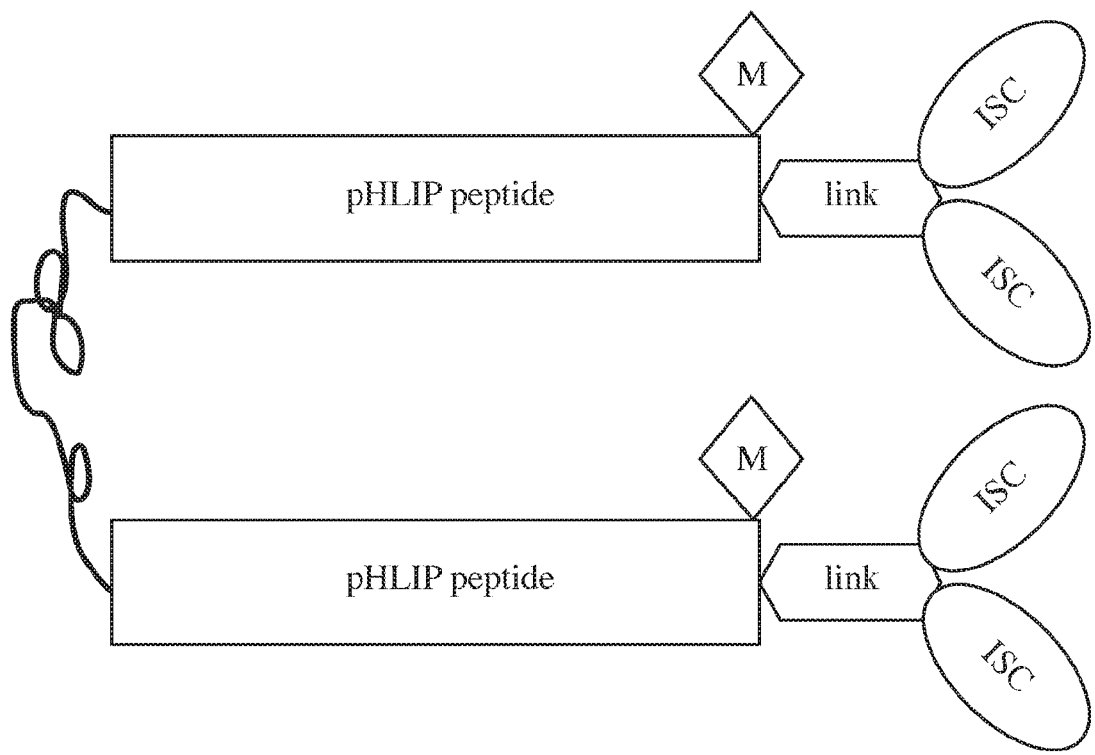
FIGS. 12A-C are diagrams of exemplary pHLIP® constructs with two or more pHLIP® peptides connect to each other by PEG polymer (or any other polymer—shown by purple color) with an ISC linked together via a linker molecule. The modulator could be attached to pHLIP® peptide (FIG. 12A), linker (FIG. 12B) or ISC (FIG. 12C).
Figure 12B:
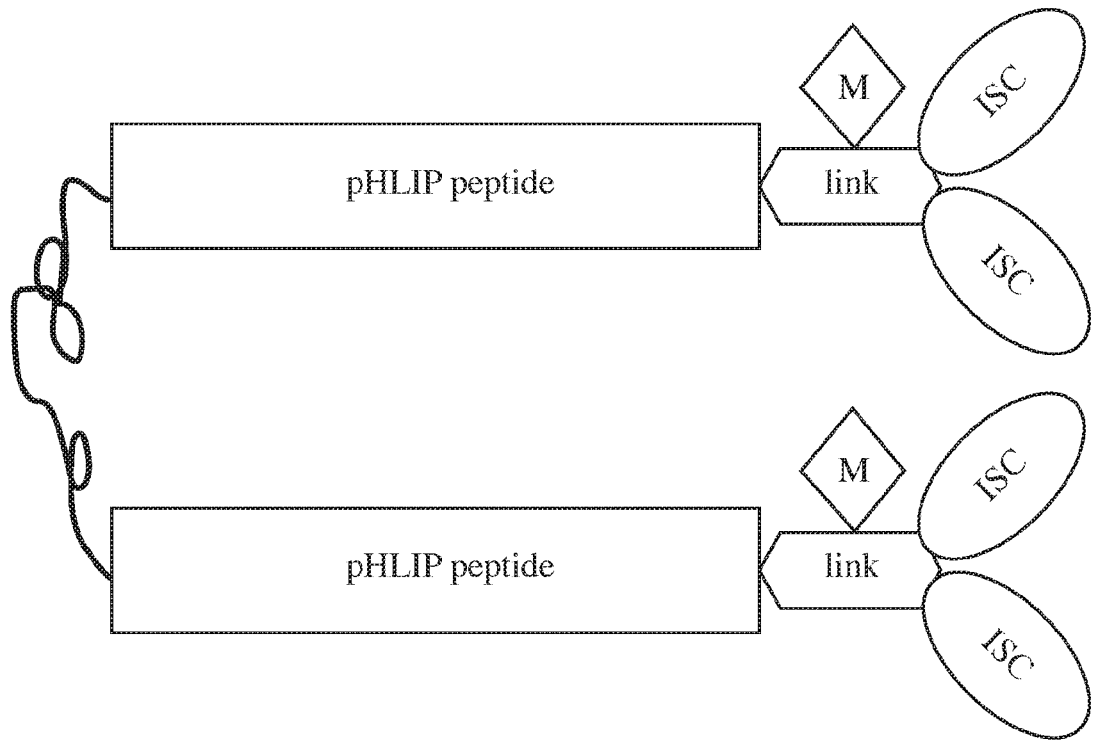
Figure 12C:
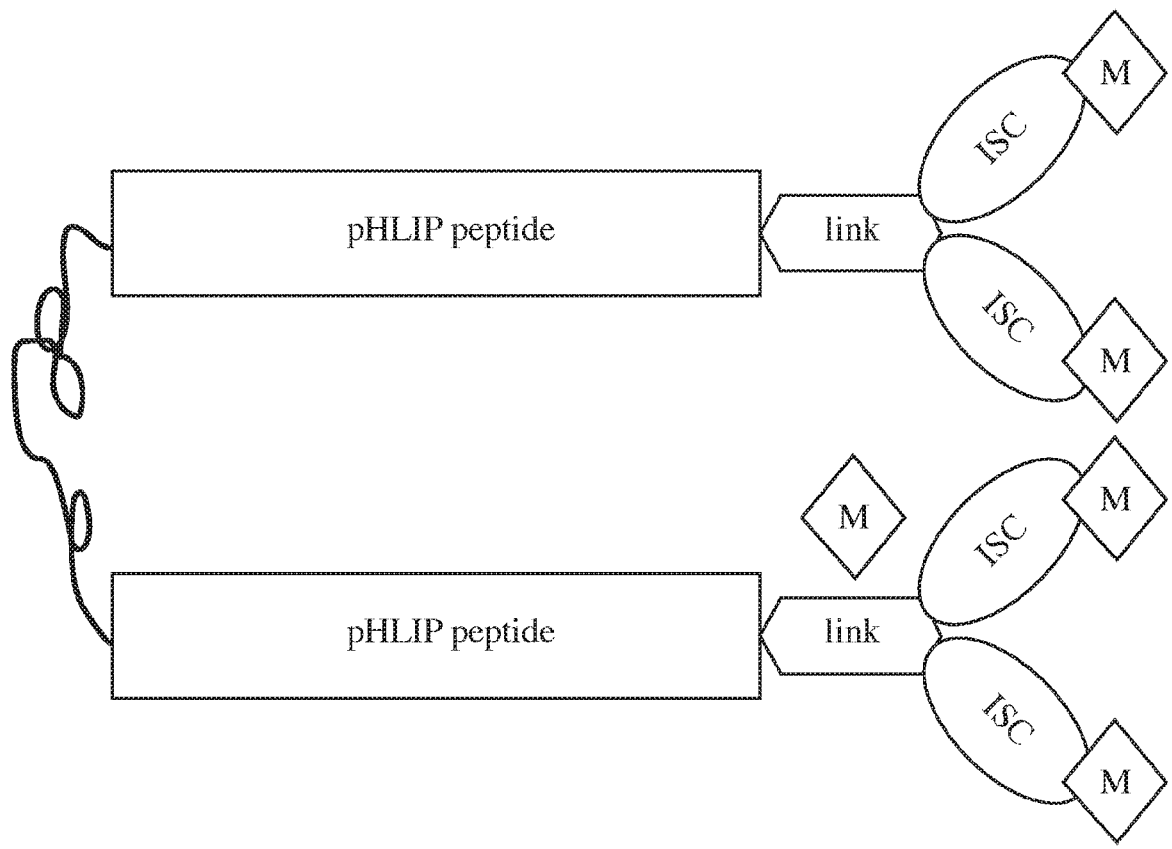
Figure 13A:
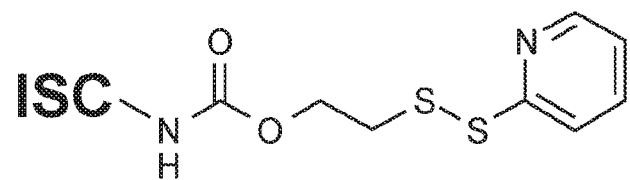
FIG. 13A is a structure of an exemplary self-immolating linker with immuno-stimulatory compound (ISC) for S-S exchange with Cys residue of pHLIP® peptide.
Figure 13B:
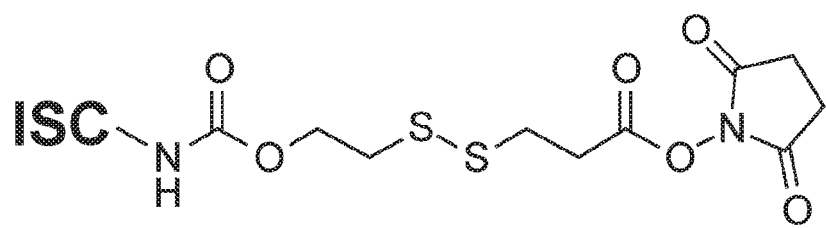
FIG. 13B is a structure of an exemplary self-immolating linker with immuno-stimulatory compound (ISC) for conjugation with Lys residue at pHLIP® peptide.

FIG. 9 shows two or more pHLIP® peptides with an immuno stimulator cargo linked together via linker molecule Exemplary constructs include a Var3 pHLIP® sequence ADDQNPWRAYLDLLFPTDTLLLDLLWCA (SEQ ID NO: 10), ADQDNPWRAYLDLLFPTDTLLLDLLWCA (SEQ ID NO: 212), or variations thereof, e.g., sequences provided in the tables below and in references cited herein (and incorporated by reference).

Figure 14A:
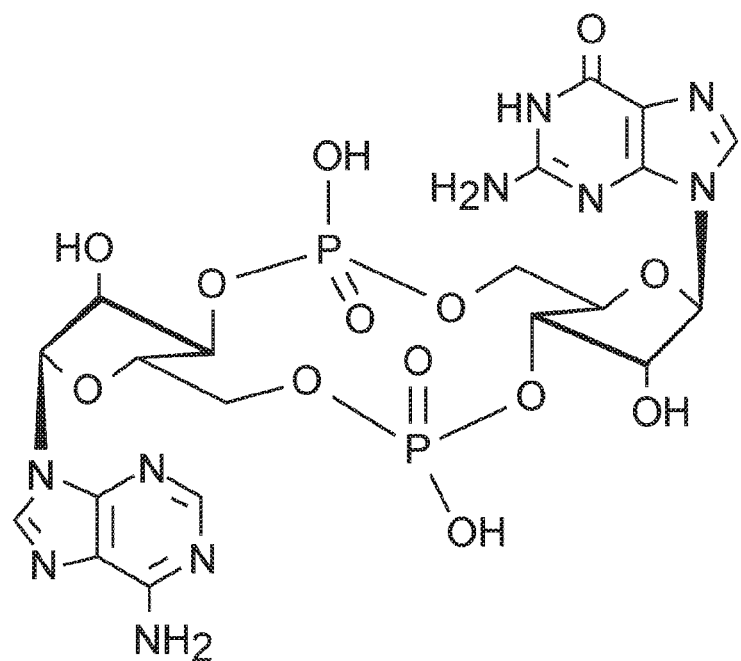
FIG. 14A is a chemical structure of c-GAMP (ADU-S100 (MIW815)) cyclic dinucleotide (CDN) GMP-AMP, agonist (activator) of STING.
Figure 14B:
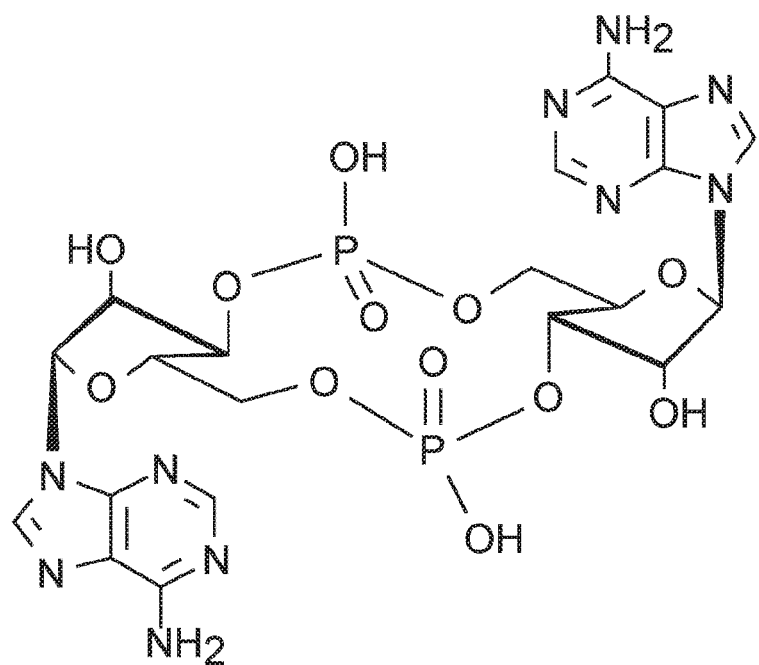
FIG. 14B is a chemical structure of c-diAMP cyclic dinucleotide (CDN) di-AMP, agonist (activator) of STING.
Figure 14C:
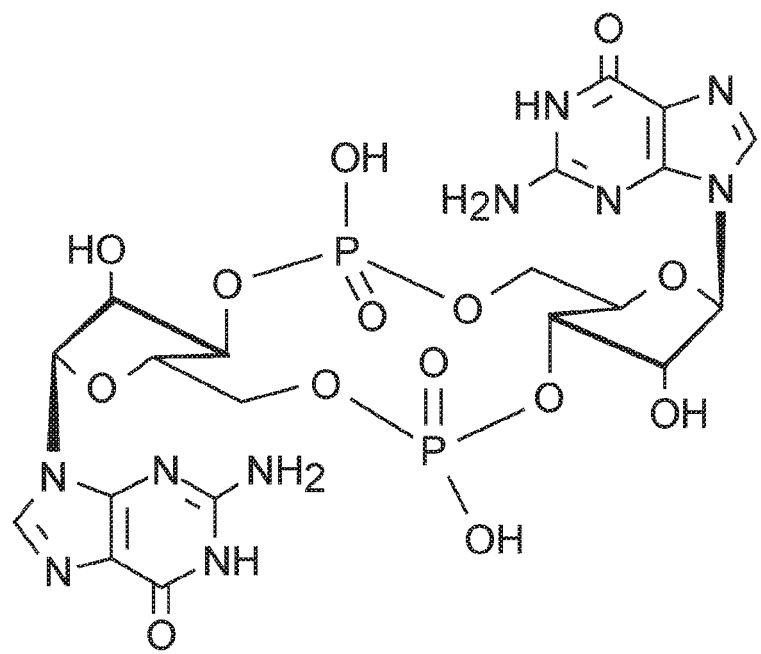
FIG. 14C is a chemical structure of c-diGMP cyclic dinucleotide (CDN) di-GMP, agonist (activator) of STING
Figure 15A:
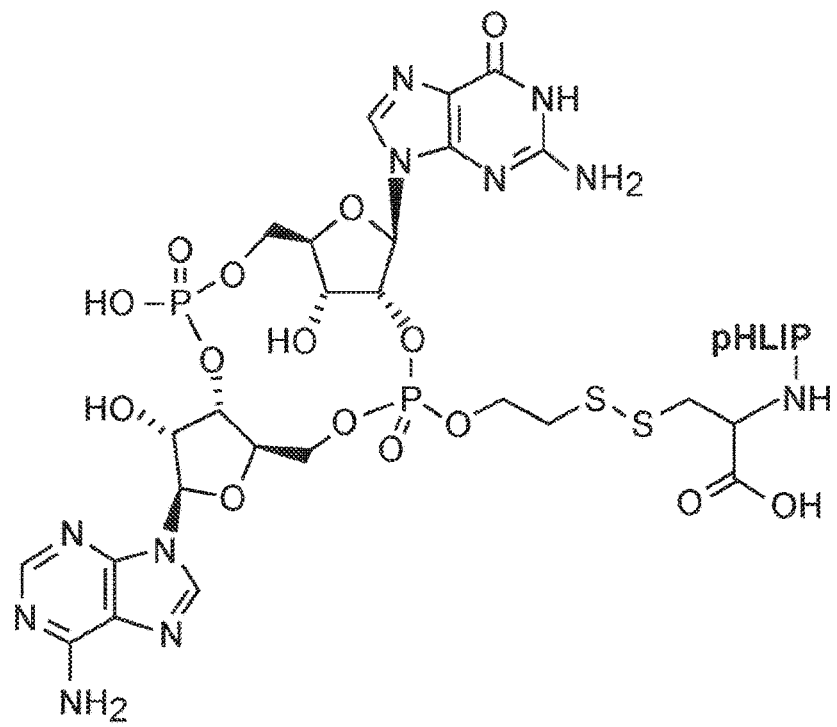
FIG. 15A is a chemical structure of a pHLIP-S-S-cGAMP in which cGAMP is coupled with Cys at pHLIP peptide via self-immolating linker.
Figure 15B:
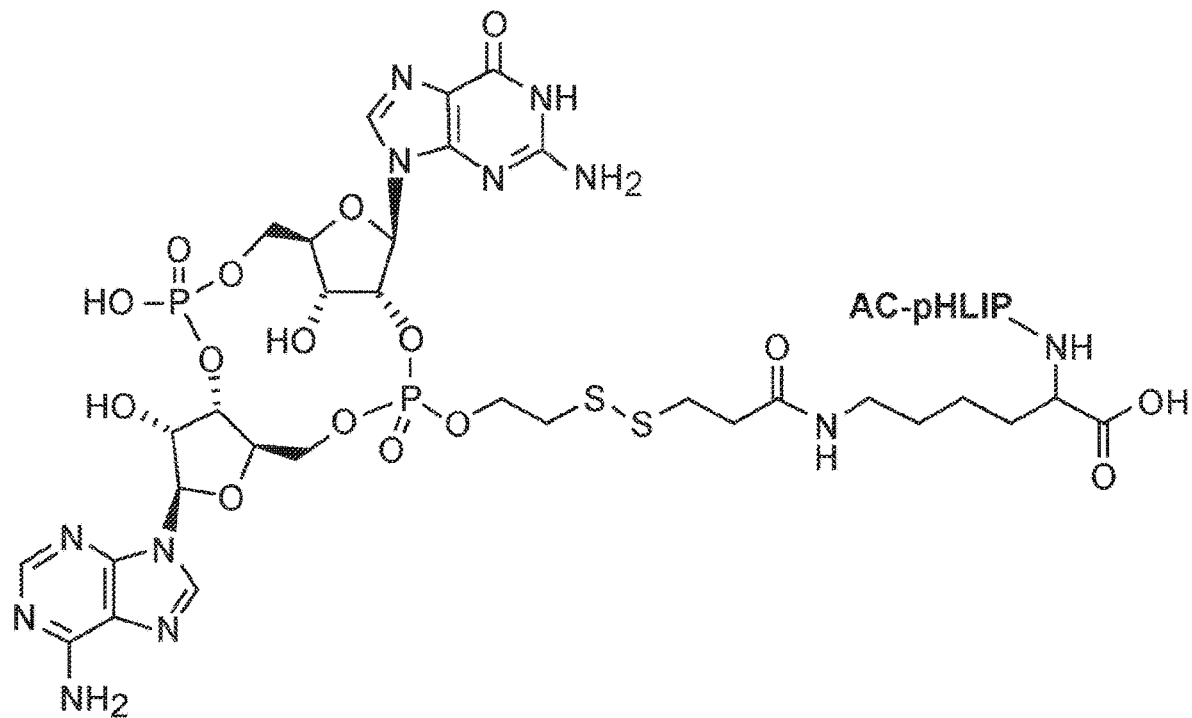
FIG. 15B is a chemical structure of a pHLIP-S-S-cGAMP in which cGAMP is coupled with Lys at acetylated pHLIP peptide via self-immolating linker.

In preferred embodiments, the cargo is an immune-stimulatory molecule (see, e.g., FIG. 14A-14C). An immuno-stimulatory cargo molecule can target Toll-like Receptors (TLRs), RIG-I-like Receptors (RLRs), or Stimulator of Interferon Genes (STING) or other regulators of the immune response. For example, an immuno-stimulatory cargo molecule binds STING, e.g., an immuno-stimulatory cargo molecule is a STING agonist, e.g., an immuno-stimulatory cargo molecule is cyclic dinucleotide. Non-limiting examples include cyclic di-GMP, cyclic di-AMP and cyclic GMP-AMP, and their derivatives. Exemplary cyclic GMP compound include c[8-AET-G(2',5')pA(3',5')p] (Biolog Cat. No. C 175), c[3'-AHC-G(2',5')pA(3',5')p] (Biolog Cat. No. C 191), and c[G(2',5')p-2'-AHC-A(3',5')p] (Biolog Cat. No. C 192), each of which is commercially available from BIOLOG Life Science Institute, Bremen, Germany. Other examples include their parent compounds: c[G(2',5')pA(3', 5')p], c[G(2',5')pA(3',5')p], and c[G(2',5')pA(3',5')p], respectively.

The cargo(s) is linked to pHLIP® peptide(s) via cleavable link(s). For example, the cleavable link can be a disulfide bond, or acid-liable link. In other examples, the cleavable link is a self-immolating link, which allows to release cargo molecule in its non-modified form.

STING Agonists

Immunotherapy includes a number of strategies that harness the immune system to help treat disease. Immunotherapy for cancer relies on the activation of specific immune system cells, e.g., T cells. Cancer drugs called immune checkpoint inhibitors act by removing the brakes imposed on T cells by tumors or by the body's natural mechanisms for limiting their activation to prevent autoimmune disease.

A key player in the body's innate immune response is the STING pathway. The STING pathway was first discovered as a response to viral infections; it senses viral DNA in the cytosol of infected cells. Activation of the protein interferon, a very potent immune system stimulator, is a hallmark of this pathway, which also plays a role in cancer treatment. STING ligands are described in the art, e.g., in U.S. Pat. Nos. 10,045,961; 10,011,630; 9,834,545; 9,642,830; 9,415,045 (each of which is hereby incorporated by reference.) For example, U.S. Pat. No. 10,045,961 describes exemplary STING agonists that include flavonoids, wherein suitable flavonoids include, but are not limited to, 10-(carboxymethyl)-9(10H)acridone (CMA), 5,6-Dimethylxanthenone-4-acetic acid (DMXAA), methoxyvone, 6, 4'-dimethoxyflavone, 4'-methoxyflavone, 3', 6'-dihydroxyflavone, 7, 2'-dihydroxyflavone, daidzein, formononetin, retusin 7-methyl ether, xanthone, or any combination thereof, which are useful in the compositions and methods described herein.

STING acts as a sensor of cytosolic DNA. Bacteria and virus or self-derived DNA in the cytosol activates the STING pathway and promotes the production of type I interferons (IFN-alpha and IFN-beta). STING also participates in cell death signaling through its association with MHC-II and the ERK pathway. STING interacts with DExD/H-Box Helicase 58 (DDX58) DDX58/RIG-I, mitochondrial antiviral-signaling protein (MAVS), signal sequence receptor unit 2 (SSR2), ring finger protein 5 (RNF5), Tripartite Motif Containing 56 (TRIM56), TANK-binding kinase 1 (TBK1), Interferon Induced Protein With Tetratricopeptide Repeats 1 (IFIT1), and Interferon Induced Protein With Tetratricopeptide Repeats 2 (IFIT2). It localizes to the cytoplasm and membranes of the cell, endoplasmic reticulum (ER), and mitochondria; however, in response to DNA stimulation, it translocates to the perinuclear region and interacts with TBK1 kinase. STING's phosphorylation by TBK1 at Ser-358 results in STING activation. STING executes its role by sensing and binding cyclic di-GMP/c-di-GMP and cyclic GMP-AMP/cGAMP. This binding results in the activation of nuclear factor kappa-light chain enhancer of activated B cells (NF-κβ) and interferon regulator factor 3 (IRF3) transcriptional signaling pathways leading to the induction of Type I interferon response.

The U.S. Food and Drug Administration (FDA) has approved several immune checkpoint drugs for the treatment of various cancers. These drugs target proteins involved in activating the T cell response: programmed death protein 1 (PD-1), programmed death protein ligand 1 (PD-L1), and Cytotoxic T-Lymphocyte Associated Protein 4 (CTLA4). Many clinical trials are testing drugs that target other immune checkpoint proteins (tumor necrosis factor receptor superfamily, member 4 (also referred to as TNFRSF4 or OX40), CD276 (Cluster of Differentiation 276 (also referred to as CD276 or B7-H3), and (lymphocyte activation gene 3 (LAGS), to name just a few), but no notable successes have been reported so far.

T cells are major players in the adaptive immune system—an arm of the immune system that "adapts" or educates itself to recognize highly specific targets (like mutant proteins in cancer cells or specific molecules found on viruses or other pathogens). This adaptive response takes time to mount. In contrast, a more primitive arm of the immune system, the innate immune response, is not very specific, but provides very fast recognition of many kinds of pathogens, including viruses, bacteria, and parasites.

The innate response also plays an integral role in the development of the adaptive response. The innate response involves cells (macrophages and dendritic cells) that may present specific "foreign" molecules to T cells and initiate a specific, adaptive, response. In patients with cancer, the problem is that the adaptive immune response is not activated or inadequately activated.

In the STING pathway, a specific protein called cyclic GMP-AMP Synthase (cGAS) recognizes DNA in the cytosol of an infected cell. cGAS produces a molecule called cGAMP, which activates the protein STING, for which the entire pathway is named STING activates dendritic cells or macrophages, which in turn leads to the activation of the adaptive immune response involving T cells. The STING pathway is also involved in the efficacy of radiation as cancer treatment; the nuclei of cancer cells may break down during radiation, releasing DNA and activating the STING pathway.

Drugs that activate STING or STING agonists include those with a ring-shaped molecular structure known, e.g., cyclic dinucleotide such as cGAMP or engineered agonist molecules that have been shown to activate production of interferon.

Systemic activation of interferon may cause strong inflammatory and autoimmune responses. A significant advantage of the constructs/compositions described herein is that they mediate targeted delivery to tumor cells and/or immune cells within a tumor mass, thereby avoiding or minimizing severe systemic effects. Exemplary STING agonists include ADU-S100 (also referred to as: MIW815, NVP-MIW815, ADUS100) and MK-1454 (Merk—clinical trials identifier NCT03010176).

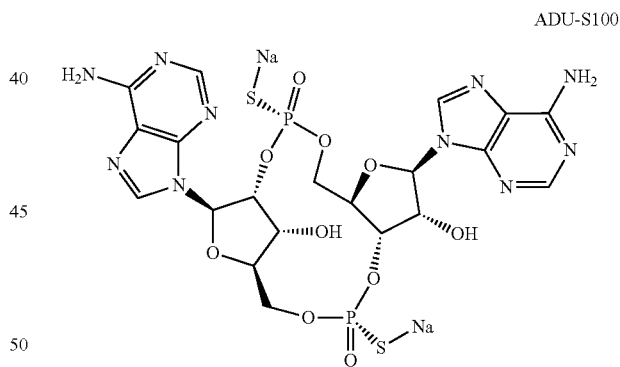

ADU-S100

As described above, STING is a central mediator of innate immunity. When stimulated, STING induces the expression of type I interferon, cytokines and T cell recruitment factors that result in the activation of macrophages and dendritic cells, innate effector cells such as natural killer (NK) cells, and priming of tumor-specific T cells. Cyclic dinucleotides (CDNs) and the xanthenone derivative DMXAA bind to and activate STING (Stimulator of interferon genes), leading to a potent type I IFN response.

Thus, CDNs are potent inducers of the innate immune response and are useful as vaccine adjuvants. A synthetic cyclic dinucleotide (CDN) and agonist of STING, has immunoactivating and antineoplastic activities. Upon intratumoral (IT) administration, STING agonist MK-1454 binds to STING and activates the STING pathway, which promotes IKK-related kinase TANK-binding kinase 1 (TBK1) signaling and activates nuclear factor-kappa B (NF-kB) and interferon regulatory factor 3 (IRF3) in immune cells in the tumor microenvironment, thereby leading to the production of pro-inflammatory cytokines, including interferons and a CTL-mediated immune response against tumor cells and tumor cell lysis.

Toll-Like Receptors

Proteins known as toll-like receptors (TLRs), of which there are 10 different types, are found on the surface and inside of immune cells such as macrophages. TLRs are located on the plasma membrane of cells with the exception of TLR3, TLR7, TLR9 which are localized in the endosomal compartment. Macrophages are immune system cells that not only destroy incoming pathogens, but also may alert the adaptive immune system to an infection. For example, TLR9 recognizes a motif in DNA sequences known as CpG, which is found far more frequently in bacterial than in our own DNA.

When a TLR9 agonist such as a DNA molecule enriched in CpG, is injected into a tumor, rapid activation of macrophages and dendritic cells (DCs) that express TLR9 occurs. The macrophages may directly destroy the infected cells, but, together with DCs, they alert T cells residing in the tumor or draining lymph nodes, and thus promote an adaptive immune response.

Exemplary TLR9 agonists include SD-101, IMO-2125, MGN1703 (Lefitolimod), and DV281. Other TLR agonists, e.g., activators of TLR7/8, include NKTR-262 and MEDI9197. Use of pHLIP® peptides in the compositions or constructs described herein facilitate delivery of TLR agonists to tumors.

pHLIP® Peptides

An example of a wild type (WT) is AEQNPIYWARYADWLFTTPLLLLDLALLVDADEGT (SEQ ID NO: 3) in which AEQNPIY (SEQ ID NO: 4) represents a flanking sequence, WARYADWLFTTPLLLLDLALLV (SEQ ID NO: 5) represents a membrane-inserting sequence, and DADEGT (SEQ ID NO: 6) represents a flanking sequence Other exemplary pHLIP® peptides are shown in the Tables below.

TABLE 1

| Name | Sequence | SEQ ID NO: |
|---|---|---|
| Var3-1a | ADQDNPWRAYLDLLFPTDTLLLDLLWCA | SEQ ID NO: 212 |
| Var3-1b | ADQDNPWRAYLDLLFPTDTLLLDLLWKA | SEQ ID NO. 213 |
| WT-1 | GGEQNPIYWARYADWLFTTPLLLLDLALLVDADEGT | SEQ. ID NO. 7 |
| WT-2 | AEQNPIYWARYADWLFTTPLLLLDLALLVDADEGT | SEQ. ID NO. 8 |
| WT-Cys1 | AAEQNPIYWARYADWLFTTPLLLLDLALLVDADEGTCG | SEQ. ID NO. 9 |
| WT-Cys2 | Ac-AEQNPIYWARYADWLFTTPLLLLDLALLVDADEGCT | SEQ ID NO: 211 |
| WT-Cys3 | GGEQNPIYWARYADWLFTTPLLLLDLALLVDADEGTCG | SEQ. ID NO. 11 |
| Cys-WT1 | Ac-ACEQNPIYWARYADWLFTTPLLLLDLALLVDADEGTG | SEQ. ID NO. 12 |
| Var0-NT | ACEQNPIYWARYADWLFTTPLLLLDLALLVDADEGT | SEQ. ID NO. 13 |
| Lys-WT1 | AKEQNPIYWARYADWLFTTPLLLLDLALLVDADEGT | SEQ. ID NO. 14 |
| Lys-WT2 | Ac-AKEQNPIYWARYADWLFTTPLLLLDLALLVDADEGTG | SEQ ID NO: 15 |
| WT-KC | AAEQNPIYWARYADWLFTTPLLLLDLALLVDADEGTKCG | SEQ. ID NO. 16 |
| K-WT-C | AKEQNPIYWARYADWLFTTPLLLLDLALLVDADECT | SEQ. ID NO. 17 |
| N-pHLIP® | ACEQNPIYWARYANWLFTTPLLLLNLALLVDADEGTG | SEQ. ID NO. 18 |
| N-pHLIP®-b | ACEQNPIYWARYANWLFTTPLLLLNLALLVDADEGT | SEQ ID NO: 19 |
| K-pHLIP® | ACEQNPIYWARYAKWLFTTPLLLLKLALLVDADEGTG | SEQ. ID NO. 20 |
| NNQ | GGEQNPIYWARYADWLFTTPLLLLDLALLVNANQGT | SEQ. ID NO. 21 |
| D25A | AAEQNPIYWARYADWLFTTPLLLLALALLVDADEGT | SEQ. ID NO. 22 |
| D25A-KC | Ac-AAEQNPIYWARYADWLFTTPLLLLELALLVDADEGTKCG | SEQ ID NO: 23 |
| D14A | AAEQNPIYWARYAAWLFTTPLLLLDLALLVDADEGT | SEQ. ID NO. 24 |
| P20A | AAEQNPIYWARYADWLFTTALLLLDLALLVDADEGT | SEQ. ID NO. 25 |
| D25E | AAEQNPIYWARYADWLFTTPLLLLELALLVDADEGT | SEQ. ID NO. 26 |
| D14E | AAEQNPIYWARYAEWLFTTPLLLLDLALLVDADEGT | SEQ. ID NO. 27 |
| 3D | AAEQNPIIYWARYADWLFTDLPLLLLDLLALLVDADEGT | SEQ. ID NO. 28 |
| R11Q | GEQNPIYWAQYADWLFTTPLLLLDLALLVDADEGTCG | SEQ. ID NO. 29 |
| D25Up | GGEQNPIYWARYADWLFTTPLLLDLLALLVDADEGTCG | SEQ. ID NO. 30 |

TABLE 1-continued

| Name | Sequence | SEQ ID NO: |
| --- | --- | --- |
| D25Down | GGEQNPIYWARYADWLFTTPLLLLLDALLVDADEGTCG | SEQ. ID NO. 31 |
| D14Up | GGEQNPIYWARYDAWLFTTPLLLLLDLALLVDADEGTCG | SEQ. ID NO. 32 |
| D14Down | GGEQNPIYWARYAWDLFTTPLLLLLDLALLVDADEGTCG | SEQ. ID NO. 33 |
| P20G | AAEQNPIYWARYADWLFTTGLLLLLDLALLVDADEGT | SEQ. ID NO. 34 |
| H1-Cys | DDDEDNPIYWARYADWLFTTPLLLLHGALLVDADECT | SEQ. ID NO. 35 |
| H1 | DDDEDNPIYWARYADWLFTTPLLLLHGALLVDADET | SEQ ID NO: 36 |
| H2-Cys | DDDEDNPIYWARYAHWLFTTPLLLLHGALLVDADEGCT | SEQ. ID NO. 37 |
| Cys-H2 | CDDDEDNPIYWARYAHWLFTTPLLLLHGALLVDADET | SEQ ID NO: 38 |
| H2 | DDDEDNPIYWARYAHWLFTTPLLLLHGALLVDADEGT | SEQ ID NO: 39 |
| H2N-Cys | DDDEDNPIYWARYAHWLFTTPLLLLHGALLVNADECT | SEQ. ID NO. 40 |
| H2N | DDDEDNPIYWARYAHWLFTTPLLLLHGALLVNADEGT | SEQ ID NO: 41 |
| H2N2-Cys | DDDEDNPIYWARYAHWLFTTPLLLLHGALLVNANECT | SEQ. ID NO. 42 |
| H2N2 | DDDEDNPIYWARYAHWLFTTPLLLLHGALLVNANEGT | SEQ ID NO: 43 |
| 1a-Trp | AEQNPIYWARYADFLFTTPLLLLDLALLVDADET | SEQ. ID NO. 44 |
| 1b-Trp | AEQNPIYFARYADWLFTTPLLLLDLALLVDADEGT | SEQ. ID NO. 45 |
| 1c-Trp | AEQNPIYFARYADFLFTTPLLLLDLALLWDADET | SEQ. ID NO. 46 |
| Fast-1 or Var1 | AKEDQNPYWARYADWLFTTPLLLLDLALLVDG | SEQ. ID NO. 47 |
| Var1-2D1D | ACEDQNPYWARYADWLFTTPLLLLDLALLVDG | SEQ. ID NO. 48 |
| Fast1-Cys or Var1-2D1D-Cys | AEDQNPYWARYADWLFTTPLLLLDLALLVDCG | SEQ. ID NO. 49 |
| Fast1-E-Cys or Var1E | AEDQNPYWARYADWLFTTPLLLLELALLVECG | SEQ. ID NO. 50 |
| Fast1-E-Lys | AKEDQNDPYWARYADWLFTTPLLLLDLALLVG | SEQ ID NO: 51 |
| Fast2 or Var2 | AKEDQNPYWRAYADLFTPLTLLDLLALWDG | SEQ. ID NO. 52 |
| Fast2-E-Cys or Var2E | AEDQNPYWARYADWLFTTPLLLLELALLVCG | SEQ ID NO: 53 |
| Var2-2D1D | ACEDQNPYWRAYADLFTPLTLLDLLALWDG | SEQ. ID NO. 54 |
| Var3-3D | ACDDQNPWRAYLDLLFPTDTLLLDLLW | SEQ. ID NO. 55 |
| Var3-3D-cys | AKDDQNPWRAYLDLLFPTDTLLLDLLWC | SEQ ID NO: 56 |
| Var4-3E | ACEEQNPWRAYLELLFPTETLLLELLW | SEQ ID NO: 57 |
| Var5-3Da | ACDDQNPWARYLDWLFPTDTLLLDL | SEQ. ID NO. 58 |
| Var6-3Db | CDNNNPWRAYLDLLFPTDTLLLDW | SEQ ID NO: 59 |
| Var8-3Eb | CEEQQPWAQYLELLFPTETLLLEW | SEQ ID NO: 60 |
| Var9-3Ec | CEEQQPWRAYLELLFPTETLLLEW | SEQ ID NO: 61 |
| Var15-2N | CDDDDDNPNYWARYANWLFTTPLLLLNGALLVEAEET | SEQ ID NO: 62 |
| Var16-2P | CDDDDDNPNYWARYAPWLFTTPLLLLPGALLVEAEE | SEQ ID NO: 63 |

TABLE 2

| Name | Sequence | SEQ ID NO: |
| --- | --- | --- |
| Var14-Rev | Ac-TEDADVLLALDLLLLPTTFLWDAYRAWYPNQECA-Am | SEQ. ID NO. 64 |
| Sh | AEQNPIYWARYADWLFTTPL | SEQ. ID NO. 65 |
| Sh-Cys | AEQNPIYWARYADWLFTTPCL | SEQ. ID NO. 66 |
| Cys-Sh | ACEQNPIYWARYADWLFTTPL | SEQ. ID NO. 67 |
| Sh-1Trp | AEQNPIYFARYADWLFTTPL | SEQ. ID NO. 68 |
| Sh-W2 | AEQNPIYFARYADLLFPTTLAW | SEQ ID NO. 69 |
| Sh-W1 | AEQNPIYWARYADLLFPTTLAF | SEQ ID NO. 70 |
| Sh-2W | AEQNPIYWARYADLLFPTTLAW | SEQ ID NO. 71 |
| Sh-1D | KEDQNPWARYADLLFPTTLAW | SEQ ID NO. 72 |
| Sh-1Db | KEDQNPWARYADLLFPTTLW | SEQ ID NO. 73 |
| Var12-1D | ACEDQNPWARYADLLFPTTLAW | SEQ ID NO. 74 |
| Var10-2D | ACEDQNPWARYADWLFPTTLLLLD | SEQ. ID NO. 75 |
| Var13-1E | ACEEQNPWARYAELLFPTTLAW | SEQ ID NO. 76 |
| Var11-2E | ACEEQNPWARYAEWLFPTTLLLLE | SEQ ID NO. 77 |

TABLE 2-continued

| Name | Sequence | SEQ ID NO: |
|---|---|---|
| Var7-3E | ACEEQNPWARYLEWLFPTETLLLEL | SEQ. ID NO. 78 |
| Var7-3Eb | ACEEQNPQAEYAEWLFPTTLLLLE | SEQ ID NO: 79 |

\* Ac means Acetylated N-terminus; and Am means Amidated C-terminus

TABLE 3

Coded and exemplary non-coded amino acids including L-isomers, D-isomers, alpha-isomers, beta-isomers, glycol-, and methyl- modifications.

| No. | Abbrev | Name |
|---|---|---|
| 1 | Ala | Alanine |
| 2 | Arg | Arginine |
| 3 | Asn | Asparagine |
| 4 | Asp | Aspartic acid |
| 5 | Cys | Cysteine |
| 6 | Gln | Glutamine |
| 7 | Glu | Glutamic acid |
| 8 | Gly | Glycine |
| 9 | His | Histidine |
| 10 | Ile | Isoleucine |
| 11 | Leu | Leucine |
| 12 | Lys | Lysine |
| 13 | Met | Methionine |
| 14 | Phe | Phenylalanine |
| 15 | Pro | Proline |
| 16 | Ser | Serine |
| 17 | Thr | Threonine |
| 18 | Trp | Tryptophan |
| 19 | Tyr | Tyrosine |
| 20 | Val | Valine |
| 21 | Sec | Selenocysteine |
| 22 | Sem | Selenomethionine |
| 23 | Pyl | Pyrrolysine |
| 24 | Aad | Alpha-aminoadipic acid |
| 25 | Acpa | Amino-caprylic acid |
| 26 | Aecys | Aminoethyl cysteine |
| 27 | Afa | Aminophenyl acetate |
| 28 | Gaba | Gamma-aminobutyric acid |
| 29 | Aiba | Aminoisobutyric acid |
| 30 | Aile | Alloisoleucine |
| 31 | Alg | Allylglycine |
| 32 | Aba | Amino-butyric acid |
| 33 | Aphe | Amino-phenylalanine |
| 34 | Brphe | Bromo-phenylalanine |
| 35 | Cha | Cyclo-hexylalanine |
| 36 | Cit | Citrulline |
| 37 | Clala | Chloroalanine |
| 38 | Cie | Cycloleucine |
| 39 | Clphe | Fencionine (or chlorophenylalanine) |
| 40 | Cya | Cysteic acid |
| 41 | Dab | Diaminobutyric acid |
| 42 | Dap | Diaminopropionic acid |
| 43 | Dap | Diaminopimelic acid |
| 44 | Dhp | Dehydro-proline |
| 45 | Dhphe | DOPA (or 3,4-dihydroxyphenylalanine) |
| 46 | Fphe | Fluorophenylalanine |
| 47 | Gaa | Glucosaminic acid |
| 48 | Gla | Gamma-carboxyglutamic acid |
| 49 | Hag | Homoarginine |
| 50 | Hlys | Hydroxylysine |
| 51 | Hnvl | Hydroxynorvaline |
| 52 | Hog | Homoglutamine |
| 53 | Hoph | Homophenylalanine |
| 54 | Has | Homoserine |
| 55 | Hse | Homocysteine |
| 56 | Hpr | Hydroxyproline |
| 57 | Iphe | Iodo-phenylalanine |
| 58 | Ise | Isoserine |
| 59 | Mle | Methyl-leucine |
| 60 | Msmet | Methionine-methylsulfonium chloride |
| 61 | Nala | Naphthyl-alanine |
| 62 | Nle | Norleucine (or 2-aminohexanoic acid) |

TABLE 3-continued

Coded and exemplary non-coded amino acids including L-isomers, D-isomers, alpha-isomers, beta-isomers, glycol-, and methyl- modifications.

| No. | Abbrev | Name |
|---|---|---|
| 63 | Nmala | N-methyl-alanine |
| 64 | Nva | Norvaline (or 2-aminopentanoic acid) |
| 65 | Obser | O-benzyl-serine |
| 66 | Obtyr | O-benzyl-tyrosine |
| 67 | Oetyr | O-ethyl-tyrosine |
| 68 | Omser | O-methyl-serine |
| 69 | Omthr | O-methy-threonine |
| 70 | Omtyr | O-methyl-tyrosine |
| 71 | Orn | Ornithine |
| 72 | Pen | Penicillamine |
| 73 | Pga | Pyroglutamic acid |
| 74 | Pip | Pipecolic acid |
| 75 | Sar | Sarcosine |
| 76 | Tfa | Trifluoro-alanine |
| 77 | Thphe | Hydroxy-Dopa |
| 78 | Vig | Vinylglycine |
| 79 | Aaspa | Amino-aminoethylsulfanylpropanoic acid |
| 80 | Ahdna | Amino-hydroxy-dioxanonanolic acid |
| 81 | Ahoha | Amino-hydroxy-oxahexanoic acid |
| 82 | Ahsopa | Amino-hydroxyethylsulfanylpropanoic acid |
| 83 | Tyr(Me) | Methoxyphenyl-methylpropanyl oxycarbonylamino propanoic acid |
| 84 | MTrp | |
| 85 | pTyr | Methyl-tryptophan |
| 86 | pSer | Phosphorylated Tyr |
| 87 | pThr | Phosphorylated Ser |
| 88 | BLys | Phosphorylated Thr |
| 89 | Hyp | BiotinLys |
| 90 | Phg | Hydroproline |
| 91 | Cha | Phenylglycine |
| 92 | Chg | Cyclohexyl-alanine |
| 93 | Nal | Cyclohexylglycine |
| 94 | Pal | Naphthylalanine |
| 95 | Pra | Pyridyl-alanine |
| 96 | Gly(allyl) | Propargylglycine |
| 97 | Pen | Pentenoic acid |
| 98 | MetO | Penicillamine |
| 99 | Pca | Methionine sulfoxide |
| 100 | Ac-Lys | Pyrogiutatnic acid Acetylation of Lys |

TABLE 4

Non-limiting examples of protonatable residues and their substitutions including L-isomers, D-isomers, alpha-isomers, and beta-isomers.

| Original Residue | Exemplary amino acids substitution |
|---|---|
| Asp (D) | Glu (E); Gla (Gla); Aad (Aad) |
| Glu (E) | Asp (D); Gla (Gla); Aad (Aad) |

TABLE 5

Examples of coded amino acid substitutions

| Original Residue | Substitution |
|---|---|
| Ala (A) | Gly; Ile; Leu; Met; Phe; Pro; Trp; Tyr; Val |
| Arg (R) | Lys |
| Asn (N) | Gln; His |
| Asp (D) | Glu |
| Cys (C) | Ser; Met |
| Gln (Q) | Asn; His |
| Glu (E) | Asp |
| Gly (G) | Ala; Ile; Leu; Met; Phe; Pro; Trp; Tyr; Val |
| His (H) | Asn; Gln |
| Ile (I) | Ala; Gly; Leu; Met; Phe; Pro; Trp; Tyr; Val |
| Leu (L) | Ala; Gly; Ile; Met; Phe; Pro; Trp; Tyr; Val |
| Lys (K) | Arg |

TABLE 5-continued

Examples of coded amino acid substitutions

| Original Residue | Substitution |
|---|---|
| Met (M) | Ala; Gly; Leu; Ile; Phe; Pro; Trp; Tyr; Val |
| Phe (F) | Ala; Gly; Leu; Ile; Met; Pro; Trp; Tyr; Val |
| Pro (P) | Ala; Gly; Leu; Ile; Met; Phe; Trp; Tyr; Val |
| Ser (S) | Thr |
| Thr (T) | Ser |
| Trp (W) | Ala; Gly; Leu; Ile; Met; Pro; Phe; Tyr; Val |
| Tyr (Y) | Ala; Gly; Leu; Ile; Met; Pro; Phe; Trp; Val |
| Val (V) | Ala; Gly; Leu; Ile; Met; Pro; Phe; Trp; Tyr |

TABLE 6

Non-limiting examples of membrane-inserting sequences belonging to different groups of pHLIP ® peptides. Each protonatable residue (shown in bold) could be replaced by its substitution from Table 4. Each non-polar residue could be replaced by its coded amino acid substitution from Table 5, and/or non-coded amino acid substitutions from Table 3.

| Groups | Sequences (SEQ ID NO:) |
|---|---|
| WT-BRC | WARYADWLFTTPLLLLDLALL (SEQ ID NO: 80) |
| | YARYADWLFTTPLLLLDLALL (SEQ ID NO: 81) |
| | WARYSDWLFTTPLLLYDLGLL (SEQ ID NO: 82) |
| | WARYTDWFTTPLLLYDLALLA (SEQ ID NO: 83) |
| | WARYTDWLFTTPLLLYDLGLL (SEQ ID NO: 84) |
| | WARYADWLFTTPLLLLDLSLL (SEQ ID NO: 85) |
| WT-BRC Reverse | LLALDLLLLPTTFLWDAYRAW (SEQ ID NO: 86) |
| | LLALDLLLLPTTFLWDAYRAY (SEQ ID NO: 87) |
| | LLGLDYLLLPTTFLWDSYRAW (SEQ ID NO: 88) |
| | ALLALDYLLLPTTFWDTYRAW (SEQ ID NO: 89) |
| | LLGLDYLLLPTTFLWDTYRAW (SEQ ID NO: 90) |
| | LLSLDLLLLPTTFLWDAYRAW (SEQ ID NO: 91) |
| ATRAM | GLAGLLGLEGLLGLPLGLLEGLWLGL (SEQ ID NO: 92) |
| ATRAM Reverse | LGLWLGELLGLPLGLLELGLLGALG (SEQ ID NO: 93) |

TABLE 6-continued

Non-limiting examples of membrane-inserting sequences belonging to different groups of pHLIP ® peptides. Each protonatable residue (shown in bold) could be replaced by its substitution from Table 4. Each non-polar residue could be replaced by its coded amino acid substitution from Table 5, and/or non-coded amino acid substitutions from Table 3.

| Groups | Sequences (SEQ ID NO:) |
|---|---|
| Var3 | WRAYLDLLFPTDTLLLDLLW (SEQ ID NO: 94) |
| Var3 Reverse | WLLDLLLTDTPFLLDLYARW (SEQ ID NO: 95) |
| Var7 | WARYLEWLFPTETLLLEL (SEQ ID NO: 96) |
| | WAQYLELLFPTETLLLEW (SEQ ID NO: 97) |
| Var7 Reverse | LELLLTETPFLWELYRAW (SEQ ID NO: 98) |
| | WELLLTETPFLLELYQAW (SEQ ID NO: 99) |
| Single D/E | WLFTTPLLLLLNGALLVE (SEQ ID NO: 100) |
| | WLFTTPLLLLPGALLVE (SEQ ID NO: 101) |
| | WARYADLLFPTTLAW (SEQ ID NO: 102) |
| Single D/E Reverse | EVLLAGNLLLLPTTFLW (SEQ ID NO: 103) |
| | EVLLAGPLLLLPTTFLW (SEQ ID NO: 104) |
| | WALTTPFLLDAYRAW (SEQ ID NO: 105) |
| pHLIP ®-Rho | NLEGFFATLGGEIALWSLVVLAIE (SEQ ID NO: 106) |
| | EGFPATLGGEIALWSDVVLAIE (SEQ ID NO: 107) |
| | EGFPATLGGEIPLWSDVVLAIE (SEQ ID NO: 108) |
| pHLIP ®-Rho Reverse | EIALVVLSWLAIEGGLTAFFGELN (SEQ ID NO: 109) |
| | EIALVVDSWLAIEGGLTAFFGE (SEQ ID NO: 110) |
| | EIALVVDSWLPIEGGLTAFFGE (SEQ ID NO: 111) |
| pHLIP ®-CA9 | ILDLVFGLLFAVTSVDFLVQW (SEQ ID NO: 112) |
| pHLIP ®-CA9 Reverse | WQVLFDVSTVAFLLGFVLDLI (SEQ ID NO: 113) |

TABLE 7

Non-limiting examples of pHLIP ® sequences. A cysteine, a lysine, an azido-modified amino acid, or an alkynyl modified amino acid can be incorporated at the N-terminal (first 6 residues) or C-terminal (last 6 residues) parts of the peptides for conjugation with a cargo, and a linker.

| SEQ ID NO: | Name | Sequence |
|---|---|---|
| SEQ ID NO: 114 | WT-2D | AEQNPIYWARYADWLFTTPLLLLDLALLVDADET |
| SEQ ID NO: 115 | WT-6E | AEQNPIYWARYAEWLFTTPLLLLELALLVEAEET |
| SEQ ID NO: 116 | WT-3D | ADDQNPWRAYLDLLFPDTTDLLLLDLLWDADET |
| SEQ ID NO: 117 | WT-9E | AEEQNPWRAYLELLFPETTELLLLELLWEAEET |
| SEQ ID NO: 118 | WT-G1aD | AEQNPIYWARYAG1aWLFTTPLLLLDLALLVDADET |
| SEQ ID NO: 119 | WT-DG1a | AEQNPIYWARYADWLFTTPLLLLG1aLALLVDADET |
| SEQ ID NO: 120 | WT-2G1a | AEQNPIYWARYAG1aWLFTTPLLLLG1aLALLVDADET |
| SEQ ID NO: 121 | WT-AadD | AEQNPIYWARYAAadWLFTTPLLLLDLALLVDADET |
| SEQ ID NO: 122 | WT-DAad | AEQNPIYWARYADWLFTTPLLLLAadLALLVDADET |
| SEQ ID NO: 123 | WT-2Aad | AEQNPIYWARYAAadWLFTTPLLLLAadLALLVDADET |

TABLE 7-continued

Non-limiting examples of pHLIP ® sequences. A cysteine, a lysine, an azido-modified amino acid, or an alkynyl modified amino acid can be incorporated at the N-terminal (first 6 residues) or C-terminal (last 6 residues) parts of the peptides for conjugation with a cargo, and a linker.

| SEQ ID NO: | Name | Sequence |
|---|---|---|
| SEQ ID NO: 124 | WT-GlaAad | AEQNPIYWARYAGlaWLFTTPLLLLAadLALLVDADET |
| SEQ ID NO: 125 | WT-AadGla | AEQNPIYWARYAAadWLFTTPLLLLGlaLALLVDADET |
| SEQ ID NO: 126 | WT-1 | GGEQNPIYWARYADWLFTTPLLLLDLALLVDADEGT |
| SEQ ID NO: 127 | WT-2 | GGEQNPIYWARYADWLFTTPLLLLDLALLVDADEGT |
| SEQ ID NO: 128 | WT-3 | AAEQNPIYWARYADWLFTTPLLLLDLALLVDADEGT |
| SEQ ID NO: 129 | WT-4 | AEQNPIYWARYADWLFTTPLLLLDLALLVDADEGT |
| SEQ ID NO: 130 | WT-2N | AEQNPIYWARYANWLFTTPLLLLNLALLVDADEGT |
| SEQ ID NO: 131 | WT-2K | AEQNPIYWARYAKWLFTTPLLLLKLALLVDADEGT |
| SEQ ID NO: 132 | WT-2DNANQ | GGEQNPIYWARYADWLFTTPLLLLDLALLVNANQGT |
| SEQ ID NO: 133 | WT-D25A | AAEQNPIYWARYADWLFTTPLLLLALALLVDADEGT |
| SEQ ID NO: 134 | WT-D14A | AAEQNPIYWARYAAWLFTTPLLLLDLALLVDADEGT |
| SEQ ID NO: 135 | WT-P20A | AAEQNPIYWARYADWLFTTALLLLDLALLVDADEGT |
| SEQ ID NO: 136 | WT-D25E | AAEQNPIYWARYADWLFTTPLLLLELALLVDADEGT |
| SEQ ID NO: 137 | WT-D14E | AAEQNPIYWARYAEWLFTTPLLLLDLALLVDADEGT |
| SEQ ID NO: 138 | WT-3D-2 | AAEQNPIIYWARYADWLFTDLPLLLLDLLALLVDADEGT |
| SEQ ID NO: 139 | WT-R11Q | GEQNPIYWAQYADWLFTTPLLLLDLALLVDADEG |
| SEQ ID NO: 140 | WT-D25Up | GGEQNPIYWARYADWLFTPLLLLDLLALLVDADEG |
| SEQ ID NO: 141 | WT-D25Down | GGEQNPIYWARYADWLFTTPLLLLLDALLVDADEG |
| SEQ ID NO: 142 | WT-D14Up | GGEQNPIYWARYDAWLFTTPLLLLDLALLVDADEGT |
| SEQ ID NO: 143 | WT-D14Down | GGEQNPIYWARYAWDLFTTPLLLLDLALLVDADEG |
| SEQ ID NO: 144 | WT-P20G | AAEQNPIYWARYADWLFTGLLLLDLALLVDADEGT |
| SEQ ID NO: 145 | WT-DH | DDDEDNPIYWARYADWLFTTPLLLLHGALLVDAD |
| SEQ ID NO: 146 | WT-2H | DDDEDNPIYWARYAHWLFTTPLLLLHGALLVDADE |
| SEQ ID NO: 147 | WT-L16H | CEQNPIYWARYADWHFTTPLLLLDLALLVDADE |
| SEQ ID NO: 148 | WT-1Wa | AEQNPIYWARYADFLFTTPLLLLDLALLVDADET |
| SEQ ID NO: 149 | WT-1Wb | AEQNPIYFARYADWLFTTPLLLLDLALLVDADE |
| SEQ ID NO: 150 | WT-1Wc | AEQNPIYFARYADFLFTTPLLLLDLALLWDADET |
| SEQ ID NO: 151 | WT-W6 | ADNNPWIYARYADLTTFPLLLLDLALLVDFDD |
| SEQ ID NO: 152 | WT-W17 | ADNNPFIYARYADLTTWPLLLLDLALLVDFDD |
| SEQ ID NO: 153 | WT-W30 | ADNNPFIYARYADLTTFPLLLLDLALLVDWDD |
| SEQ ID NO: 154 | WT-W17-P7 | ADNNPFPYARYADLTTWILLLLDLALLVDFDD |
| SEQ ID NO: 155 | WT-W39-R11 | ADNNPFIYAYRADLTTFPLLLLDLALLVDWDD |
| SEQ ID NO: 156 | WT-W30-R15 | ADNNPFIYATYADLRTFPLLLLDLALLVDWDD |
| SEQ ID NO: 157 | WT-Rev | Ac-TEDADVLLALDLLLLPTTFLWDAYRAWYPNQEA-Am |
| SEQ ID NO: 158 | Var1-3D | AEDQNPYWARYADWLFTTPLLLLDLALLVD |
| SEQ ID NO: 159 | Var1-1D2E | AEDQNPYWARYADWLFTTPLLLLELALLVE |

TABLE 7-continued

Non-limiting examples of pHLIP ® sequences. A cysteine, a lysine, an azido-modified amino acid, or an alkynyl modified amino acid can be incorporated at the N-terminal (first 6 residues) or C-terminal (last 6 residues) parts of the peptides for conjugation with a cargo, and a linker.

| SEQ ID NO: | Name | Sequence |
| --- | --- | --- |
| SEQ ID NO: 160 | Var2-3D | AEDQNPYWRAYADLFTPLTLLDLLALWD |
| SEQ ID NO: 161 | Var3-3D | ADDQNPWRAYLDLLFPTDTLLLDLLW |
| SEQ ID NO: 162 | Var3-WT | ADDQNPWRAYLDLLFPTDTLLLDLLWDADE |
| SEQ ID NO: 163 | Var3-Gla2D | ADDQNPWRAYLGlaLLFPTDTLLLDLLW |
| SEQ ID NO: 164 | Var3-DGlaD | ADDQNPWRAYLDLLFPTGlaTLLLDLLW |
| SEQ ID NO: 165 | Var3-2DGla | ADDQNPWRAYLDLLFPTDTLLLGlaLLW |
| SEQ ID NO: 166 | Var3-2GlaD | ADDQNPWRAYLGlaLLFPTGlaTLLLDLLW |
| SEQ ID NO: 167 | Var3-GlaDGla | ADDQNPWRAYLGlaLLFPTDTLLLGlaLLW |
| SEQ ID NO: 168 | Var3-D2Gla | ADDQNPWRAYLDLLFPTGlaTLLLGlaLLW |
| SEQ ID NO: 169 | Var3-3Gla | ADDQNPWRAYLGlaLLFPTGlaTLLLGlaLLW |
| SEQ ID NO: 170 | Var3-Aad2D | ADDQNPWRAYLAadLLFPTDTLLLDLLW |
| SEQ ID NO: 171 | Var3-DAadD | ADDQNPWRAYLDLLFPTAadTLLLDLLW |
| SEQ ID NO: 172 | Var3-2DAad | ADDQNPWRAYLDLLFPTDTLLLAadLLW |
| SEQ ID NO: 173 | Var3-2AadD | ADDQNPWRAYLAadLLFPTAadTLLLDLLW |
| SEQ ID NO: 174 | Var3-AadDAad | ADDQNPWRAYLAadLLFPTDTLLLAadLLW |
| SEQ ID NO: 175 | Var3-D2Aad | ADDQNPWRAYLDLLFPTAadTLLLAadLLW |
| SEQ ID NO: 176 | Var3-3Aad | ADDQNPWRAYLAadLLFPTAadTLLLAadLLW |
| SEQ ID NO: 177 | Var3-GlaAadD | ADDQNPWRAYLGlaLLFPTAadTLLLDLLW |
| SEQ ID NO: 178 | Var3-GlaDAad | ADDQNPWRAYLGlaLLFPTDTLLLAadLLW |
| SEQ ID NO: 179 | Var3-2GlaAad | ADDQNPWRAYLGlaLLFPTGlaTLLLAadLLW |
| SEQ ID NO: 180 | Var3-AadGlaD | ADDQNPWRAYLAadLLFPTGlaTLLLDLLW |
| SEQ ID NO: 181 | Var3-AadDGla | ADDQNPWRAYLAadLLFPTDTLLLGlaLLW |
| SEQ ID NO: 182 | Var3-GlaAadGla | ADDQNPWRAYLGlaLLFPTAadTLLLGlaLLW |
| SEQ ID NO: 183 | Var3-GLL | GEEQNPWLGAYLDLLFPLELLGLLELGLW |
| SEQ ID NO: 184 | Var3-M | ADDDDDDPWQAYLDLLFPTDTLLLDLLW |
| SEQ ID NO: 185 | Var4-3E | AEEQNPWRAYLELLFPTETLLLELLW |
| SEQ ID NO: 186 | Var5-3Da | ADDQNPWARYLDWLFPTDTLLLDL |
| SEQ ID NO: 187 | Var6-3Db | DNNNPWRAYLDLLFPTDTLLLDW |
| SEQ ID NO: 188 | Var7-3E | AEEQNPWARYLEWLFPTETLLLEL |
| SEQ ID NO: 189 | Var7-M | DDDDDDPWQAYLDLFPTDTLALDLW |
| SEQ ID NO: 190 | Var8-3E | EEQQPWAQYLELLFPTETLLLEW |
| SEQ ID NO: 191 | Var9-3E | EEQQPWRAYLELLFPTETLLLEW |
| SEQ ID NO: 192 | Var10-2D | AEDQNPWARYADWLFPTTLLLLD |
| SEQ ID NO: 193 | Var11-2E | AEEQNPWARYAEWLFPTTLLLLE |
| SEQ ID NO: 194 | Var12-1D | AEDQNPWARYADLLFPTTLAW |
| SEQ ID NO: 195 | Var13-1E | AEEQNPWARYAELLFPTTLAW |

TABLE 7-continued

Non-limiting examples of pHLIP ® sequences. A cysteine, a lysine, an azido-modified amino acid, or an alkynyl modified amino acid can be incorporated at the N-terminal (first 6 residues) or C-terminal (last 6 residues) parts of the peptides for conjugation with a cargo, and a linker.

| SEQ ID NO: | Name | Sequence |
| --- | --- | --- |
| SEQ ID NO: 196 | Var15-2N | DDDDDNPNYWARYANWLFTTPLLLLNGALLVEAEET |
| SEQ ID NO: 197 | Var16-2P | DDDDDNPNYWARYAPWLFTTPLLLLPGALLVEAEET |
| SEQ ID NO: 198 | Var17 | AEQNPIYFARYADFLFTTPLLLLDLALLWDADET |
| SEQ ID NO: 199 | Var18 | AEQNPIYWARYADFLFTTPLLLLDLALLVDADET |
| SEQ ID NO: 200 | Var19a | AEQNPIYWARYADWLFTTPL |
| SEQ ID NO: 201 | Var20 | AEQNPIYFARYADLLFPTTLAW |
| SEQ ID NO: 202 | Var21 | AEQNPIYWARYADLLFPTTLAF |
| SEQ ID NO: 203 | Var22 | AEQNPIYWARYADLLFPTTLAW |
| SEQ ID NO: 204 | Var23 | AEQNPIYFARYADWLFTTPL |
| SEQ ID NO: 205 | Var24 | EDQNPWARYADLLFPTTLAW |
| SEQ ID NO: 206 | ATRAM | GLAGLAGLLGLEGLLGLPLGLLEGLWLGLELEGN |
| SEQ ID NO: 207 | pHLIP ®-CA9 | EQNPIYILDLVEGLLFAVTSVDELVQWDDAGD |
| SEQ ID NO: 208 | pHLIP ®-Rho | NLEGFFATLGGEIALWSLVVLAIE |
| SEQ ID NO: 209 | pHLIP ®-RhoM1 | NNEGFFATLGGEIALWSDVVLAIE |
| SEQ ID NO: 210 | pHLIP ®-RhoM2 | DNNEGFFATLGGEIPLWSDVVLAIE |

Example 1: pHLIP® Peptides pHLIP® peptides are described here and in U.S. Pat. Nos. 9,814,781 and 9,289,508 (hereby incorporated by reference) as well as U.S. Patent Publication 20180117183, 20180064648, 20180221500, 20180117183, 20180064648, 20160256560, 20150191508, 20150051153, and 20120142042, 20120039990, and 20080233107, each of which is hereby incorporated by reference.

STING is known in the literature but the use of STING agonists has been hampered by cell delivery issues. FIGS. 13-16 show exemplary pHLIP®-linker-Cargo constructs, e.g., with the cargo being an immune-stimulatory compound. As described above, it is difficult to achieve delivery of charged molecules to go through a cell membrane. Constructs described here, e.g., a pHLIP®-linker-Cargo construct, mediate cancer and immune cell targeting (due to their surface low pH)) and also avoid or minimize a global auto-immune response with a STING agonist (for instance cGAMP). The problem of targeting the cargo, e.g., an immune-stimulating drug, and getting the cargo inside the cell is solved by the pHLIP®/drug compositions and methods described herein.

A linker could be relatively small, e.g., only a few atoms, to a rather large polymer of 4-5 kDa. FIGS. 13-16 show an exemplary heterobifunctional linker that reacts on one end with a free thiol to spontaneously form a disulfide bond, with thiopyridine as a leaving group, and on the other end reacts with activated with amine or hydroxyl groups in the presence of DIPEA, and in some cases DMAP or other activator base, to form a carbamate or carbonate, respectively. This material can be used if pHLIP® (A) is protected at its amino terminus, such as with N-acetylation. This material can also be reacted with pHLIP® bearing a cysteine residue or with a thiol-bearing linker for subsequent conjugation to pHLIP®, and forms a conjugate by disulfide exchange with thiopyridine as a leaving group. This material can be used to form a conjugate with pHLIP® bearing a lysine residue, if pHLIP® is protected at its amino terminus, such as with N-acetylation.

In some examples, a succinimidyl 3-(2-pyridyldithio) propionate (SPDP) cross-linker is used. SPDP is a short-chain crosslinker for amine-to-sulfhydryl conjugation via NHS-ester and pyridyldithiol reactive groups that form cleavable (reducible) disulfide bonds with cysteine sulfhydryls. SPDP is used to activate $NH_2$ derivative of cCDN (of e.g., c[3'-AHC-G(2',5')pA(3',5')p], or c[G(2',5')p-2'-AHC-A (3',5')p]), purify and exchange disulfide with SH of single Cys at the C-terminus of pHLIP® to obtain pHLIP®-S-S-Ccdn.

In some examples, the following cross-linkers can be used: LC-SPDP (succinimidyl 6-(3(2-pyridyldithio)propionamido)hexanoate); Sulfo-LC-SPDP (sulfosuccinimidyl 6-(3'-(2-pyridyldithio)propionamido)hexanoate); PEG4-SPDP (PEGylated, long-chain SPDP crosslinker); PEG12-SPDP (PEGylated, long-chain SPDP crosslinker); SMCC (succinimidyl 4-(N-maleimidomethyl)cyclohexane-1-carboxylate); Sulfo-SMCC (sulfosuccinimidyl 4-(N-maleimidomethyl)cyclohexane-1-carboxylate); SMPT (4-succinimidyloxycarbonyl-alpha-methyl-α(2-pyridyldithio)toluene); DTME (dithiobismaleimidoethane).

The invention may encompass the following embodiments.

A compound of formula:

Peptide-Mod-Linker-Drug     (1), wherein:
Peptide is a pHLIP® peptide,
Mod is a modulator, and it is optional. It comprises chemical entity to modulate overall polarity of Linker-Drug for optimized intracellular delivery by pHLIP®. To achieve optimized intracellular delivery the overall polarity of Mod-Linker-Drug measured by Log P, where P is the measured octanol-water partition coefficient, is preferably in the range $-1<\text{Log P}<1$. If the cargo is polar (Log $P<-0.4$), the hydrophobic modulator will increase the Log P of [cargo-modulator] (Log $P>-0.4$). If the cargo is hydrophobic Log $P>2.5$, the polar modulator will decrease Log P of [cargo-modulator] (Log $P<2.5$).

In some cases, an immune-stimulatory compound or drug is moderately hydrophobic. The average value of Log P for drugs is about 2-3. Exemplary cargo compounds, e.g., immune-stimulatory compounds or drugs, are polar, moderately hydrophobic or hydrophobic as defined by the following characteristics. Polar: Log P $<-0.4$; Moderately hydrophobic: $2.5<\text{Log P} <-0.4$; and Hydrophobic: Log P $>2.5$. The polarity and/or hydrophobicity of a drug or compound to be delivered is measured using methods know in the art, e.g., by determining Log P, in which P is octanol-water partition coefficient. A substance is dissolved into octanol-water mixture, mixed and allowed to come to equilibration. The amount of substance in each (or one) phases is then measured. The measurements itself could be in a number of ways know in the art, e.g., by measuring absorbance, or determining the amount using NMR, HPLC, or other known methods.

Drug comprises or consists of a drug or compound with anticancer activity.

Linker comprises a covalent bond or a chemical linker such that (1) is selected from the following (for example, where "Drug" includes an Immuno-Stimulatory Compound):

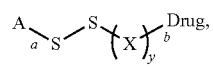

(2)

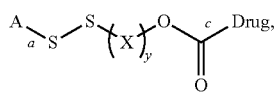

(3)

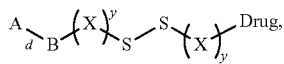

(4)

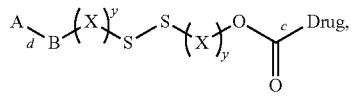

(5)

each occurrence of y may be present or absent and is independently an integer ranging from 1 to 4;
each occurrence of X is independently selected from the group consisting of $CH_2$, CH(alkyl), and $C(alkyl)_2$;
each occurrence of B may be present or absent and is independently selected from the group consisting of alkyl, aryl, and PEG;
bond a is formed between the sulfur and the thiol substituent of a cysteine residue in A;
bond b is formed between the carbon and a substituent on Drug (e.g., an immuno-stimulatory compound), wherein the substituent is selected from the group consisting of hydroxyl, carbonyl, amine, amide, sulfate, sulfonamide, phosphate, and phosphoramide;
bond c is formed between the carbonyl and a substituent on Drug (e.g., an immuno-stimulatory compound), wherein the substituent is selected from the group consisting of primary amine, secondary amine, and hydroxyl;
bond d is formed between B and an amino acid residue in A, wherein the amino acid is selected from the group consisting of serine, threonine, tyrosine, tryptophan, histidine, lysine, and cysteine and comprises an amide, ester, carbamate, carbonate, or maleimide bond; and
Drug is an anticancer drug with an immune associated mechanism of action, including but not limited to the group consisting of RIG-I agonist, TLR-7 agonist, and STING agonist; or a salt, solvate, enantiomer, diasterioisomer, geometric isomer, or tautomer thereof.

A compound of formula (1), wherein Drug (e.g., an immuno-stimulatory compound) is a cyclic dinucleotide STING agonist.

A compound of formula (1), wherein Drug (e.g., an immuno-stimulatory compound) is selected from the group consisting of cyclic dinucleotides: c-GAMP (or cyclic GMP-AMP); c-diAMP (or cyclic di-AMP); c-diGMP (or cyclic di-GMP):

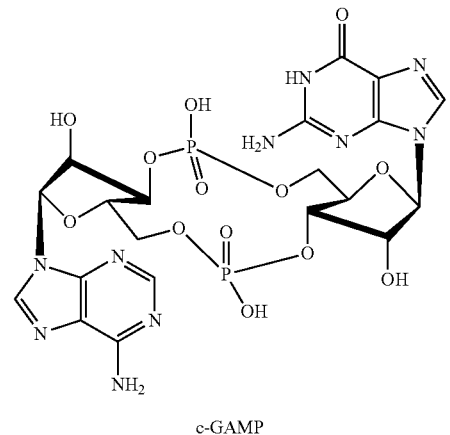

c-GAMP

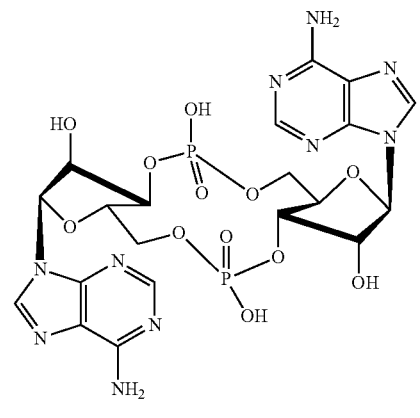

c-diAMP

-continued

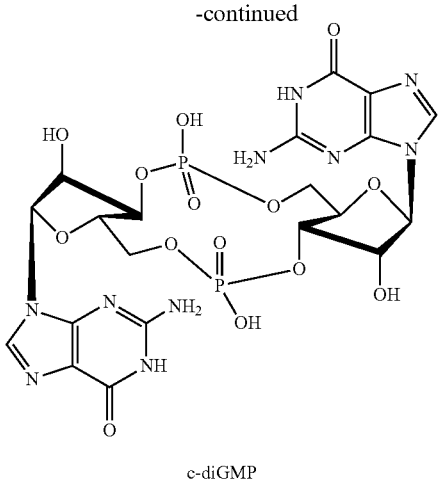

c-diGMP and their analogs and derivatives. The non-limiting examples are cyclic di-nucleotides in which:
- one or both phosphate moieties, where one of two exocyclic oxygens is replaced by sulfur for improved stability against degradation by phosphodiesterases;
- the hydrogen in position 8 of one or both guanine nucleobase is modified for conjugation with one or two pHLIP® peptides;
- the hydrogen in position 8 of one of both adenine nucleobase is modified for conjugation with one or two pHLIP® peptides;
- the hydrogen in position 8 of both adenine and guanine nucleobases is modified for conjugation with one or two pHLIP® peptides;
- a spacer with a terminal reactive group is attached to one or both ribose 3'-hydroxy group of the guanosine for conjugation with one or two pHLIP® peptides;
- a spacer with a terminal reactive group is attached to one or both ribose 2'-hydroxy group of the adenosine for conjugation with one or two pHLIP® peptides;
- 2'-deoxy analogues;
- both the N1 and the N6 nitrogen atoms in the adenine nucleobase are connected by an etheno bridge forming a tricyclic ring system;
- synthetic cGAMP linked via two 2',5' phosphodiester bonds;
- synthetic c-diAMP containing two distinct phosphodiester linkages similar to the cGAMP;
- metabolic degradation products of c-GAMP, c-diAMP, c-diGMP.

Example 2: pHLIP®-Mediated Tumor Targeting and Cytoplasmic Delivery of CDNs pHLIP-CDNs (cyclic di-nucleotides), STING agonists, such as pHLIP-S-S-cGAMP (schematic below), are synthesized and purified by CheminPharma, Inc. STING agonists are coupled to C-terminal, membrane-inserting end of pHLIP® peptide via self-immolative linkers and are released in cytoplasm in their non-modified form to be able effectively activate STING pathway.

A

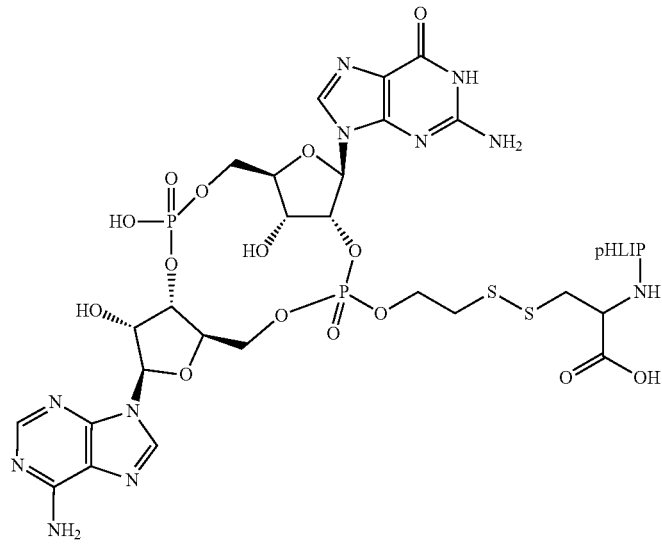

-continued

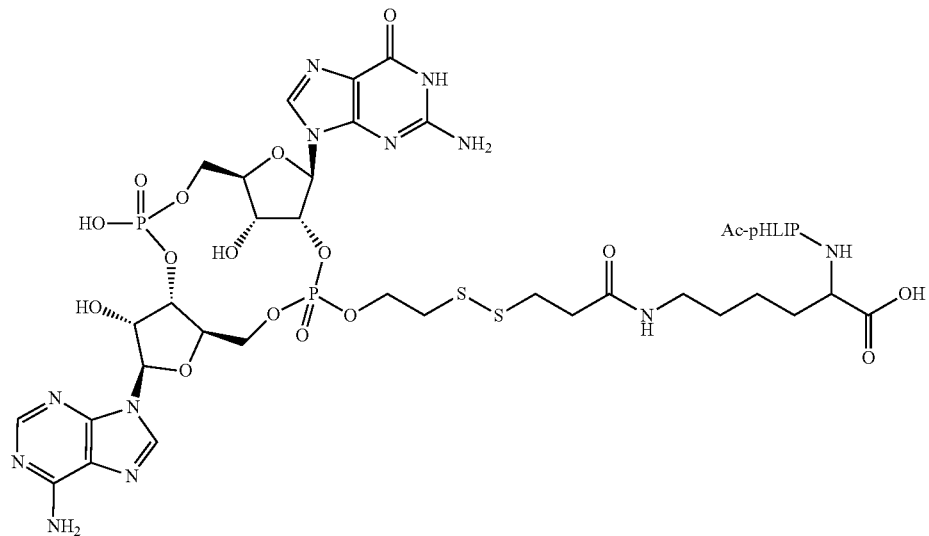

B

Chemical structures of pHLIP-S-S-cGAMP conjugates cGAMP is coupled with Cys at pHLIP® peptide (A) or Lys at acytilated pHLIP® peptide (B).

pHLIP-S-S-cGAMP are tested on B16-Blue ISG and B16-Blue ISG-KO-STING cells (Invitrogen). B16-Blue ISO is a murine melanoma cell line stably transfected with a secreted embryonic alkaline phosphatase (SEAP) gene under the control of the interferon-inducible ISG54 promoter enhanced by a multimeric interferon-stimulated response element (ISRE) (http://www.invivogen.com/b 16-blue-isg). B16-Blue ISO-KO-STING cells are derived from B16-Blue ISO by stable knockout of the stimulator of interferon genes (STING) gene (http://www.invivogen-.com/b 16-blue-isg-ko-sting). B16-Blue ISG cells express the secreted embryonic alkaline phosphatase (SEAP) reporter gene under control of interferon-inducible ISG54 promoter. Stimulation of B16-Blue ISG with CDNs triggers the production of interferons, leading to activation of I-ISG54 promoter and the production of SEAP in the supernatant. Level of SEAP in supernatant can be determined by measuring of absorbance at 655 nm. B16-Blue ISG and B16-Blue ISG-KO-STING cells are seeded 30,000/well in 96-well plate. The next day cells are treated with different concentrations of ADU-S100 (positive control) and pHLIP-S-S-cGAMP in 80 μl DMEM without PBS, pH 6.2 for 2 hour followed by addition of 40 μl of DMEM/20% FBS, pH 7.4 for 22 hours. The 50 μl of supernatant is taken from each well, mixed with 150 μl QUANTI-Blue solution (Invivogen) and incubated for 1.5-2 hours at 37° C., and optical density is measured at 655 nm. When STING pathway is activated in B16-Blue ISG cells, the absorbance readings increase Self-imolating chemistry, e.g., linker(s), is used to release STING agonists in their non-modified form.

pHLIP-S-S-cGAMP agonists are given as multiple intraperitoneal (IP) or intratumoral (IT) injections into mice bearing HeLa cervical tumor in flanks of female athymic nude mice. When tumor is reached size of about 1 cm³ (about 1 g) in the control (non-treated) group, the animals are sacrificed; tumors are collected and weighted. About 40-60% of tumor weight reduction is observed after administration of pHLIP-S-S-cGAMP agonist.

pHLIP®-Mediated Intracellular Delivery of Immuno-Stimulatory Compounds

Provided herein is a composition comprising an immunostimulatory compound and a pHLIP® peptide. In some examples, the composition has the following structure: Peptide—Linker-ISC, wherein "Peptide" is a pHLIP® peptide comprising the sequence ADQDNPWRAYLDLL-FPTDTLLLDLLWCA (SEQ ID NO: 212) or ADDQNP-WRAYLDLLFPTDTLLLDLLWCA (SEQ ID NO: 10) or ADQDNPWRAYLDLLFPTDTLLLDLLWKA (SEQ ID NO: 213) or ADDQNPWRAYLDLLFPTDTLLLDLLWKA (SEQ ID NO: 217), wherein "Linker" is a cleavable linker, wherein "ISC" is an immuno-stimulatory compound, and wherein each "—" is a covalent bond.

In some examples, the immuno-stimulatory compound comprises cyclic dinucleotides (CDNs), or derivatives thereof. In other aspects, the immune-stimulatory compound comprises cyclic purine dinucleotide. Also, as describe herein, the immuno-stimulatory compound includes a cyclic purine dinucleotide which binds to stimulator of interferon genes (STING). In still other examples, the immuno-stimulatory compound comprises a cGAMP, 3',5'-cyclic diadenylic acid (c-di-AMP), or a cyclic diguanylate (c-di-GMP) cyclic compound, or a derivative thereof.

Optionally, the linker, as described herein is a cleavable linker. For example, the linker may include a disulfide bond or an acid-liable bond. In other examples, the linker may be self-immolating.

Other exemplary compositions are described below. For example, the composition comprising an immuno-stimulatory compound and a pHLIP® peptide is exemplified by the following structure: Peptide-Linker-ISC. In one option, the composition further comprises a modulator of polarity.

In other examples, the composition described herein includes 2 or more pHLIP® peptides. For example, the composition comprising 2 or more pHLIP® peptides has the following structure: Peptide1-Link-Peptide2. In aspects, the "Peptide1" is a first pHLIP® peptide comprising the sequence ADQDNPWRAYLDLLFPTDTLLLDLLWXA (SEQ ID NO: 1) or ADQDNPWRAYLDLLFPTDTLLLD-LLWXA (SEQ ID NO: 214), "Peptide2" is a second pHLIP® peptide comprising the sequence ADDQNP- WRAYLDLLFPTDTLLLDLLWXA (SEQ ID NO: 1) or ADQDNPWRAYLDLLFPTDTLLLDLLWXA (SEQ ID NO: 214). For example, "X" indicates any amino acid residue, including include a lysine (Lys), a cysteine (Cys), or an Azido-containing amino acid, "Link" is a polyethylene glycol linker, and each "—" is a covalent bond.

Methods of using the composition for treatment of cell proliferative disorders are also within the invention. In an aspect of the invention, provided herein is a method of augmenting an anti-tumor immune response, including administering to a subject a composition comprising an immuno-stimulatory compound and a pHLIP® peptide.

For example, the subject has a solid tumor. In other examples, the composition is injected directly into a tumor mass. Alternatively, the composition is systemically administered.

As described herein, the immuno-stimulatory compound is delivered into the cytosols of cancer cells. Additionally, the composition as described herein is delivered into the cytosol of a macrophage within the tumor microenvironment.

The immuno-stimulatory compound, as described herein, is delivered intracellularly to induce a biological effect. For example, the biological effect of the immuno-stimulatory compound is delivered in the presence of said pHLIP® is at least 20% greater than that delivered in the absence of said pHLIP®.

In some embodiments, the composition described herein targets the immune-stimulatory compound preferentially to a diseased tissue compared to a healthy tissue, thereby minimizing damage to said healthy tissue. In still other examples, the composition descried herein selectively promotes intracellular delivery of the immuno-stimulatory compound to cells in diseased tissue. Moreover, the composition described herein selectively promotes intracellular delivery of the immuno-stimulatory compound into a cancer cell, or into macrophages in a tumor microenvironment, or into a macrophage in a diseased tissue environment.

As provided herein, the methods of augmenting an anti-tumor immune response, including administering to a subject a composition comprising an immuno-stimulatory compound and a pHLIP® peptide, further include that the pHLIP® peptide comprises the amino acid sequence of Var3 pHLIP® ADDQNPWRAYLDLLFPTDTLLLDLLWCA (SEQ ID NO: 10), ADQDNPWRAYLDLLFPTDTLLLD-LLWCA (SEQ ID NO: 212) or variations thereof.

In some examples, the pHLIP® peptide comprises the a Var3 sequence with the amino acid sequence of AXDDQNP-WRAYLDLLFPTDTLLLDLLWXA (SEQ ID NO: 2) or ADQDNPWRAYLDLLFPTDTLLLDLLWXA (SEQ ID NO: 214), wherein X is, selected from a lysine (Lys), a cysteine (Cys), or an Azido-containing amino acid.

General Definitions

Unless specifically defined otherwise, all technical and scientific terms used herein shall be taken to have the same meaning as commonly understood by one of ordinary skill in the art (e.g., in cell culture, molecular genetics, and biochemistry).

As used herein, the term "about" in the context of a numerical value or range means±10% of the numerical value or range recited or claimed, unless the context requires a more limited range.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to and including 5.0 mg.

A small molecule is a compound that is less than 2000 daltons in mass. The molecular mass of the small molecule is preferably less than 1000 daltons, more preferably less than 600 daltons, e.g., the compound is less than 500 daltons, 400 daltons, 300 daltons, 200 daltons, or 100 daltons.

As used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) or polypeptide is free of the amino acid sequences, or nucleic acid sequences that flank it in its naturally-occurring state. Purified also defines a degree of sterility that is safe for administration to a human subject, e.g., lacking infectious or toxic agents. A purified or isolated polynucleotide (ribonucleic acid (RNA) or deoxyribonucleic acid (DNA)) is free of the genes or sequences that flank it in its naturally-occurring state. A purified or isolated polypeptide is free of the amino acids or sequences that flank it in its naturally-occurring state.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

The terms "subject," "patient," "individual," and the like as used herein are not intended to be limiting and can be generally interchanged. That is, an individual described as a "patient" does not necessarily have a given disease, but may be merely seeking medical advice.

As used herein, the singular forms "a," "an," and "the" include the plural reference unless the context clearly dictates otherwise. Thus, for example, a reference to "a disease," "a disease state", or "a nucleic acid" is a reference to one or more such embodiments, and includes equivalents thereof known to those skilled in the art and so forth.

As used herein, "treating" encompasses, e.g., inhibition, regression, or stasis of the progression of a disorder. Treating also encompasses the prevention or amelioration of any symptom or symptoms of the disorder. As used herein, "inhibition" of disease progression or a disease complication in a subject means preventing or reducing the disease progression and/or disease complication in the subject.

As used herein, a "symptom" associated with a disorder includes any clinical or laboratory manifestation associated with the disorder, and is not limited to what the subject can feel or observe.

As used herein, "effective" when referring to an amount of a therapeutic compound refers to the quantity of the compound that is sufficient to yield a desired therapeutic response without undue adverse side effects (such as toxicity, irritation, or allergic response) commensurate with a reasonable benefit/risk ratio when used in the manner of this disclosure.

As used herein, "pharmaceutically acceptable" carrier or excipient refers to a carrier or excipient that is suitable for use with humans and/or animals without undue adverse side effects (such as toxicity, irritation, and allergic response) commensurate with a reasonable benefit/risk ratio. It can be, e.g., a pharmaceutically acceptable solvent, suspending agent or vehicle, for delivering the instant compounds to the subject.

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "identical" or percent "identity," in the context of two or more nucleic acids or polypeptide sequences, refer to two or more sequences or subsequences that are the same or have a specified percentage of amino acid residues or nucleotides that are the same (e.g., 50%, 55%, 60%, 65%, 70%, 75%, 80%, 85%, 90%, 91%, 92%, 93%, 94%, 95%, 96%, 97%, 98%, 99%, or more identity over a specified region, e.g., of an entire polypeptide sequence or an individual domain thereof), when compared and aligned for maximum correspondence over a comparison window, or designated region as measured using a sequence comparison algorithm or by manual alignment and visual inspection. Such sequences that are at least about 80% identical are said to be "substantially identical." In some embodiments, two sequences are 100% identical. In certain embodiments, two sequences are 100% identical over the entire length of one of the sequences (e.g., the shorter of the two sequences where the sequences have different lengths). In various embodiments, identity may refer to the complement of a test sequence. In some embodiments, the identity exists over a region that is at least about 10 to about 100, about 20 to about 75, about 30 to about 50 amino acids or nucleotides in length. In certain embodiments, the identity exists over a region that is at least about 50 amino acids in length, or more preferably over a region that is 100 to 500, 100 to 200, 150 to 200, 175 to 200, 175 to 225, 175 to 250, 200 to 225, 200 to 250 or more amino acids in length.

For sequence comparison, typically one sequence acts as a reference sequence, to which test sequences are compared. In various embodiments, when using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A the "comparison window" refers to a segment of any one of the number of contiguous positions (e.g., least about 10 to about 100, about 20 to about 75, about 30 to about 50, 100 to 500, 100 to 200, 150 to 200, 175 to 200, 175 to 225, 175 to 250, 200 to 225, 200 to 250) in which a sequence may be compared to a reference sequence of the same number of contiguous positions after the two sequences are optimally aligned. In various embodiments, a comparison window is the entire length of one or both of two aligned sequences. In some embodiments, two sequences being compared comprise different lengths, and the comparison window is the entire length of the longer or the shorter of the two sequences. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

In various embodiments, an algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. BLAST and BLAST 2.0 may be used, with the parameters described herein, to determine percent sequence identity for nucleic acids and proteins. Software for performing BLAST analyses is publicly available through the National Center for Biotechnology Information, as known in the art. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=-4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=-4, and a comparison of both strands.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A composition comprising an immuno-stimulatory compound (ISC) and a pH low insertion peptide (pHLIP) peptide, wherein said ISC is selected from a group consisting of:
   (i) a cyclic dinucleotide (CDN),
   (ii) a cyclic purine dinucleotide,
   (iii) a cyclic purine dinucleotide which binds to stimulator of interferon genes (STING),
   (iv) a cGAMP,
   (v) a 3',5'-cyclic diadenylic acid (c-di-AMP), and
   (vi) a cyclic diguanylate (c-di-GMP) cyclic compound.

2. The composition of claim 1, comprising the following structure:
   Peptide-Linker-ISC
   wherein "Peptide" is a pHLIP peptide comprising the sequence ADQDNPWRAYLDLLFPTDTLLLDLLWCA (SEQ ID NO: 212)
   or
   ADDQNPWRAYLDLLFPTDTLLLDLLWCA (SEQ ID NO: 10)
   or
   ADQDNPWRAYLDLLFPTDTLLLDLLWKA (SEQ ID NO: 213)
   or
   ADDQNPWRAYLDLLFPTDTLLLDLLWKA (SEQ ID NO: 217)

wherein "Linker" is a cleavable linker,
   wherein "ISC" is a cyclic purine dinucleotide which binds to stimulator of interferon genes (STING), and
   wherein each "—" is a covalent bond.

3. The composition of claim 2, wherein said linker comprises a disulfide bond or an acid-labile bond.

4. The composition of claim 2, wherein said linker is self-immolating.

5. The composition of claim 1, further comprising a modulator of polarity.

6. The composition of claim 1, wherein said composition comprises 2 or more pHLIP peptides.

7. The composition of claim 6, comprising the following structure:
   Peptide1-Link-Peptide2
   wherein "Peptide1" is a first pHLIP peptide comprising the sequence ADDQNPWRAYLDLLFPTDTLLLDLLWXA (SEQ ID NO: 1)
   or
   ADQDNPWRAYLDLLFPTDTLLLDLLWXA (SEQ ID NO: 214), wherein "Peptide2" is a second pHLIP peptide comprising the sequence ADDQNPWRAYLDLLFPTDTLLLDLLWXA (SEQ ID NO: 1)
   or
   ADQDNPWRAYLDLLFPTDTLLLDLLWXA (SEQ ID NO: 214), wherein "X" indicates any amino acid residue, including a lysine (Lys), a cysteine (Cys), or an Azido-containing amino acid,
   wherein "Link" is a polyethylene glycol linker, and
   wherein each "—" is a covalent bond.

8. A method of augmenting an anti-tumor immune response, comprising administering to a subject a composition comprising an immuno-stimulatory compound and a pHLIP peptide, wherein said immuno-stimulatory compound is selected from the group consisting of:
   (i) a cyclic dinucleotide (CDN),
   (ii) a cyclic purine dinucleotide,
   (iii) a cyclic purine dinucleotide which binds to stimulator of interferon genes (STING),
   (iv) a cGAMP,
   (v) a 3',5'-cyclic diadenylic acid (c-di-AMP), and
   (vi) a cyclic diguanylate (c-di-GMP) cyclic compound.

9. The method of claim 8, wherein said subject comprises a solid tumor.

10. The method of claim 8, wherein said composition is injected directly into a tumor mass.

11. The method of claim 8, wherein said composition is systemically administered.

12. The method of claim 8, wherein said immuno-stimulatory compound is delivered into the cytosols of cancer cells.

13. The method of claim 8, wherein said immuno-stimulatory compound is delivered into the cytosol of a macrophage within the tumor microenvironment.

14. The method of claim 8, wherein said immuno-stimulatory compound is delivered intracellularly to induce a biological effect.

15. The method of claim 14, wherein the biological effect of said immuno-stimulatory compound delivered in the presence of said pHLIP is at least 20% greater than that delivered in the absence of said pHLIP.

16. The method of claim 8, wherein said composition targets said immuno-stimulatory compound preferentially to a diseased tissue compared to a healthy tissue, thereby minimizing damage to said healthy tissue.

17. The method of claim 8, wherein said composition selectively promotes intracellular delivery of said immuno-stimulatory compound to cells in diseased tissue.

18. The method of claim 17, wherein said composition selectively promotes intracellular delivery of said immuno-stimulatory compound into a cancer cell.

19. The method of claim 8, wherein said composition selectively promotes intracellular delivery of said immuno-stimulatory compound into macrophages in a tumor microenvironment.

20. The method of claim 8, wherein said composition selectively promotes intracellular delivery of said immuno-stimulatory compound into a macrophage in a diseased tissue environment.

21. The method of claim 8, wherein said pHLIP peptide comprises the amino acid sequence of

```
                                         (SEQ ID NO: 10)
ADDQNPWRAYLDLLFPTDTLLLDLLWCA
or
                                         (SEQ ID NO: 212)
ADQDNPWRAYLDLLFPTDTLLLDLLWCA.
```

22. The method of claim 8, wherein the composition comprises the following structure:

Peptide-Link-ISC wherein "Peptide" us a pHLIP peptide comprising an amino acid sequence of

```
                                          (SEQ ID NO: 2)
AXDDQNPWRAYLDLLFPTDTLLLDLLWXA
or
                                        (SEQ ID NO: 214)
ADQDNPWRAYLDLLFPTDTLLLDLLWXA,
``` wherein "X" is, selected from a lysine (Lys), a cysteine (Cys), or an Azido-containing amino acid, wherein "Link" is a polyethylene glycol linker, wherein "ISC" is said immuno-stimulatory compound, and wherein each "—" is a covalent bond.

* * * * *

SEQUENCE LISTING

```
<160> NUMBER OF SEQ ID NOS: 217

<210> SEQ ID NO 1
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (27)..(27)
<223> OTHER INFORMATION: Any amino acid
<220> FEATURE:
<223> OTHER INFORMATION: See specification as filed for detailed
      description of substitutions and preferred embodiments

<400> SEQUENCE: 1

Ala Asp Asp Gln Asn Pro Trp Arg Ala Tyr Leu Asp Leu Leu Phe Pro
1               5                  10                  15

Thr Asp Thr Leu Leu Leu Asp Leu Leu Trp Xaa Ala
            20                  25

<210> SEQ ID NO 2
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Lys, Cys or an Azido-containing amino acid
<220> FEATURE:
<221> NAME/KEY: MOD_RES
<222> LOCATION: (28)..(28)
<223> OTHER INFORMATION: Lys, Cys or an Azido-containing amino acid
```

```
<220> FEATURE:
<223> OTHER INFORMATION: See specification as filed for detailed
      description of substitutions and preferred embodiments

<400> SEQUENCE: 2

Ala Xaa Asp Asp Gln Asn Pro Trp Arg Ala Tyr Leu Asp Leu Leu Phe
1               5                   10                  15

Pro Thr Asp Thr Leu Leu Leu Asp Leu Leu Trp Xaa Ala
            20                  25

<210> SEQ ID NO 3
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Ala Glu Gln Asn Pro Ile Tyr Trp Ala Arg Tyr Ala Asp Trp Leu Phe
1               5                   10                  15

Thr Thr Pro Leu Leu Leu Leu Asp Leu Ala Leu Leu Val Asp Ala Asp
            20                  25                  30

Glu Gly Thr
        35

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Glu Gln Asn Pro Ile Tyr
1               5

<210> SEQ ID NO 5
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Trp Ala Arg Tyr Ala Asp Trp Leu Phe Thr Thr Pro Leu Leu Leu Leu
1               5                   10                  15

Asp Leu Ala Leu Leu Val
            20

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Ala Asp Glu Gly Thr
1               5

<210> SEQ ID NO 7
```

```
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr
        35

<210> SEQ ID NO 8
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Ala Glu Gln Asn Pro Ile Tyr Trp Ala Arg Tyr Ala Asp Trp Leu Phe
1               5                   10                  15

Thr Thr Pro Leu Leu Leu Leu Asp Leu Ala Leu Leu Val Asp Ala Asp
            20                  25                  30

Glu Gly Thr
        35

<210> SEQ ID NO 9
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Ala Ala Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 10
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Asp Asp Gln Asn Pro Trp Arg Ala Tyr Leu Asp Leu Leu Phe Pro
1               5                   10                  15

Thr Asp Thr Leu Leu Leu Asp Leu Leu Trp Cys Ala
            20                  25

<210> SEQ ID NO 11
<211> LENGTH: 38
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 11

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 12
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ala Cys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Gly
        35

<210> SEQ ID NO 13
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ala Cys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr
        35

<210> SEQ ID NO 14
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ala Lys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr
        35

<210> SEQ ID NO 15
<211> LENGTH: 37

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ala Lys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Gly
        35

<210> SEQ ID NO 16
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ala Ala Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Lys Cys Gly
        35

<210> SEQ ID NO 17
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ala Lys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Cys Thr
        35

<210> SEQ ID NO 18
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ala Cys Glu Gln Asn Pro Ile Tyr Trp Ala Arg Tyr Ala Asn Trp Leu
1               5                   10                  15

Phe Thr Thr Pro Leu Leu Leu Leu Asn Leu Ala Leu Leu Val Asp Ala
            20                  25                  30

Asp Glu Gly Thr Gly
        35

<210> SEQ ID NO 19
```

```
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ala Cys Glu Gln Asn Pro Ile Tyr Trp Ala Arg Tyr Ala Asn Trp Leu
1               5                   10                  15

Phe Thr Thr Pro Leu Leu Leu Leu Asn Leu Ala Leu Leu Val Asp Ala
            20                  25                  30

Asp Glu Gly Thr
        35

<210> SEQ ID NO 20
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ala Cys Glu Gln Asn Pro Ile Tyr Trp Ala Arg Tyr Ala Lys Trp Leu
1               5                   10                  15

Phe Thr Thr Pro Leu Leu Leu Leu Lys Leu Ala Leu Leu Val Asp Ala
            20                  25                  30

Asp Glu Gly Thr Gly
        35

<210> SEQ ID NO 21
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asn Ala
            20                  25                  30

Asn Gln Gly Thr
        35

<210> SEQ ID NO 22
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Ala Ala Glu Gln Asn Pro Ile Tyr Trp Ala Arg Tyr Ala Asp Trp Leu
1               5                   10                  15

Phe Thr Thr Pro Leu Leu Leu Leu Ala Leu Ala Leu Leu Val Asp Ala
            20                  25                  30

Asp Glu Gly Thr
        35
```

```
<210> SEQ ID NO 23
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ala Ala Glu Gln Asn Pro Ile Tyr Trp Ala Arg Tyr Ala Asp Trp Leu
1               5                   10                  15

Phe Thr Thr Pro Leu Leu Leu Leu Glu Leu Ala Leu Leu Val Asp Ala
                20                  25                  30

Asp Glu Gly Thr Lys Cys Gly
            35

<210> SEQ ID NO 24
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Ala Ala Glu Gln Asn Pro Ile Tyr Trp Ala Arg Tyr Ala Ala Trp Leu
1               5                   10                  15

Phe Thr Thr Pro Leu Leu Leu Leu Asp Leu Ala Leu Leu Val Asp Ala
                20                  25                  30

Asp Glu Gly Thr
            35

<210> SEQ ID NO 25
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ala Ala Glu Gln Asn Pro Ile Tyr Trp Ala Arg Tyr Ala Asp Trp Leu
1               5                   10                  15

Phe Thr Thr Ala Leu Leu Leu Leu Asp Leu Ala Leu Leu Val Asp Ala
                20                  25                  30

Asp Glu Gly Thr
            35

<210> SEQ ID NO 26
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ala Ala Glu Gln Asn Pro Ile Tyr Trp Ala Arg Tyr Ala Asp Trp Leu
1               5                   10                  15

Phe Thr Thr Pro Leu Leu Leu Leu Glu Leu Ala Leu Leu Val Asp Ala
                20                  25                  30

Asp Glu Gly Thr
            35
```

<210> SEQ ID NO 27
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Ala Ala Glu Gln Asn Pro Ile Tyr Trp Ala Arg Tyr Ala Glu Trp Leu
1               5                   10                  15

Phe Thr Thr Pro Leu Leu Leu Asp Leu Ala Leu Leu Val Asp Ala
            20                  25                  30

Asp Glu Gly Thr
        35

<210> SEQ ID NO 28
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Ala Ala Glu Gln Asn Pro Ile Ile Tyr Trp Ala Arg Tyr Ala Asp Trp
1               5                   10                  15

Leu Phe Thr Asp Leu Pro Leu Leu Leu Asp Leu Leu Ala Leu Leu
            20                  25                  30

Val Asp Ala Asp Glu Gly Thr
        35

<210> SEQ ID NO 29
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gly Glu Gln Asn Pro Ile Tyr Trp Ala Gln Tyr Ala Asp Trp Leu Phe
1               5                   10                  15

Thr Thr Pro Leu Leu Leu Asp Leu Ala Leu Leu Val Asp Ala Asp
            20                  25                  30

Glu Gly Thr Cys Gly
        35

<210> SEQ ID NO 30
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gly Gly Glu Gln Asn Pro Ile Tyr Trp Ala Arg Tyr Ala Asp Trp Leu
1               5                   10                  15

Phe Thr Thr Pro Leu Leu Leu Asp Leu Leu Ala Leu Leu Val Asp Ala
            20                  25                  30

Asp Glu Gly Thr Cys Gly
        35

```
<210> SEQ ID NO 31
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Ala Leu Leu Val Asp Ala
            20                  25                  30

Asp Glu Gly Thr Cys Gly
        35

<210> SEQ ID NO 32
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gly Gly Glu Gln Asn Pro Ile Tyr Trp Ala Arg Tyr Asp Ala Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 33
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gly Gly Glu Gln Asn Pro Ile Tyr Trp Ala Arg Tyr Ala Trp Asp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 34
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Ala Ala Glu Gln Asn Pro Ile Tyr Trp Ala Arg Tyr Ala Asp Trp Leu
1               5                   10                  15

Phe Thr Thr Gly Leu Leu Leu Leu Asp Leu Ala Leu Leu Val Asp Ala
            20                  25                  30

Asp Glu Gly Thr
```

<210> SEQ ID NO 35
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Asp Asp Asp Glu Asp Asn Pro Ile Tyr Trp Ala Arg Tyr Ala Asp Trp
1               5                   10                  15

Leu Phe Thr Thr Pro Leu Leu Leu Leu His Gly Ala Leu Leu Val Asp
            20                  25                  30

Ala Asp Glu Cys Thr
        35

<210> SEQ ID NO 36
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Asp Asp Glu Asp Asn Pro Ile Tyr Trp Ala Arg Tyr Ala Asp Trp
1               5                   10                  15

Leu Phe Thr Thr Pro Leu Leu Leu Leu His Gly Ala Leu Leu Val Asp
            20                  25                  30

Ala Asp Glu Thr
        35

<210> SEQ ID NO 37
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asp
            20                  25                  30

Ala Asp Glu Gly Cys Thr
        35

<210> SEQ ID NO 38
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Cys Asp Asp Asp Glu Asp Asn Pro Ile Tyr Trp Ala Arg Tyr Ala His
1               5                   10                  15

Trp Leu Phe Thr Thr Pro Leu Leu Leu Leu His Gly Ala Leu Leu Val
            20                  25                  30

Asp Ala Asp Glu Thr
        35

<210> SEQ ID NO 39
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asp
            20                  25                  30

Ala Asp Glu Gly Thr
        35

<210> SEQ ID NO 40
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
            20                  25                  30

Ala Asp Glu Cys Thr
        35

<210> SEQ ID NO 41
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Asp Asp Asp Glu Asp Asn Pro Ile Tyr Trp Ala Arg Tyr Ala His Trp
1               5                   10                  15

Leu Phe Thr Thr Pro Leu Leu Leu His Gly Ala Leu Leu Val Asn
            20                  25                  30

Ala Asp Glu Gly Thr
        35

<210> SEQ ID NO 42
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
            20                  25                  30

Ala Asn Glu Cys Thr
        35

<210> SEQ ID NO 43
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Asp Asp Asp Glu Asp Asn Pro Ile Tyr Trp Ala Arg Tyr Ala His Trp
1               5                  10                  15

Leu Phe Thr Thr Pro Leu Leu Leu Leu His Gly Ala Leu Leu Val Asn
                20                  25                  30

Ala Asn Glu Gly Thr
        35

<210> SEQ ID NO 44
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Ala Glu Gln Asn Pro Ile Tyr Trp Ala Arg Tyr Ala Asp Phe Leu Phe
1               5                  10                  15

Thr Thr Pro Leu Leu Leu Leu Asp Leu Ala Leu Leu Val Asp Ala Asp
                20                  25                  30

Glu Thr

<210> SEQ ID NO 45
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Ala Glu Gln Asn Pro Ile Tyr Phe Ala Arg Tyr Ala Asp Trp Leu Phe
1               5                  10                  15

Thr Thr Pro Leu Leu Leu Leu Asp Leu Ala Leu Leu Val Asp Ala Asp
                20                  25                  30

Glu Gly Thr
        35

<210> SEQ ID NO 46
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Ala Glu Gln Asn Pro Ile Tyr Phe Ala Arg Tyr Ala Asp Phe Leu Phe
1               5                  10                  15

Thr Thr Pro Leu Leu Leu Leu Asp Leu Ala Leu Leu Trp Asp Ala Asp
                20                  25                  30

Glu Thr

<210> SEQ ID NO 47
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

```
Ala Lys Glu Asp Gln Asn Pro Tyr Trp Ala Arg Tyr Ala Asp Trp Leu
1               5                   10                  15

Phe Thr Thr Pro Leu Leu Leu Leu Asp Leu Ala Leu Leu Val Asp Gly
            20                  25                  30
```

<210> SEQ ID NO 48
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

```
Ala Cys Glu Asp Gln Asn Pro Tyr Trp Ala Arg Tyr Ala Asp Trp Leu
1               5                   10                  15

Phe Thr Thr Pro Leu Leu Leu Leu Asp Leu Ala Leu Leu Val Asp Gly
            20                  25                  30
```

<210> SEQ ID NO 49
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

```
Ala Glu Asp Gln Asn Pro Tyr Trp Ala Arg Tyr Ala Asp Trp Leu Phe
1               5                   10                  15

Thr Thr Pro Leu Leu Leu Leu Asp Leu Ala Leu Leu Val Asp Cys Gly
            20                  25                  30
```

<210> SEQ ID NO 50
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

```
Ala Glu Asp Gln Asn Pro Tyr Trp Ala Arg Tyr Ala Asp Trp Leu Phe
1               5                   10                  15

Thr Thr Pro Leu Leu Leu Glu Leu Ala Leu Leu Val Glu Cys Gly
            20                  25                  30
```

<210> SEQ ID NO 51
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Ala Lys Glu Asp Gln Asn Asp Pro Tyr Trp Ala Arg Tyr Ala Asp Trp
1               5                   10                  15

Leu Phe Thr Thr Pro Leu Leu Leu Asp Leu Ala Leu Leu Val Gly
            20                  25                  30

<210> SEQ ID NO 52
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Ala Lys Glu Asp Gln Asn Pro Tyr Trp Arg Ala Tyr Ala Asp Leu Phe
1               5                   10                  15

Thr Pro Leu Thr Leu Leu Asp Leu Leu Ala Leu Trp Asp Gly
            20                  25                  30

<210> SEQ ID NO 53
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Ala Glu Asp Gln Asn Pro Tyr Trp Ala Arg Tyr Ala Asp Trp Leu Phe
1               5                   10                  15

Thr Thr Pro Leu Leu Leu Leu Glu Leu Ala Leu Leu Val Cys Gly
            20                  25                  30

<210> SEQ ID NO 54
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Ala Cys Glu Asp Gln Asn Pro Tyr Trp Arg Ala Tyr Ala Asp Leu Phe
1               5                   10                  15

Thr Pro Leu Thr Leu Leu Asp Leu Leu Ala Leu Trp Asp Gly
            20                  25                  30

<210> SEQ ID NO 55
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ala Cys Asp Asp Gln Asn Pro Trp Arg Ala Tyr Leu Asp Leu Leu Phe
1               5                   10                  15

Pro Thr Asp Thr Leu Leu Leu Asp Leu Leu Trp
            20                  25

<210> SEQ ID NO 56

```
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ala Lys Asp Asp Gln Asn Pro Trp Arg Ala Tyr Leu Asp Leu Leu Phe
1               5                   10                  15

Pro Thr Asp Thr Leu Leu Leu Asp Leu Leu Trp Cys
            20                  25

<210> SEQ ID NO 57
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ala Cys Glu Glu Gln Asn Pro Trp Arg Ala Tyr Leu Glu Leu Leu Phe
1               5                   10                  15

Pro Thr Glu Thr Leu Leu Leu Glu Leu Leu Trp
            20                  25

<210> SEQ ID NO 58
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ala Cys Asp Asp Gln Asn Pro Trp Ala Arg Tyr Leu Asp Trp Leu Phe
1               5                   10                  15

Pro Thr Asp Thr Leu Leu Leu Asp Leu
            20                  25

<210> SEQ ID NO 59
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Cys Asp Asn Asn Asn Pro Trp Arg Ala Tyr Leu Asp Leu Leu Phe Pro
1               5                   10                  15

Thr Asp Thr Leu Leu Leu Asp Trp
            20

<210> SEQ ID NO 60
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Cys Glu Glu Gln Gln Pro Trp Ala Gln Tyr Leu Glu Leu Leu Phe Pro
1               5                   10                  15
```

```
Thr Glu Thr Leu Leu Leu Glu Trp
            20

<210> SEQ ID NO 61
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Cys Glu Glu Gln Gln Pro Trp Arg Ala Tyr Leu Glu Leu Leu Phe Pro
1               5                   10                  15

Thr Glu Thr Leu Leu Leu Glu Trp
            20

<210> SEQ ID NO 62
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Cys Asp Asp Asp Asp Asn Pro Asn Tyr Trp Ala Arg Tyr Ala Asn
1               5                   10                  15

Trp Leu Phe Thr Thr Pro Leu Leu Leu Asn Gly Ala Leu Leu Val
            20                  25                  30

Glu Ala Glu Glu Thr
        35

<210> SEQ ID NO 63
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Cys Asp Asp Asp Asp Asn Pro Asn Tyr Trp Ala Arg Tyr Ala Pro
1               5                   10                  15

Trp Leu Phe Thr Thr Pro Leu Leu Leu Pro Gly Ala Leu Leu Val
            20                  25                  30

Glu Ala Glu Glu
        35

<210> SEQ ID NO 64
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Thr Glu Asp Ala Asp Val Leu Leu Ala Leu Asp Leu Leu Leu Leu Pro
1               5                   10                  15

Thr Thr Phe Leu Trp Asp Ala Tyr Arg Ala Trp Tyr Pro Asn Gln Glu
            20                  25                  30

Cys Ala
```

<210> SEQ ID NO 65
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ala Glu Gln Asn Pro Ile Tyr Trp Ala Arg Tyr Ala Asp Trp Leu Phe
1               5                   10                  15

Thr Thr Pro Leu
            20

<210> SEQ ID NO 66
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ala Glu Gln Asn Pro Ile Tyr Trp Ala Arg Tyr Ala Asp Trp Leu Phe
1               5                   10                  15

Thr Thr Pro Cys Leu
            20

<210> SEQ ID NO 67
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ala Cys Glu Gln Asn Pro Ile Tyr Trp Ala Arg Tyr Ala Asp Trp Leu
1               5                   10                  15

Phe Thr Thr Pro Leu
            20

<210> SEQ ID NO 68
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ala Glu Gln Asn Pro Ile Tyr Phe Ala Arg Tyr Ala Asp Trp Leu Phe
1               5                   10                  15

Thr Thr Pro Leu
            20

<210> SEQ ID NO 69
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ala Glu Gln Asn Pro Ile Tyr Phe Ala Arg Tyr Ala Asp Leu Leu Phe
1               5                   10                  15

Pro Thr Thr Leu Ala Trp
            20

<210> SEQ ID NO 70
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ala Glu Gln Asn Pro Ile Tyr Trp Ala Arg Tyr Ala Asp Leu Leu Phe
1               5                   10                  15

Pro Thr Thr Leu Ala Phe
            20

<210> SEQ ID NO 71
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ala Glu Gln Asn Pro Ile Tyr Trp Ala Arg Tyr Ala Asp Leu Leu Phe
1               5                   10                  15

Pro Thr Thr Leu Ala Trp
            20

<210> SEQ ID NO 72
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Lys Glu Asp Gln Asn Pro Trp Ala Arg Tyr Ala Asp Leu Leu Phe Pro
1               5                   10                  15

Thr Thr Leu Ala Trp
            20

<210> SEQ ID NO 73
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Lys Glu Asp Gln Asn Pro Trp Ala Arg Tyr Ala Asp Leu Leu Phe Pro
1               5                   10                  15

Thr Thr Leu Trp
            20

<210> SEQ ID NO 74
<211> LENGTH: 22
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 74

Ala Cys Glu Asp Gln Asn Pro Trp Ala Arg Tyr Ala Asp Leu Leu Phe
1               5                   10                  15

Pro Thr Thr Leu Ala Trp
            20

<210> SEQ ID NO 75
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ala Cys Glu Asp Gln Asn Pro Trp Ala Arg Tyr Ala Asp Trp Leu Phe
1               5                   10                  15

Pro Thr Thr Leu Leu Leu Leu Asp
            20

<210> SEQ ID NO 76
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ala Cys Glu Glu Gln Asn Pro Trp Ala Arg Tyr Ala Glu Leu Leu Phe
1               5                   10                  15

Pro Thr Thr Leu Ala Trp
            20

<210> SEQ ID NO 77
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ala Cys Glu Glu Gln Asn Pro Trp Ala Arg Tyr Ala Glu Trp Leu Phe
1               5                   10                  15

Pro Thr Thr Leu Leu Leu Leu Glu
            20

<210> SEQ ID NO 78
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ala Cys Glu Glu Gln Asn Pro Trp Ala Arg Tyr Leu Glu Trp Leu Phe
1               5                   10                  15

Pro Thr Glu Thr Leu Leu Leu Glu Leu
```

```
                    20                  25

<210> SEQ ID NO 79
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ala Cys Glu Glu Gln Asn Pro Gln Ala Glu Tyr Ala Glu Trp Leu Phe
1               5                   10                  15

Pro Thr Thr Leu Leu Leu Leu Glu
                    20

<210> SEQ ID NO 80
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 80

Trp Ala Arg Tyr Ala Asp Trp Leu Phe Thr Thr Pro Leu Leu Leu Leu
1               5                   10                  15

Asp Leu Ala Leu Leu
                    20

<210> SEQ ID NO 81
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 81

Tyr Ala Arg Tyr Ala Asp Trp Leu Phe Thr Thr Pro Leu Leu Leu Leu
1               5                   10                  15

Asp Leu Ala Leu Leu
                    20

<210> SEQ ID NO 82
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 82

Trp Ala Arg Tyr Ser Asp Trp Leu Phe Thr Thr Pro Leu Leu Leu Tyr
1               5                   10                  15

Asp Leu Gly Leu Leu
                    20
```

<210> SEQ ID NO 83
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 83

Trp Ala Arg Tyr Thr Asp Trp Phe Thr Thr Pro Leu Leu Leu Tyr Asp
1               5                   10                  15

Leu Ala Leu Leu Ala
            20

<210> SEQ ID NO 84
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 84

Trp Ala Arg Tyr Thr Asp Trp Leu Phe Thr Thr Pro Leu Leu Leu Tyr
1               5                   10                  15

Asp Leu Gly Leu Leu
            20

<210> SEQ ID NO 85
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 85

Trp Ala Arg Tyr Ala Asp Trp Leu Phe Thr Thr Pro Leu Leu Leu Leu
1               5                   10                  15

Asp Leu Ser Leu Leu
            20

<210> SEQ ID NO 86
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 86

Leu Leu Ala Leu Asp Leu Leu Leu Pro Thr Thr Phe Leu Trp Asp
1               5                   10                  15

Ala Tyr Arg Ala Trp
            20

```
<210> SEQ ID NO 87
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 87

Leu Leu Ala Leu Asp Leu Leu Leu Pro Thr Thr Phe Leu Trp Asp
1               5                   10                  15

Ala Tyr Arg Ala Tyr
            20

<210> SEQ ID NO 88
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 88

Leu Leu Gly Leu Asp Tyr Leu Leu Pro Thr Thr Phe Leu Trp Asp
1               5                   10                  15

Ser Tyr Arg Ala Trp
            20

<210> SEQ ID NO 89
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 89

Ala Leu Leu Ala Leu Asp Tyr Leu Leu Leu Pro Thr Thr Phe Trp Asp
1               5                   10                  15

Thr Tyr Arg Ala Trp
            20

<210> SEQ ID NO 90
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 90

Leu Leu Gly Leu Asp Tyr Leu Leu Pro Thr Thr Phe Leu Trp Asp
1               5                   10                  15

Thr Tyr Arg Ala Trp
```

20

<210> SEQ ID NO 91
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 91

Leu Leu Ser Leu Asp Leu Leu Leu Leu Pro Thr Thr Phe Leu Trp Asp
1               5                   10                  15

Ala Tyr Arg Ala Trp
            20

<210> SEQ ID NO 92
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 92

Gly Leu Ala Gly Leu Leu Gly Leu Glu Gly Leu Leu Gly Leu Pro Leu
1               5                   10                  15

Gly Leu Leu Glu Gly Leu Trp Leu Gly Leu
            20                  25

<210> SEQ ID NO 93
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 93

Leu Gly Leu Trp Leu Gly Glu Leu Leu Gly Leu Pro Leu Gly Leu Leu
1               5                   10                  15

Gly Glu Leu Gly Leu Leu Gly Ala Leu Gly
            20                  25

<210> SEQ ID NO 94
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 94

Trp Arg Ala Tyr Leu Asp Leu Leu Phe Pro Thr Asp Thr Leu Leu Leu
1               5                   10                  15

```
Asp Leu Leu Trp
            20

<210> SEQ ID NO 95
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 95

Trp Leu Leu Asp Leu Leu Thr Asp Thr Pro Phe Leu Leu Asp Leu
1               5                   10                  15

Tyr Ala Arg Trp
            20

<210> SEQ ID NO 96
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 96

Trp Ala Arg Tyr Leu Glu Trp Leu Phe Pro Thr Glu Thr Leu Leu Leu
1               5                   10                  15

Glu Leu

<210> SEQ ID NO 97
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 97

Trp Ala Gln Tyr Leu Glu Leu Leu Phe Pro Thr Glu Thr Leu Leu Leu
1               5                   10                  15

Glu Trp

<210> SEQ ID NO 98
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 98

Leu Glu Leu Leu Leu Thr Glu Thr Pro Phe Leu Trp Glu Leu Tyr Arg
1               5                   10                  15

Ala Trp
```

```
<210> SEQ ID NO 99
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 99

Trp Glu Leu Leu Leu Thr Glu Thr Pro Phe Leu Leu Glu Leu Tyr Gln
1               5                   10                  15

Ala Trp

<210> SEQ ID NO 100
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 100

Trp Leu Phe Thr Thr Pro Leu Leu Leu Leu Asn Gly Ala Leu Leu Val
1               5                   10                  15

Glu

<210> SEQ ID NO 101
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 101

Trp Leu Phe Thr Thr Pro Leu Leu Leu Leu Pro Gly Ala Leu Leu Val
1               5                   10                  15

Glu

<210> SEQ ID NO 102
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 102

Trp Ala Arg Tyr Ala Asp Leu Leu Phe Pro Thr Thr Leu Ala Trp
1               5                   10                  15

<210> SEQ ID NO 103
<211> LENGTH: 17
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 103

Glu Val Leu Leu Ala Gly Asn Leu Leu Leu Leu Pro Thr Thr Phe Leu
1               5                   10                  15

Trp

<210> SEQ ID NO 104
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 104

Glu Val Leu Leu Ala Gly Pro Leu Leu Leu Leu Pro Thr Thr Phe Leu
1               5                   10                  15

Trp

<210> SEQ ID NO 105
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 105

Trp Ala Leu Thr Thr Pro Phe Leu Leu Asp Ala Tyr Arg Ala Trp
1               5                   10                  15

<210> SEQ ID NO 106
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 106

Asn Leu Glu Gly Phe Phe Ala Thr Leu Gly Gly Glu Ile Ala Leu Trp
1               5                   10                  15

Ser Leu Val Val Leu Ala Ile Glu
            20

<210> SEQ ID NO 107
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: See specification as filed for detailed
      description of substitutions and preferred embodiments

<400> SEQUENCE: 107

Glu Gly Phe Phe Ala Thr Leu Gly Gly Glu Ile Ala Leu Trp Ser Asp
1               5                   10                  15

Val Val Leu Ala Ile Glu
            20

<210> SEQ ID NO 108
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 108

Glu Gly Phe Phe Ala Thr Leu Gly Gly Glu Ile Pro Leu Trp Ser Asp
1               5                   10                  15

Val Val Leu Ala Ile Glu
            20

<210> SEQ ID NO 109
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 109

Glu Ile Ala Leu Val Val Leu Ser Trp Leu Ala Ile Glu Gly Gly Leu
1               5                   10                  15

Thr Ala Phe Phe Gly Glu Leu Asn
            20

<210> SEQ ID NO 110
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 110

Glu Ile Ala Leu Val Val Asp Ser Trp Leu Ala Ile Glu Gly Gly Leu
1               5                   10                  15

Thr Ala Phe Phe Gly Glu
            20

<210> SEQ ID NO 111
<211> LENGTH: 22
<212> TYPE: PRT
<213> ORGANISM: Artificial Sequence
<220> FEATURE:
<223> OTHER INFORMATION: Description of Artificial Sequence: Synthetic
```

```
             peptide
<220> FEATURE:
<223> OTHER INFORMATION: See specification as filed for detailed
      description of substitutions and preferred embodiments

<400> SEQUENCE: 111

Glu Ile Ala Leu Val Val Asp Ser Trp Leu Pro Ile Glu Gly Gly Leu
1               5                   10                  15

Thr Ala Phe Phe Gly Glu
            20

<210> SEQ ID NO 112
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 112

Ile Leu Asp Leu Val Phe Gly Leu Leu Phe Ala Val Thr Ser Val Asp
1               5                   10                  15

Phe Leu Val Gln Trp
            20

<210> SEQ ID NO 113
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 113

Trp Gln Val Leu Phe Asp Val Ser Thr Val Ala Phe Leu Leu Gly Phe
1               5                   10                  15

Val Leu Asp Leu Ile
            20

<210> SEQ ID NO 114
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Ala Glu Gln Asn Pro Ile Tyr Trp Ala Arg Tyr Ala Asp Trp Leu Phe
1               5                   10                  15

Thr Thr Pro Leu Leu Leu Leu Asp Leu Ala Leu Leu Val Asp Ala Asp
            20                  25                  30

Glu Thr

<210> SEQ ID NO 115
<211> LENGTH: 34
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 115

Ala Glu Gln Asn Pro Ile Tyr Trp Ala Arg Tyr Ala Glu Trp Leu Phe
1               5                   10                  15

Thr Thr Pro Leu Leu Leu Leu Glu Leu Ala Leu Leu Val Glu Ala Glu
            20                  25                  30

Glu Thr

<210> SEQ ID NO 116
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Ala Asp Asp Gln Asn Pro Trp Arg Ala Tyr Leu Asp Leu Phe Pro
1               5                   10                  15

Asp Thr Thr Asp Leu Leu Leu Leu Asp Leu Leu Trp Asp Ala Asp Glu
            20                  25                  30

Thr

<210> SEQ ID NO 117
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Ala Glu Glu Gln Asn Pro Trp Arg Ala Tyr Leu Glu Leu Leu Phe Pro
1               5                   10                  15

Glu Thr Thr Glu Leu Leu Leu Leu Glu Leu Leu Trp Glu Ala Glu Glu
            20                  25                  30

Thr

<210> SEQ ID NO 118
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (13)..(13)
<223> OTHER INFORMATION: Gla

<400> SEQUENCE: 118

Ala Glu Gln Asn Pro Ile Tyr Trp Ala Arg Tyr Ala Xaa Trp Leu Phe
1               5                   10                  15

Thr Thr Pro Leu Leu Leu Leu Asp Leu Ala Leu Leu Val Asp Ala Asp
            20                  25                  30

Glu Thr

<210> SEQ ID NO 119
<211> LENGTH: 34
<212> TYPE: PRT
<213> ORGANISM: Artificial Sequence
<220> FEATURE:

```
<223> OTHER INFORMATION: Description of Artificial Sequence: Synthetic
      polypeptide
<220> FEATURE:
<221> NAME/KEY: MOD_RES
<222> LOCATION: (24)..(24)
<223> OTHER INFORMATION: Gla

<400> SEQUENCE: 119

Ala Glu Gln Asn Pro Ile Tyr Trp Ala Arg Tyr Ala Asp Trp Leu Phe
1               5                   10                  15

Thr Thr Pro Leu Leu Leu Leu Xaa Leu Ala Leu Leu Val Asp Ala Asp
            20                  25                  30

Glu Thr

<210> SEQ ID NO 120
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (13)..(13)
<223> OTHER INFORMATION: Gla
<220> FEATURE:
<221> NAME/KEY: MOD_RES
<222> LOCATION: (24)..(24)
<223> OTHER INFORMATION: Gla

<400> SEQUENCE: 120

Ala Glu Gln Asn Pro Ile Tyr Trp Ala Arg Tyr Ala Xaa Trp Leu Phe
1               5                   10                  15

Thr Thr Pro Leu Leu Leu Leu Xaa Leu Ala Leu Leu Val Asp Ala Asp
            20                  25                  30

Glu Thr

<210> SEQ ID NO 121
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (13)..(13)
<223> OTHER INFORMATION: Aad

<400> SEQUENCE: 121

Ala Glu Gln Asn Pro Ile Tyr Trp Ala Arg Tyr Ala Xaa Trp Leu Phe
1               5                   10                  15

Thr Thr Pro Leu Leu Leu Leu Asp Leu Ala Leu Leu Val Asp Ala Asp
            20                  25                  30

Glu Thr

<210> SEQ ID NO 122
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (24)..(24)
<223> OTHER INFORMATION: Aad
```

-continued

<400> SEQUENCE: 122

Ala Glu Gln Asn Pro Ile Tyr Trp Ala Arg Tyr Ala Asp Trp Leu Phe
1               5                   10                  15

Thr Thr Pro Leu Leu Leu Leu Xaa Leu Ala Leu Leu Val Asp Ala Asp
            20                  25                  30

Glu Thr

<210> SEQ ID NO 123
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (13)..(13)
<223> OTHER INFORMATION: Aad
<220> FEATURE:
<221> NAME/KEY: MOD_RES
<222> LOCATION: (24)..(24)
<223> OTHER INFORMATION: Aad

<400> SEQUENCE: 123

Ala Glu Gln Asn Pro Ile Tyr Trp Ala Arg Tyr Ala Xaa Trp Leu Phe
1               5                   10                  15

Thr Thr Pro Leu Leu Leu Leu Xaa Leu Ala Leu Leu Val Asp Ala Asp
            20                  25                  30

Glu Thr

<210> SEQ ID NO 124
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (13)..(13)
<223> OTHER INFORMATION: Gla
<220> FEATURE:
<221> NAME/KEY: MOD_RES
<222> LOCATION: (24)..(24)
<223> OTHER INFORMATION: Aad

<400> SEQUENCE: 124

Ala Glu Gln Asn Pro Ile Tyr Trp Ala Arg Tyr Ala Xaa Trp Leu Phe
1               5                   10                  15

Thr Thr Pro Leu Leu Leu Leu Xaa Leu Ala Leu Leu Val Asp Ala Asp
            20                  25                  30

Glu Thr

<210> SEQ ID NO 125
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (13)..(13)
<223> OTHER INFORMATION: Aad
<220> FEATURE:
<221> NAME/KEY: MOD_RES
<222> LOCATION: (24)..(24)
<223> OTHER INFORMATION: Gla

<400> SEQUENCE: 125

Ala Glu Gln Asn Pro Ile Tyr Trp Ala Arg Tyr Ala Xaa Trp Leu Phe
1               5                   10                  15

Thr Thr Pro Leu Leu Leu Leu Xaa Leu Ala Leu Leu Val Asp Ala Asp
            20                  25                  30

Glu Thr

<210> SEQ ID NO 126
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr
            35

<210> SEQ ID NO 127
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr
            35

<210> SEQ ID NO 128
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Ala Ala Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr
            35

<210> SEQ ID NO 129
<211> LENGTH: 35
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 129

Ala Glu Gln Asn Pro Ile Tyr Trp Ala Arg Tyr Ala Asp Trp Leu Phe
1               5                   10                  15

Thr Thr Pro Leu Leu Leu Leu Asp Leu Ala Leu Leu Val Asp Ala Asp
            20                  25                  30

Glu Gly Thr
        35

<210> SEQ ID NO 130
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Ala Glu Gln Asn Pro Ile Tyr Trp Ala Arg Tyr Ala Asn Trp Leu Phe
1               5                   10                  15

Thr Thr Pro Leu Leu Leu Leu Asn Leu Ala Leu Leu Val Asp Ala Asp
            20                  25                  30

Glu Gly Thr
        35

<210> SEQ ID NO 131
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Ala Glu Gln Asn Pro Ile Tyr Trp Ala Arg Tyr Ala Lys Trp Leu Phe
1               5                   10                  15

Thr Thr Pro Leu Leu Leu Leu Lys Leu Ala Leu Leu Val Asp Ala Asp
            20                  25                  30

Glu Gly Thr
        35

<210> SEQ ID NO 132
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asn Ala
            20                  25                  30

Asn Gln Gly Thr
        35

<210> SEQ ID NO 133
<211> LENGTH: 36
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 133

Ala Ala Glu Gln Asn Pro Ile Tyr Trp Ala Arg Tyr Ala Asp Trp Leu
1               5                   10                  15

Phe Thr Thr Pro Leu Leu Leu Leu Ala Leu Ala Leu Leu Val Asp Ala
                20                  25                  30

Asp Glu Gly Thr
            35

<210> SEQ ID NO 134
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Ala Ala Glu Gln Asn Pro Ile Tyr Trp Ala Arg Tyr Ala Ala Trp Leu
1               5                   10                  15

Phe Thr Thr Pro Leu Leu Leu Leu Asp Leu Ala Leu Leu Val Asp Ala
                20                  25                  30

Asp Glu Gly Thr
            35

<210> SEQ ID NO 135
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Ala Ala Glu Gln Asn Pro Ile Tyr Trp Ala Arg Tyr Ala Asp Trp Leu
1               5                   10                  15

Phe Thr Thr Ala Leu Leu Leu Leu Asp Leu Ala Leu Leu Val Asp Ala
                20                  25                  30

Asp Glu Gly Thr
            35

<210> SEQ ID NO 136
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Ala Ala Glu Gln Asn Pro Ile Tyr Trp Ala Arg Tyr Ala Asp Trp Leu
1               5                   10                  15

Phe Thr Thr Pro Leu Leu Leu Leu Glu Leu Ala Leu Leu Val Asp Ala
                20                  25                  30

Asp Glu Gly Thr
            35

<210> SEQ ID NO 137
<211> LENGTH: 36
<212> TYPE: PRT
```

<213> ORGANISM: Artificial Sequence
<220> FEATURE:
<223> OTHER INFORMATION: Description of Artificial Sequence: Synthetic
    polypeptide

<400> SEQUENCE: 137

Ala Ala Glu Gln Asn Pro Ile Tyr Trp Ala Arg Tyr Ala Glu Trp Leu
1               5                   10                  15

Phe Thr Thr Pro Leu Leu Leu Leu Asp Leu Ala Leu Leu Val Asp Ala
            20                  25                  30

Asp Glu Gly Thr
        35

<210> SEQ ID NO 138
<211> LENGTH: 39
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 138

Ala Ala Glu Gln Asn Pro Ile Ile Tyr Trp Ala Arg Tyr Ala Asp Trp
1               5                   10                  15

Leu Phe Thr Asp Leu Pro Leu Leu Leu Asp Leu Leu Ala Leu Leu
            20                  25                  30

Val Asp Ala Asp Glu Gly Thr
        35

<210> SEQ ID NO 139
<211> LENGTH: 34
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 139

Gly Glu Gln Asn Pro Ile Tyr Trp Ala Gln Tyr Ala Asp Trp Leu Phe
1               5                   10                  15

Thr Thr Pro Leu Leu Leu Asp Leu Ala Leu Leu Val Asp Ala Asp
            20                  25                  30

Glu Gly

<210> SEQ ID NO 140
<211> LENGTH: 35
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 140

Gly Gly Glu Gln Asn Pro Ile Tyr Trp Ala Arg Tyr Ala Asp Trp Leu
1               5                   10                  15

Phe Thr Thr Pro Leu Leu Leu Asp Leu Leu Ala Leu Leu Val Asp Ala
            20                  25                  30

Asp Glu Gly
        35

<210> SEQ ID NO 141
<211> LENGTH: 35
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 141

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Ala Leu Leu Val Asp Ala
            20                  25                  30

Asp Glu Gly
        35

<210> SEQ ID NO 142
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Gly Gly Glu Gln Asn Pro Ile Tyr Trp Ala Arg Tyr Asp Ala Trp Leu
1               5                   10                  15

Phe Thr Thr Pro Leu Leu Leu Leu Asp Leu Ala Leu Leu Val Asp Ala
            20                  25                  30

Asp Glu Gly Thr
        35

<210> SEQ ID NO 143
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Gly Gly Glu Gln Asn Pro Ile Tyr Trp Ala Arg Tyr Ala Trp Asp Leu
1               5                   10                  15

Phe Thr Thr Pro Leu Leu Leu Leu Asp Leu Ala Leu Leu Val Asp Ala
            20                  25                  30

Asp Glu Gly
        35

<210> SEQ ID NO 144
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Ala Ala Glu Gln Asn Pro Ile Tyr Trp Ala Arg Tyr Ala Asp Trp Leu
1               5                   10                  15

Phe Thr Thr Gly Leu Leu Leu Leu Asp Leu Ala Leu Leu Val Asp Ala
            20                  25                  30

Asp Glu Gly Thr
        35

<210> SEQ ID NO 145
<211> LENGTH: 34
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Asp Asp Asp Glu Asp Asn Pro Ile Tyr Trp Ala Arg Tyr Ala Asp Trp
1               5                   10                  15

Leu Phe Thr Thr Pro Leu Leu Leu Leu His Gly Ala Leu Leu Val Asp
            20                  25                  30

Ala Asp

<210> SEQ ID NO 146
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asp
            20                  25                  30

Ala Asp Glu
        35

<210> SEQ ID NO 147
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Cys Glu Gln Asn Pro Ile Tyr Trp Ala Arg Tyr Ala Asp Trp His Phe
1               5                   10                  15

Thr Thr Pro Leu Leu Leu Asp Leu Ala Leu Leu Val Asp Ala Asp
            20                  25                  30

Glu

<210> SEQ ID NO 148
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Ala Glu Gln Asn Pro Ile Tyr Trp Ala Arg Tyr Ala Asp Phe Leu Phe
1               5                   10                  15

Thr Thr Pro Leu Leu Leu Asp Leu Ala Leu Leu Val Asp Ala Asp
            20                  25                  30

Glu Thr

<210> SEQ ID NO 149
<211> LENGTH: 33
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 149

Ala Glu Gln Asn Pro Ile Tyr Phe Ala Arg Tyr Ala Asp Trp Leu Phe
1               5                   10                  15

Thr Thr Pro Leu Leu Leu Leu Asp Leu Ala Leu Leu Val Asp Ala Asp
            20                  25                  30

Glu

<210> SEQ ID NO 150
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Ala Glu Gln Asn Pro Ile Tyr Phe Ala Arg Tyr Ala Asp Phe Leu Phe
1               5                   10                  15

Thr Thr Pro Leu Leu Leu Leu Asp Leu Ala Leu Leu Trp Asp Ala Asp
            20                  25                  30

Glu Thr

<210> SEQ ID NO 151
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Ala Asp Asn Asn Pro Trp Ile Tyr Ala Arg Tyr Ala Asp Leu Thr Thr
1               5                   10                  15

Phe Pro Leu Leu Leu Leu Asp Leu Ala Leu Leu Val Asp Phe Asp Asp
            20                  25                  30

<210> SEQ ID NO 152
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Ala Asp Asn Asn Pro Phe Ile Tyr Ala Arg Tyr Ala Asp Leu Thr Thr
1               5                   10                  15

Trp Pro Leu Leu Leu Leu Asp Leu Ala Leu Leu Val Asp Phe Asp Asp
            20                  25                  30

<210> SEQ ID NO 153
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Ala Asp Asn Asn Pro Phe Ile Tyr Ala Arg Tyr Ala Asp Leu Thr Thr
```

```
                1               5                  10                  15
Phe Pro Leu Leu Leu Leu Asp Leu Ala Leu Leu Val Asp Trp Asp Asp
                20                  25                  30
```

<210> SEQ ID NO 154
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

```
Ala Asp Asn Asn Pro Phe Pro Tyr Ala Arg Tyr Ala Asp Leu Thr Thr
1               5                  10                  15

Trp Ile Leu Leu Leu Leu Asp Leu Ala Leu Leu Val Asp Phe Asp Asp
                20                  25                  30
```

<210> SEQ ID NO 155
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

```
Ala Asp Asn Asn Pro Phe Ile Tyr Ala Tyr Arg Ala Asp Leu Thr Thr
1               5                  10                  15

Phe Pro Leu Leu Leu Leu Asp Leu Ala Leu Leu Val Asp Trp Asp Asp
                20                  25                  30
```

<210> SEQ ID NO 156
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

```
Ala Asp Asn Asn Pro Phe Ile Tyr Ala Thr Tyr Ala Asp Leu Arg Thr
1               5                  10                  15

Phe Pro Leu Leu Leu Leu Asp Leu Ala Leu Leu Val Asp Trp Asp Asp
                20                  25                  30
```

<210> SEQ ID NO 157
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

```
Thr Glu Asp Ala Asp Val Leu Leu Ala Leu Asp Leu Leu Leu Leu Pro
1               5                  10                  15

Thr Thr Phe Leu Trp Asp Ala Tyr Arg Ala Trp Tyr Pro Asn Gln Glu
                20                  25                  30

Ala
```

<210> SEQ ID NO 158
<211> LENGTH: 30
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 158

Ala Glu Asp Gln Asn Pro Tyr Trp Ala Arg Tyr Ala Asp Trp Leu Phe
1               5                   10                  15

Thr Thr Pro Leu Leu Leu Leu Asp Leu Ala Leu Leu Val Asp
            20                  25                  30

<210> SEQ ID NO 159
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Ala Glu Asp Gln Asn Pro Tyr Trp Ala Arg Tyr Ala Asp Trp Leu Phe
1               5                   10                  15

Thr Thr Pro Leu Leu Leu Leu Glu Leu Ala Leu Leu Val Glu
            20                  25                  30

<210> SEQ ID NO 160
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Ala Glu Asp Gln Asn Pro Tyr Trp Arg Ala Tyr Ala Asp Leu Phe Thr
1               5                   10                  15

Pro Leu Thr Leu Leu Asp Leu Leu Ala Leu Trp Asp
            20                  25

<210> SEQ ID NO 161
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Ala Asp Asp Gln Asn Pro Trp Arg Ala Tyr Leu Asp Leu Leu Phe Pro
1               5                   10                  15

Thr Asp Thr Leu Leu Leu Asp Leu Leu Trp
            20                  25

<210> SEQ ID NO 162
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Ala Asp Asp Gln Asn Pro Trp Arg Ala Tyr Leu Asp Leu Leu Phe Pro
1               5                   10                  15

Thr Asp Thr Leu Leu Leu Asp Leu Leu Trp Asp Ala Asp Glu
```

<210> SEQ ID NO 163
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Gla

<400> SEQUENCE: 163

Ala Asp Asp Gln Asn Pro Trp Arg Ala Tyr Leu Xaa Leu Leu Phe Pro
1               5                   10                  15

Thr Asp Thr Leu Leu Leu Asp Leu Leu Trp
            20                  25

<210> SEQ ID NO 164
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Gla

<400> SEQUENCE: 164

Ala Asp Asp Gln Asn Pro Trp Arg Ala Tyr Leu Asp Leu Leu Phe Pro
1               5                   10                  15

Thr Xaa Thr Leu Leu Leu Asp Leu Leu Trp
            20                  25

<210> SEQ ID NO 165
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Gla

<400> SEQUENCE: 165

Ala Asp Asp Gln Asn Pro Trp Arg Ala Tyr Leu Asp Leu Leu Phe Pro
1               5                   10                  15

Thr Asp Thr Leu Leu Leu Xaa Leu Leu Trp
            20                  25

<210> SEQ ID NO 166
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Gla
<220> FEATURE:
<221> NAME/KEY: MOD_RES
<222> LOCATION: (18)..(18)
<223> OTHER INFORMATION: Gla

<400> SEQUENCE: 166

Ala Asp Asp Gln Asn Pro Trp Arg Ala Tyr Leu Xaa Leu Leu Phe Pro
1               5                   10                  15

Thr Xaa Thr Leu Leu Leu Asp Leu Leu Trp
            20                  25

<210> SEQ ID NO 167
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Gla
<220> FEATURE:
<221> NAME/KEY: MOD_RES
<222> LOCATION: (23)..(23)
<223> OTHER INFORMATION: Gla

<400> SEQUENCE: 167

Ala Asp Asp Gln Asn Pro Trp Arg Ala Tyr Leu Xaa Leu Leu Phe Pro
1               5                   10                  15

Thr Asp Thr Leu Leu Xaa Leu Leu Trp
            20                  25

<210> SEQ ID NO 168
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Gla
<220> FEATURE:
<221> NAME/KEY: MOD_RES
<222> LOCATION: (23)..(23)
<223> OTHER INFORMATION: Gla

<400> SEQUENCE: 168

Ala Asp Asp Gln Asn Pro Trp Arg Ala Tyr Leu Asp Leu Leu Phe Pro
1               5                   10                  15

Thr Xaa Thr Leu Leu Leu Xaa Leu Leu Trp
            20                  25

<210> SEQ ID NO 169
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Gla
<220> FEATURE:
<221> NAME/KEY: MOD_RES
<222> LOCATION: (18)..(18)
<223> OTHER INFORMATION: Gla
<220> FEATURE:
<221> NAME/KEY: MOD_RES
<222> LOCATION: (23)..(23)
<223> OTHER INFORMATION: Gla

<400> SEQUENCE: 169

Ala Asp Asp Gln Asn Pro Trp Arg Ala Tyr Leu Xaa Leu Leu Phe Pro
1               5                   10                  15

Thr Xaa Thr Leu Leu Leu Xaa Leu Leu Trp
            20                  25

<210> SEQ ID NO 170
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Aad

<400> SEQUENCE: 170

Ala Asp Asp Gln Asn Pro Trp Arg Ala Tyr Leu Xaa Leu Leu Phe Pro
1               5                   10                  15

Thr Asp Thr Leu Leu Leu Asp Leu Leu Trp
            20                  25

<210> SEQ ID NO 171
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Aad

<400> SEQUENCE: 171

Ala Asp Asp Gln Asn Pro Trp Arg Ala Tyr Leu Asp Leu Leu Phe Pro
1               5                   10                  15

Thr Xaa Thr Leu Leu Leu Asp Leu Leu Trp
            20                  25

<210> SEQ ID NO 172
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Aad

<400> SEQUENCE: 172

Ala Asp Asp Gln Asn Pro Trp Arg Ala Tyr Leu Asp Leu Leu Phe Pro
1               5                   10                  15

Thr Asp Thr Leu Leu Leu Xaa Leu Leu Trp
            20                  25

<210> SEQ ID NO 173
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Aad
<220> FEATURE:
<221> NAME/KEY: MOD_RES
<222> LOCATION: (18)..(18)
<223> OTHER INFORMATION: Aad

<400> SEQUENCE: 173

Ala Asp Asp Gln Asn Pro Trp Arg Ala Tyr Leu Xaa Leu Leu Phe Pro
1               5                   10                  15

Thr Xaa Thr Leu Leu Leu Asp Leu Leu Trp
            20                  25

<210> SEQ ID NO 174
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Aad
<220> FEATURE:
<221> NAME/KEY: MOD_RES
<222> LOCATION: (23)..(23)
<223> OTHER INFORMATION: Aad

<400> SEQUENCE: 174

Ala Asp Asp Gln Asn Pro Trp Arg Ala Tyr Leu Xaa Leu Leu Phe Pro
1               5                   10                  15

Thr Asp Thr Leu Leu Leu Xaa Leu Leu Trp
            20                  25

<210> SEQ ID NO 175
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Aad
<220> FEATURE:
<221> NAME/KEY: MOD_RES
<222> LOCATION: (23)..(23)
<223> OTHER INFORMATION: Aad

<400> SEQUENCE: 175

Ala Asp Asp Gln Asn Pro Trp Arg Ala Tyr Leu Asp Leu Leu Phe Pro
1               5                   10                  15

Thr Xaa Thr Leu Leu Leu Xaa Leu Leu Trp
            20                  25

<210> SEQ ID NO 176
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:

-continued

```
<221> NAME/KEY: MOD_RES
<222> LOCATION: (12)..(12)
<223> OTHER INFORMATION: Aad
<220> FEATURE:
<221> NAME/KEY: MOD_RES
<222> LOCATION: (18)..(18)
<223> OTHER INFORMATION: Aad
<220> FEATURE:
<221> NAME/KEY: MOD_RES
<222> LOCATION: (23)..(23)
<223> OTHER INFORMATION: Aad

<400> SEQUENCE: 176

Ala Asp Asp Gln Asn Pro Trp Arg Ala Tyr Leu Xaa Leu Leu Phe Pro
1               5                   10                  15

Thr Xaa Thr Leu Leu Leu Xaa Leu Leu Trp
            20                  25

<210> SEQ ID NO 177
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Gla
<220> FEATURE:
<221> NAME/KEY: MOD_RES
<222> LOCATION: (18)..(18)
<223> OTHER INFORMATION: Aad

<400> SEQUENCE: 177

Ala Asp Asp Gln Asn Pro Trp Arg Ala Tyr Leu Xaa Leu Leu Phe Pro
1               5                   10                  15

Thr Xaa Thr Leu Leu Leu Asp Leu Leu Trp
            20                  25

<210> SEQ ID NO 178
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Gla
<220> FEATURE:
<221> NAME/KEY: MOD_RES
<222> LOCATION: (23)..(23)
<223> OTHER INFORMATION: Aad

<400> SEQUENCE: 178

Ala Asp Asp Gln Asn Pro Trp Arg Ala Tyr Leu Xaa Leu Leu Phe Pro
1               5                   10                  15

Thr Asp Thr Leu Leu Leu Xaa Leu Leu Trp
            20                  25

<210> SEQ ID NO 179
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (12)..(12)
<223> OTHER INFORMATION: Gla
<220> FEATURE:
<221> NAME/KEY: MOD_RES
<222> LOCATION: (18)..(18)
<223> OTHER INFORMATION: Gla
<220> FEATURE:
<221> NAME/KEY: MOD_RES
<222> LOCATION: (23)..(23)
<223> OTHER INFORMATION: Aad

<400> SEQUENCE: 179

Ala Asp Asp Gln Asn Pro Trp Arg Ala Tyr Leu Xaa Leu Leu Phe Pro
1               5                   10                  15

Thr Xaa Thr Leu Leu Leu Xaa Leu Leu Trp
            20                  25

<210> SEQ ID NO 180
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Aad
<220> FEATURE:
<221> NAME/KEY: MOD_RES
<222> LOCATION: (18)..(18)
<223> OTHER INFORMATION: Gla

<400> SEQUENCE: 180

Ala Asp Asp Gln Asn Pro Trp Arg Ala Tyr Leu Xaa Leu Leu Phe Pro
1               5                   10                  15

Thr Xaa Thr Leu Leu Leu Asp Leu Leu Trp
            20                  25

<210> SEQ ID NO 181
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Aad
<220> FEATURE:
<221> NAME/KEY: MOD_RES
<222> LOCATION: (23)..(23)
<223> OTHER INFORMATION: Gla

<400> SEQUENCE: 181

Ala Asp Asp Gln Asn Pro Trp Arg Ala Tyr Leu Xaa Leu Leu Phe Pro
1               5                   10                  15

Thr Asp Thr Leu Leu Leu Xaa Leu Leu Trp
            20                  25

<210> SEQ ID NO 182
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (12)..(12)
<223> OTHER INFORMATION: Gla
<220> FEATURE:
<221> NAME/KEY: MOD_RES
<222> LOCATION: (18)..(18)
<223> OTHER INFORMATION: Aad
<220> FEATURE:
<221> NAME/KEY: MOD_RES
<222> LOCATION: (23)..(23)
<223> OTHER INFORMATION: Gla

<400> SEQUENCE: 182

Ala Asp Asp Gln Asn Pro Trp Arg Ala Tyr Leu Xaa Leu Leu Phe Pro
1               5                   10                  15

Thr Xaa Thr Leu Leu Leu Xaa Leu Leu Trp
            20                  25

<210> SEQ ID NO 183
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Gly Glu Glu Gln Asn Pro Trp Leu Gly Ala Tyr Leu Asp Leu Leu Phe
1               5                   10                  15

Pro Leu Glu Leu Leu Gly Leu Leu Glu Leu Gly Leu Trp
            20                  25

<210> SEQ ID NO 184
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Ala Asp Asp Asp Asp Asp Asp Pro Trp Gln Ala Tyr Leu Asp Leu Leu
1               5                   10                  15

Phe Pro Thr Asp Thr Leu Leu Leu Asp Leu Leu Trp
            20                  25

<210> SEQ ID NO 185
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Ala Glu Glu Gln Asn Pro Trp Arg Ala Tyr Leu Glu Leu Leu Phe Pro
1               5                   10                  15

Thr Glu Thr Leu Leu Leu Glu Leu Leu Trp
            20                  25

<210> SEQ ID NO 186
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 186

Ala Asp Asp Gln Asn Pro Trp Ala Arg Tyr Leu Asp Trp Leu Phe Pro
1               5                   10                  15

Thr Asp Thr Leu Leu Leu Asp Leu
            20

<210> SEQ ID NO 187
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Asp Asn Asn Asn Pro Trp Arg Ala Tyr Leu Asp Leu Leu Phe Pro Thr
1               5                   10                  15

Asp Thr Leu Leu Leu Asp Trp
            20

<210> SEQ ID NO 188
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Ala Glu Glu Gln Asn Pro Trp Ala Arg Tyr Leu Glu Trp Leu Phe Pro
1               5                   10                  15

Thr Glu Thr Leu Leu Leu Glu Leu
            20

<210> SEQ ID NO 189
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Asp Asp Asp Asp Asp Asp Pro Trp Gln Ala Tyr Leu Asp Leu Phe Pro
1               5                   10                  15

Thr Asp Thr Leu Ala Leu Asp Leu Trp
            20                  25

<210> SEQ ID NO 190
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Glu Glu Gln Gln Pro Trp Ala Gln Tyr Leu Glu Leu Leu Phe Pro Thr
1               5                   10                  15

Glu Thr Leu Leu Leu Glu Trp
            20

<210> SEQ ID NO 191

```
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Glu Glu Gln Gln Pro Trp Arg Ala Tyr Leu Glu Leu Leu Phe Pro Thr
1               5                   10                  15

Glu Thr Leu Leu Leu Glu Trp
            20

<210> SEQ ID NO 192
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Ala Glu Asp Gln Asn Pro Trp Ala Arg Tyr Ala Asp Trp Leu Phe Pro
1               5                   10                  15

Thr Thr Leu Leu Leu Leu Asp
            20

<210> SEQ ID NO 193
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Ala Glu Glu Gln Asn Pro Trp Ala Arg Tyr Ala Glu Trp Leu Phe Pro
1               5                   10                  15

Thr Thr Leu Leu Leu Leu Glu
            20

<210> SEQ ID NO 194
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Ala Glu Asp Gln Asn Pro Trp Ala Arg Tyr Ala Asp Leu Leu Phe Pro
1               5                   10                  15

Thr Thr Leu Ala Trp
            20

<210> SEQ ID NO 195
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Ala Glu Glu Gln Asn Pro Trp Ala Arg Tyr Ala Glu Leu Leu Phe Pro
1               5                   10                  15
```

```
Thr Thr Leu Ala Trp
            20

<210> SEQ ID NO 196
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Asp Asp Asp Asp Asp Asn Pro Asn Tyr Trp Ala Arg Tyr Ala Asn Trp
1               5                   10                  15

Leu Phe Thr Thr Pro Leu Leu Leu Leu Asn Gly Ala Leu Leu Val Glu
            20                  25                  30

Ala Glu Glu Thr
        35

<210> SEQ ID NO 197
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Asp Asp Asp Asp Asp Asn Pro Asn Tyr Trp Ala Arg Tyr Ala Pro Trp
1               5                   10                  15

Leu Phe Thr Thr Pro Leu Leu Leu Leu Pro Gly Ala Leu Leu Val Glu
            20                  25                  30

Ala Glu Glu Thr
        35

<210> SEQ ID NO 198
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Ala Glu Gln Asn Pro Ile Tyr Phe Ala Arg Tyr Ala Asp Phe Leu Phe
1               5                   10                  15

Thr Thr Pro Leu Leu Leu Leu Asp Leu Ala Leu Leu Trp Asp Ala Asp
            20                  25                  30

Glu Thr

<210> SEQ ID NO 199
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Ala Glu Gln Asn Pro Ile Tyr Trp Ala Arg Tyr Ala Asp Phe Leu Phe
1               5                   10                  15

Thr Thr Pro Leu Leu Leu Leu Asp Leu Ala Leu Leu Val Asp Ala Asp
            20                  25                  30
```

Glu Thr

<210> SEQ ID NO 200
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Ala Glu Gln Asn Pro Ile Tyr Trp Ala Arg Tyr Ala Asp Trp Leu Phe
1               5                   10                  15

Thr Thr Pro Leu
            20

<210> SEQ ID NO 201
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Ala Glu Gln Asn Pro Ile Tyr Phe Ala Arg Tyr Ala Asp Leu Leu Phe
1               5                   10                  15

Pro Thr Thr Leu Ala Trp
            20

<210> SEQ ID NO 202
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Ala Glu Gln Asn Pro Ile Tyr Trp Ala Arg Tyr Ala Asp Leu Leu Phe
1               5                   10                  15

Pro Thr Thr Leu Ala Phe
            20

<210> SEQ ID NO 203
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Ala Glu Gln Asn Pro Ile Tyr Trp Ala Arg Tyr Ala Asp Leu Leu Phe
1               5                   10                  15

Pro Thr Thr Leu Ala Trp
            20

<210> SEQ ID NO 204
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Ala Glu Gln Asn Pro Ile Tyr Phe Ala Arg Tyr Ala Asp Trp Leu Phe
1               5                   10                  15

Thr Thr Pro Leu
            20

<210> SEQ ID NO 205
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Glu Asp Gln Asn Pro Trp Ala Arg Tyr Ala Asp Leu Leu Phe Pro Thr
1               5                   10                  15

Thr Leu Ala Trp
            20

<210> SEQ ID NO 206
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Gly Leu Ala Gly Leu Ala Gly Leu Leu Gly Leu Glu Gly Leu Leu Gly
1               5                   10                  15

Leu Pro Leu Gly Leu Leu Glu Gly Leu Trp Leu Gly Leu Glu Leu Glu
            20                  25                  30

Gly Asn

<210> SEQ ID NO 207
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Glu Gln Asn Pro Ile Tyr Ile Leu Asp Leu Val Phe Gly Leu Leu Phe
1               5                   10                  15

Ala Val Thr Ser Val Asp Phe Leu Val Gln Trp Asp Asp Ala Gly Asp
            20                  25                  30

<210> SEQ ID NO 208
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Asn Leu Glu Gly Phe Phe Ala Thr Leu Gly Gly Glu Ile Ala Leu Trp
1               5                   10                  15

Ser Leu Val Val Leu Ala Ile Glu
            20

-continued

```
<210> SEQ ID NO 209
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Asn Asn Glu Gly Phe Phe Ala Thr Leu Gly Gly Glu Ile Ala Leu Trp
1               5                   10                  15

Ser Asp Val Val Leu Ala Ile Glu
            20

<210> SEQ ID NO 210
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Asp Asn Asn Glu Gly Phe Phe Ala Thr Leu Gly Gly Glu Ile Pro Leu
1               5                   10                  15

Trp Ser Asp Val Val Leu Ala Ile Glu
            20                  25

<210> SEQ ID NO 211
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Ala Glu Gln Asn Pro Ile Tyr Trp Ala Arg Tyr Ala Asp Trp Leu Phe
1               5                   10                  15

Thr Thr Pro Leu Leu Leu Leu Asp Leu Ala Leu Leu Val Asp Ala Asp
            20                  25                  30

Glu Gly Cys Thr
        35

<210> SEQ ID NO 212
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Ala Asp Gln Asp Asn Pro Trp Arg Ala Tyr Leu Asp Leu Leu Phe Pro
1               5                   10                  15

Thr Asp Thr Leu Leu Leu Asp Leu Leu Trp Cys Ala
            20                  25

<210> SEQ ID NO 213
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 213

Ala Asp Gln Asp Asn Pro Trp Arg Ala Tyr Leu Asp Leu Leu Phe Pro
1               5                   10                  15

Thr Asp Thr Leu Leu Leu Asp Leu Leu Trp Lys Ala
            20                  25

<210> SEQ ID NO 214
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (27)..(27)
<223> OTHER INFORMATION: Any amino acid
<220> FEATURE:
<223> OTHER INFORMATION: See specification as filed for detailed
      description of substitutions and preferred embodiments

<400> SEQUENCE: 214

Ala Asp Gln Asp Asn Pro Trp Arg Ala Tyr Leu Asp Leu Leu Phe Pro
1               5                   10                  15

Thr Asp Thr Leu Leu Leu Asp Leu Leu Trp Xaa Ala
            20                  25

<210> SEQ ID NO 215
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (27)..(27)
<223> OTHER INFORMATION: Lys, Cys or an Azido-containing amino acid
<220> FEATURE:
<223> OTHER INFORMATION: See specification as filed for detailed
      description of substitutions and preferred embodiments

<400> SEQUENCE: 215

Ala Asp Asp Gln Asn Pro Trp Arg Ala Tyr Leu Asp Leu Leu Phe Pro
1               5                   10                  15

Thr Asp Thr Leu Leu Asp Leu Leu Trp Xaa Ala
            20                  25

<210> SEQ ID NO 216
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (27)..(27)
<223> OTHER INFORMATION: Lys, Cys or an Azido-containing amino acid
<220> FEATURE:
<223> OTHER INFORMATION: See specification as filed for detailed
      description of substitutions and preferred embodiments

<400> SEQUENCE: 216

Ala Asp Gln Asp Asn Pro Trp Arg Ala Tyr Leu Asp Leu Leu Phe Pro
1               5                   10                  15

Thr Asp Thr Leu Leu Leu Asp Leu Leu Trp Xaa Ala

```
<210> SEQ ID NO 217
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Ala Asp Asp Gln Asn Pro Trp Arg Ala Tyr Leu Asp Leu Leu Phe Pro
1               5                   10                  15

Thr Asp Thr Leu Leu Leu Asp Leu Leu Trp Lys Ala
            20                  25
```